United States Patent
Witschel et al.

(10) Patent No.: US 8,133,851 B2
(45) Date of Patent: Mar. 13, 2012

(54) HETEROAROYL-SUBSTITUTED SERINE AMIDES

(75) Inventors: Matthias Witschel, Bad Dürkheim (DE); Dschun Song, Mannheim (DE); Eike Hupe, Ludwigshafen (DE); Trevor William Newton, Neustadt (DE); William Karl Moberg, Hassloch (DE); Liliana Parra Rapado, Offenburg (DE); Frank Stelzer, Mannheim (DE); Andrea Vescovi, Mannheim (DE); Robert Reinhard, Limburgerhof (DE); Bernd Sievernich, Haβloch (DE); Klaus Groβmann, Neuhofen (DE); Thomas Ehrhardt, Speyer (DE)

(73) Assignee: BASF SE, Ludwigshafen (DE)

( * ) Notice: Subject to any disclaimer, the term of this patent is extended or adjusted under 35 U.S.C. 154(b) by 77 days.

(21) Appl. No.: 12/522,644

(22) PCT Filed: Jan. 10, 2008

(86) PCT No.: PCT/EP2008/050228
§ 371 (c)(1),
(2), (4) Date: Jul. 9, 2009

(87) PCT Pub. No.: WO2008/084073
PCT Pub. Date: Jul. 17, 2008

(65) Prior Publication Data
US 2010/0099568 A1    Apr. 22, 2010

(30) Foreign Application Priority Data
Jan. 11, 2007    (EP) .................................. 07100427

(51) Int. Cl.
*A01N 43/56* (2006.01)
*C07D 231/10* (2006.01)

(52) U.S. Cl. .................. 504/280; 548/356.1; 548/374.1; 504/261

(58) Field of Classification Search ............... 548/356.1, 548/373.1, 374.1; 504/261, 280
See application file for complete search history.

(56) References Cited

U.S. PATENT DOCUMENTS
7,879,761 B2 * 2/2011 Witschel et al. .............. 504/280

FOREIGN PATENT DOCUMENTS
| WO | WO 2005/061443 | 7/2005 |
| WO | WO 2006/029828 | 3/2006 |
| WO | WO 2006/029829 | 3/2006 |
| WO | WO 2006/125687 | 11/2006 |
| WO | WO 2007/134984 | 11/2007 |

OTHER PUBLICATIONS

Witschel et al (2006): STN International HCAPLUS database, Columbus (OH), accession No. 2006: 1253055.*
International Search Report for International Application No. PCT/EP2008/050228; International Filing Date: Jan. 10, 2008; Date of Completion: Feb. 18, 2008; Date of Mailing: Feb. 28, 2008.
International Preliminary Repot on Patentability Report for International Application No. PCT/EP2008/050228; International Filing Date: Jan. 10, 2008.

* cited by examiner

*Primary Examiner* — Golam M M Shameem
(74) *Attorney, Agent, or Firm* — Brinks Hofer Gilson & Lione

(57) ABSTRACT

The present invention relates to heteroaroyl-substituted serinamides of the formula (I)

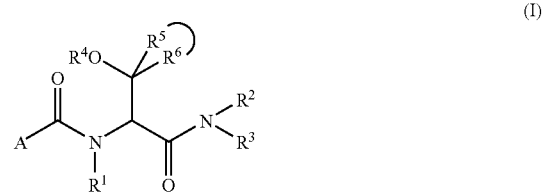

in which the variables A and $R^1$ to $R^6$ are as defined in the description,
and to their agriculturally useful salts,
to processes and intermediates for their preparation, and to the use of these compounds or of the compositions comprising these compounds for controlling unwanted plants.

8 Claims, No Drawings

HETEROAROYL-SUBSTITUTED SERINE AMIDES

This application is a National Stage application of International Application No. PCT/EP2008/050228 filed Jan. 10, 2008, the entire contents of which is hereby incorporated herein by reference. This application also claims the benefit under 35 U.S.C. §119 of European Patent Application No. 07100427.9, filed Jan. 11, 2007, the entire contents of which is hereby incorporated herein by reference.

The invention relates to heteroaroyl-substituted serineamides of formula (I)

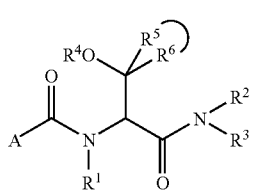

in which the variables are as defined below:
A is 5- or 6-membered heteroaryl having one to four nitrogen atoms or one to three nitrogen atoms and one oxygen or sulfur atom or one oxygen or sulfur atom, which heteroaryl may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;

$R^1$, $R^2$ are hydrogen, hydroxyl or $C_1$-$C_6$-alkoxy;

$R^3$ is $C_1$-$C_6$-alkyl, $C_1$-$C_4$-cyanoalkyl or $C_1$-$C_6$-haloalkyl;

$R^4$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkyl-carbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, di-($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)amino-carbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, ($C_1$-$C_6$)alkylaminothiocarbonyl, di-($C_1$-$C_6$-alkyl)aminothiocarbonyl, ($C_1$-$C_6$-alkyl)-cyanoimino, (amino)cyanoimino, [($C_1$-$C_6$-alkyl)amino]cyanoimino, [di($C_1$-$C_6$-alkyl)-amino]cyanoimino, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl, N-(di-$C_1$-$C_6$-alkylamino)imino-$C_1$-$C_6$-alkyl or tri-$C_1$-$C_4$-alkylsilyl,
where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, di-($C_1$-$C_4$-alkyl)-amino, $C_1$-$C_4$-alkyl-$C_1$-$C_4$-alkoxycarbonylamino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl,
where the phenyl radical may be partially or fully halogenated and/or may carry 1 to 3 of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
$SO_2R^7$;

$R^5$ and $R^6$ together with the carbon atom to which they are attached are a 3-12-membered saturated or partially unsaturated ring which is carbocyclic or contains 1 to 3 nitrogen atoms, 0 to 3 nitrogen atoms and 1 oxygen or sulfur atom, 0 to 2 nitrogen atoms and 2 oxygen or sulfur atoms, 0 or 1 nitrogen atom and 1 oxygen and 1 sulfur atom, 3 oxygen or sulfur atoms, 2 oxygen atoms and 1 sulfur atom, or 1 oxygen atom and 2 sulfur atoms,
where the ring is unsubstituted or substituted by 1 to 3, in the case of halogen also up to the maximum possible number, substituents from the group consisting of halogen, cyano, nitro, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, hydroxyl, $C_1$-$C_6$-alkoxy, $C_3$-$C_6$-alkenyloxy, $C_3$-$C_6$-alkynyloxy, trialkylsilyloxy, formyl, $C_1$-$C_6$-alkyl-carbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylaminocarbonyl, di-($C_1$-$C_6$-alkyl)-aminocarbonyl, N—($C_3$-$C_6$-alkenyl)-N—($C_1$-$C_6$-alkyl)-aminocarbonyl, N—($C_3$-$C_6$-alkynyl)-N—($C_1$-$C_6$-alkyl)-aminocarbonyl, N—($C_1$-$C_6$-alkoxy)-N—($C_1$-$C_6$-alkyl)-amino-carbonyl, N—($C_3$-$C_6$-alkenyl)-N—($C_1$-$C_6$-alkoxy)-aminocarbonyl, N—($C_3$-$C_6$-alkynyl)-N—($C_1$-$C_6$-alkoxy)-aminocarbonyl, di-($C_1$-$C_6$-alkyl)-amino-thiocarbonyl, $C_1$-$C_6$-alkoxyimino-$C_1$-$C_6$-alkyl, N—($C_1$-$C_6$-alkylamino)-imino-$C_1$-$C_6$-alkyl or N-(di-$C_1$-$C_6$-alkylamino)-imino-$C_1$-$C_6$-alkyl, amino, formylamino, $C_1$-$C_6$-alkylcarbonylamino, $C_1$-$C_6$-alkoxycarbonylamino, $C_1$-$C_6$-alkylamino, formyl-$C_1$-$C_6$-alkylamino, $C_1$-$C_6$-alkylcarbonyl-$C_1$-$C_6$-alkylamino, $C_1$-$C_6$-alkoxycarbonyl-$C_1$-$C_6$-alkylamino, di-($C_1$-$C_6$-alkyl)amino, amino-carbonylamino, $C_1$-$C_6$-alkylaminocarbonylamino, di($C_1$-$C_6$-)alkylaminocarbonylamino, $C_1$-$C_6$-alkylthio, $C_1$-$C_6$alkylsulfonyl, alkylsulfonyloxy, alkylsulfonylamino, $C_1$-$C_6$-alkylsulfinyl, $C_1$-$C_6$-alkylsulfimino, $C_1$-$C_6$-alkyl-$C_1$-$C_6$-alkylsulfimino, carbonyl, thiocarbonyl, imino, alkylimino, hydroxyimino, alkoxyimino, aminoimino, alkylaminoimino, di-(alkyl)aminoimino, alkylcarbonylaminoimino, alkylsulfonylaminoimino, $C_1$-$C_6$-vinylidenyl, $C_1$-$C_6$-alkoxyvinylidene, di-$C_1$-$C_6$-alkylaminovinylidene,
where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di-($C_1$-$C_4$-alkyl)-amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)-aminocarbonyl or $C_1$-$C_4$-alkylcarbonyloxy, phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)-aminocarbonyl, phenyl-$C_1$-$C_6$-alkylcarbonyl, heterocyclyl, heterocyclyl-$C_1$-$C_6$-alkyl, heterocyclylcarbonyl, heterocyclylsulfonylaminocarbonyl; heterocyclylcarbonyl-$C_1$-$C_6$-alkyl, heterocyclyloxycarbonyl, heterocyclylaminocarbonyl, N—($C_1$-$C_6$-alkyl)-N-(heterocyclyl)-aminocarbonyl, or heterocyclyl-$C_1$-$C_6$-alkylcarbonyl, where the phenyl and the heterocyclyl radical of the 17 last-mentioned substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;

and where the ring is monocyclic or fused to a further 3- to 7-membered saturated, partially unsaturated or fully unsaturated ring which is carbocyclic or contains 1 to 3 nitrogen atoms, 0 to 2 nitrogen atoms and 1 oxygen atom or sulfur atom, 0 or 1 nitrogen atom and 2 oxygen atoms or sulfur atoms, 0 or 1 nitrogen atom and 1 oxygen atom and 1 sulfur atom, 2 oxygen atoms and 1 sulfur atom, or 1 oxygen atom and 2 sulfur atoms, where the fused ring is unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl, and where the ring is not bridged or bridged by a 1- to 4-membered saturated or unsaturated chain which contains no heteroatoms or contains 1 to 2 nitrogen atoms, 0 or 1 nitrogen atom and 1 oxygen atom or 1 sulfur atom, 0 or 1 nitrogen atom and 2 oxygen atoms or 2 sulfur atoms, or 0 or 1 nitrogen atom and 1 oxygen atom and 1 sulfur atom, where the bridge is unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl;

$R^7$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_6$-alkoxy;

and their agriculturally useful salts.

Moreover, the invention relates to processes and intermediates for preparing compounds of the formula (I), to compositions comprising them and to the use of these compounds or of the compositions comprising them for controlling harmful plants.

Fungicidally active thienyl-substituted amino acid derivatives which carry, in the α-position, an alkyl radical which may optionally be substituted by hydroxyl or alkoxy are described, inter alia, in EP 450 355.

Also known from the literature, for example from U.S. Pat. No. 5,346,907, WO 96/012499 and WO 02/069905, are serine derivatives having pharmaceutical activity which, in the α-position, may, inter alia, carry an alkyl radical which may optionally be substituted by hydroxyl or alkoxy.

Herbicidally active serine derivatives are known, for example, from WO 03/45878, WO 03/66576, WO 05/061464, WO 05/061443, WO 06/29829 and WO 06/29828.

However, in many cases the known compounds are not entirely satisfactory, for example with respect to application rate, activity spectrum, duration of activity, compatibility with crop plants, tendency to develop resistance or economic aspects of the preparation process.

Accordingly, it is an object of the present invention to provide novel, in particular herbicidally active, compounds having improved properties.

We have found that this object is achieved by the heteroaroyl-substituted serineamides of the formula (I) and their herbicidal action.

Furthermore, we have found herbicidal compositions which comprise the compounds (I) and have very good herbicidal action. Moreover, we have found processes for preparing these compositions and methods for controlling unwanted vegetation using the compounds (I).

Depending on the substitution pattern, the compounds of the formula (I) comprise two or more centers of chiralty, in which case they are present as enantiomers or diastereomer mixtures. The invention provides both the pure enantiomers or diastereomers and their mixtures.

The compounds of the formula (I) may also be present in the form of their agriculturally useful salts, the nature of the salt generally being immaterial. Suitable salts are, in general, the cations or the acid addition salts of those acids whose cation and anions, respectively, have no adverse effect on the herbicidal action of the compounds (I).

Suitable cations are in particular the ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl-ammonium, di-(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate, and the anions of $C_1$-$C_4$-alkanoic acids, preferably formate, acetate, propionate and butyrate.

"Fused" in the sense of the invention means that two rings share at least one atom. Thus, in addition to condensed systems, the definition also includes systems which are spirocyclically linked.

The organic moieties mentioned for the substituents $R^1$-$R^7$ or as radicals on phenyl, aryl, heteroaryl or heterocyclyl rings are collective terms for individual enumerations of the specific group members. All hydrocarbon chains, i.e. all alkyl, alkylsilyl, alkenyl, alkynyl, cyanoalkyl, haloalkyl, haloalkenyl, haloalkynyl, alkoxy, haloalkoxy, alkoxyalkyl, alkoxyalkoxyalkyl, alkylcarbonyl, alkenylcarbonyl, alkynylcarbonyl, alkoxycarbonyl, alkenyloxycarbonyl, alkynyloxycarbonyl, alkylamino, alkylsulfonylamino, haloalkylsulfonylamino, alkylalkoxycarbonylamino, alkylaminocarbonyl, alkenylaminocarbonyl, alkynylaminocarbonyl, alkylsulfonylaminocarbonyl, dialkylaminocarbonyl, N-alkenyl-N-alkylaminocarbonyl, N-alkynyl-N-alkylaminocarbonyl, N-alkoxy-N-alkylaminocarbonyl, N-alkenyl-N-alkoxyaminocarbonyl, N-alkynyl-N-alkoxyaminocarbonyl, dialkylaminothiocarbonyl, alkylcarbonylalkyl, alkoximinoalkyl, N-(alkylamino)iminoalkyl, N-(dialkylamino)iminoalkyl, alkylcyanoimino, alkylaminocyanoimino, dialkylaminocyanoimino, formylaminoalkyl, alkoxycarbonylaminoalkyl, (alkylamino)carbonyloxyalkyl, (alkylamino)carbonylaminoalkyl, (dialkylamino)carbonylaminoalkyl, phenylcarbonylaminoalkyl, phenylalkyl, phenylcarbonylalkyl, N-alkyl-N-phenylaminocarbonyl, phenylalkylcarbonyl, arylalkyl, heterocyclylalkyl, heterocyclylcarbonylalkyl, N-alkyl-N-heterocyclylaminocarbonyl, heterocyclylalkylcarbonyl, alkylthio and alkylcarbonyloxy moieties may be straight-chain or branched.

Unless indicated otherwise, halogenated substituents preferably carry one to five identical or different halogen atoms. The term halogen denotes in each case fluorine, chlorine, bromine or iodine.

Examples of other meanings are:

$C_1$-$C_4$-alkyl and the alkyl moieties of $C_1$-$C_4$-alkylcarbonyloxy, $C_1$-$C_4$-alkyl-$C_1$-$C_4$-alkoxycarbonylamino, $C_1$-$C_6$-alkyliminooxy-$C_1$-$C_4$-alkyl, $C_1$-$C_4$-alkoxy-$C_1$-$C_4$-alkoxy-$C_1$-$C_4$-alkyl, $C_1$-$C_6$-alkoxy-$C_1$-$C_4$-alkyl, $C_2$-$C_6$-alkenyloxy-$C_1$-$C_4$-alkyl, $C_2$-$C_6$-alkynyloxy-$C_1$-$C_4$-alkyl, $C_1$-$C_6$-haloalkoxy-$C_1$-$C_4$-alkyl, $C_2$-$C_6$-haloalkenyloxy-$C_1$-$C_4$-alkyl, $C_2$-$C_6$-haloalkynyloxy-$C_1$-$C_4$-alkyl, $C_1$-$C_4$-alkoxy-$C_1$-$C_4$-alkoxy-$C_1$-$C_4$alkyl, $C_1$-$C_6$-alkylthio-$C_1$-$C_4$-alkyl, $C_2$-$C_6$-alkenylthio-$C_1$-$C_4$-alkyl, $C_2$-$C_6$-alkynylthio-$C_1$-$C_4$alkyl, $C_1$-$C_6$-alkylsulfinyl-$C_1$-$C_4$-alkyl, $C_1$-$C_6$-haloalkylsulfinyl-$C_1$-$C_4$-alkyl, $C_1$-$C_6$-alkylsulfonyl-$C_1$-$C_4$-alkyl, $C_1$-$C_6$-haloalkylsulfonyl-$C_1$-$C_4$-alkyl, amino-$C_1$-$C_4$-alkyl, $C_1$-$C_6$-alkylamino-$C_1$-$C_4$-alkyl, di($C_1$-$C_6$-alkyl)amino-$C_1$-$C_4$-alkyl, formyl-amino-$C_1$-$C_4$-alkyl, $C_1$-$C_6$-alkoxycarbonylamino-$C_1$-$C_4$-alkyl, $C_1$-$C_6$-alkylsulfonyl-amino-$C_1$-$C_4$-alkyl, $C_1$-$C_6$-alkylsulfonyl-($C_1$-$C_6$-alkylamino)-$C_1$-$C_4$-alkyl, hydroxy-carbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, aminocarbonyl-$C_1$-$C_4$-alkyl, $C_1$-$C_6$-alkylaminocarbonyl-$C_1$-$C_4$-alkyl, di($C_1$-$C_6$-alkyl)aminocarbonyl-$C_1$-$C_4$-alkyl, [($C_1$-$C_6$-alkyl)aminocarbonylamino]-$C_1$-$C_4$-alkyl, [di($C_1$-$C_6$-alkyl)aminocarbonylamino]-$C_1$-$C_4$-alkyl, $C_1$-$C_6$-alkylcarbonylamino-$C_1$-$C_4$-alkyl, $C_1$-$C_6$-alkylcarbonyl-($C_1$-$C_6$-alkylamino)-$C_1$-$C_4$-alkyl, [($C_1$-$C_6$-alkyl)aminocarbonyloxy]-$C_1$-$C_4$-alkyl, [di($C_1$-$C_6$-alkyl)amino-carbonyloxy]$C_1$-$C_4$-alkyl, {di[di($C_1$-$C_6$-alkyl)amino]carbonyloxy}-$C_1$-$C_4$-alkyl, heterocylyl-$C_1$-$C_4$-alkyl, phenyl-$C_1$-$C_4$-alkyl, phenylcarbonylamino-$C_1$-$C_4$-alkyl, phenyl-$C_1$-$C_4$-alkyl, phenylcarbonyl-$C_1$-$C_4$-alkyl, heteroarylcarbonyl-$C_1$-$C_4$-alkyl, heteroarylcarbonyloxy-$C_1$-$C_4$-alkyl, heteroaryloxycarbonyl-$C_1$-$C_4$-alkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl, and aryl ($C_1$-$C_4$-alkyl): for example methyl, ethyl, n-propyl, 1-methylethyl, n-butyl, 1-methylpropyl, 2-methylpropyl and 1,1-dimethylethyl;

$C_1$-$C_6$-alkyl and the alkyl moieties of $C_1$-$C_6$-cyanoalkyl, $C_1$-$C_6$-alkoxycarbonyl-$C_1$-$C_6$-alkyl, $C_1$-$C_6$-alkylsulfonylamino, $C_1$-$C_6$-alkylsulfonylaminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)amino-carbonyl, N—($C_1$-$C_6$-alkoxy)-N—($C_1$-$C_6$-alkyl)aminocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino) imino-$C_1$-$C_6$-alkyl, N-(di-$C_1$-$C_6$-alkylamino)imino-$C_1$-$C_6$-alkyl, ($C_1$-$C_6$-alkyl)cyanoimino, phenyl-$C_1$-$C_6$-alkyl, phenylcarbonyl-$C_1$-$C_6$-alkyl, N—($C_1$-$C_6$-alkyl)-N-phenylaminocarbonyl, heterocyclyl-$C_1$-$C_6$-alkyl, heterocyclylcarbonyl-$C_1$-$C_6$-alkyl and N—($C_1$-$C_6$-alkyl)-N-heterocyclylaminocarbonyl and ($C_1$-$C_6$)alkylaminothiocarbonyl:

$C_1$-$C_4$-alkyl as mentioned above, and also, for example, n-pentyl, 1-methyl-butyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-butyl, 2-ethylbutyl, 1,1,2-trimethylpropyl, 1-ethyl-1-methylpropyl and 1-ethyl-3-methylpropyl;

$C_1$-$C_4$-alkylcarbonyl: for example methylcarbonyl, ethylcarbonyl, propylcarbonyl, 1-methylethylcarbonyl, butylcarbonyl, 1-Methylpropylcarbonyl, 2-methylpropylcarbonyl or 1,1-dimethylethylcarbonyl;

$C_1$-$C_6$-alkylcarbonyl, and the alkylcarbonyl radicals of $C_1$-$C_6$-alkylcarbonyl-$C_1$-$C_6$-alkyl, $C_1$-$C_6$-alkylcarbonyloxy-$C_1$-$C_6$-alkyl, $C_1$-$C_6$-alkylcarbonylamino-$C_1$-$C_4$-alkyl, phenyl-$C_1$-$C_6$-alkylcarbonyl and heterocyclyl-$C_1$-$C_6$-alkylcarbonyl, $C_1$-$C_6$-alkylcarbonyl-($C_1$-$C_6$-alkylamino)-$C_1$-$C_4$-alkyl:

$C_1$-$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethyl-butylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_3$-$C_6$-cycloalkyl and the cycloalkyl moieties of $C_3$-$C_6$-cycloalkylcarbonyl: monocyclic saturated hydrocarbon having 3 to 6 ring members, such as cyclopropyl, cyclobutyl, cyclopentyl and cyclohexyl;

$C_3$-$C_6$-cycloalkenyl: for example 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkenyl and the alkenyl moieties of $C_3$-$C_6$-alkenyloxycarbonyl, $C_3$-$C_6$-alkenylaminocarbonyl, N—($C_3$-$C_6$-alkenyl)-N—($C_1$-$C_6$-alkyl)aminocarbonyl and N—($C_3$-$C_6$-alkenyl)-N—($C_1$-$C_6$-alkoxy)aminocarbonyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-ethyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and the alkenyl moieties of $C_2$-$C_6$-alkenylcarbonyl, $C_2$-$C_6$-alkenyloxy-$C_1$-$C_4$-alkyl, $C_2$-$C_6$-alkenylthio-$C_1$-$C_4$-alkyl, phenyl-$C_2$-$C_4$-alkenyl, heteroaryl-$C_2$-$C_4$-alkenyl: $C_3$-$C_6$-alkenyl as mentioned above, and also ethenyl;

$C_3$-$C_6$-alkynyl and the alkynyl moieties of $C_3$-$C_6$-alkynyloxycarbonyl, $C_3$-$C_6$-alkynyl-aminocarbonyl, N—($C_3$-$C_6$-alkynyl)-N—($C_1$-$C_6$-alkyl)aminocarbonyl, N—($C_3$-$C_6$-alkynyl)-N—($C_1$-$C_6$-alkoxy)aminocarbonyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl and the alkynyl moieties of $C_2$-$C_6$-alkynylcarbonyl, $C_2$-$C_2$-alkynyloxy-$C_1$-$C_4$-alkyl, $C_2$-$C_6$-alkynylthio-$C_1$-$C_4$-alkyl, phenyl-$C_2$-$C_4$-alkynyl, heteroaryl-$C_2$-$C_4$-alkynyl: $C_3$-$C_6$-alkynyl as mentioned above, and also ethynyl;

$C_1$-$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_1$-$C_4$-hydroxyalkyl and the $C_1$-$C_4$-hydroxyalkyl moieties of phenyl-$C_1$-$C_4$-hydroxyalkyl, heteroaryl-$C_1$-$C_4$-hydroxyalkyl: for example hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl and 2-hydroxymethylprop-2-yl, 1,2-dihydroxyethyl, 1,2-dihydroxyprop-3-yl, 2,3-dihydroxyprop-3-yl, 1,2-dihydroxyprop-2-yl, 1,2-dihydroxybut-4-yl, 2,3-dihydroxybut-4-yl, 3,4-dihydroxybut-4-yl, 1,2-dihydroxybut-2-yl, 1,2-dihydroxybut-3-yl, 2,3-dihydroxybut-3-yl, 1,2-dihydroxy-2-methylprop-3-yl, 2,3-dihydroxy-2-methylprop-3-yl;

$C_1$-$C_6$-hydroxyalkyl: $C_1$-$C_4$-hydroxyalkyl as mentioned above, and also, for example, 1-hydroxypent-5-yl, 2-hydroxypent-5-yl, 3-hydroxypent-5-yl, 4-hydroxypent-5-yl, 5-hydroxypent-5-yl, 1-hydroxypent-4-yl, 2-hydroxypent-4-yl, 3-hydroxypent-4-yl, 4-hydroxypent-4-yl, 1-hydroxypent-3-yl, 2-hydroxypent-3-yl, 3-hydroxypent-3-yl, 1-hydroxy-2-methylbut-3-yl, 2-hydroxy-2-methylbut-3-yl, 3-hydroxy-2-methylbut-3-yl, 1-hydroxy-2-methylbut-4-yl, 2-hydroxy-2-methylbut-4-yl, 3-hydroxy-2-methylbut-4-yl, 4-hydroxy-2-methylbut-4-yl, 1-hydroxy-3-methylbut-4-yl, 2-hydroxy-3-methylbut-4-yl, 3-hydroxy-3-methylbut-4-yl, 4-hydroxy-3-methylbut-4-yl, 1-hydroxyhex-6-yl, 2-hydroxyhex-6-yl, 3-hydroxyhex-6-yl, 4-hydroxyhex-6-yl, 5-hydroxyhex-6-yl, 6-hydroxyhex-6-yl, 1-hydroxy-2-methylpent-5-yl, 2-hydroxy-2-methylpent-5-yl, 3-hydroxy-2-methylpent-5-yl, 4-hydroxy-2-methylpent-5-yl, 5-hydroxy-2-methylpent-5-yl, 1-hydroxy-3-methylpent-5-yl, 2-hydroxy-3-methylpent-5-yl, 3-hydroxy-3-methylpent-5-yl, 4-hydroxy-3-methylpent-5-yl, 5-hydroxy-3-methylpent-5-yl, 1-hydroxy-4-methylpent-5-yl, 2-hydroxy-4-methylpent-5-yl, 3-hydroxy-4-methylpent-5-yl, 4-hydroxy-4-methylpent-5-yl, 5-hydroxy-4-methylpent-5-yl, 1-hydroxy-5-methylpent-5-yl, 2-hydroxy-5-methylpent-5-yl, 3-hydroxy-5-methylpent-5-yl, 4-hydroxy-5-methylpent-5-yl, 5-hydroxy-5-methylpent-5-yl, 1-hydroxy-2,3-dimethylbut-4-yl, 2-hydroxy-2,3-dimethylbut-4-yl, 3-hydroxy-2,3-dimethylbut-4-yl, 4-hydroxy-2,3-dimethylbut-4-yl, 1,2-dihydroxypent-5-yl, 2,3-dihydroxypent-5-yl, 3,4-dihydroxypent-5-yl, 4,5-dihydroxypent-5-yl, 1,2-dihydroxypent-4-yl, 2,3-dihydroxypent-4-yl, 3,4-dihydroxypent-4-yl, 4,5-dihydroxypent-4-yl, 1,2-dihydroxypent-3-yl, 2,3-dihydroxypent-3-yl, 1,2-dihydroxy-2-methylbut-3-yl, 2,3-dihydroxy-2-methylbut-3-yl, 3,4-dihydroxy-2-methylbut-3-yl, 2-hydroxy-2-hydroxymethylbut-3-yl, 1,2-dihydroxy-2-methylbut-4-yl, 2,3-dihydroxy-2-methylbut-4-yl, 3,4-dihydroxy-2-methylbut-4-yl, 1,2-dihydroxy-3-methylbut-4-yl, 2,3-dihydroxy-3-methylbut-4-yl, 3,4-dihydroxy-3-methylbut-4-yl, 3-hydroxy-3-hydroxymethylbut-4-yl, 1,2-dihydroxyhex-6-yl, 2,3-di-hydroxyhex-6-yl, 3,4-dihydroxyhex-6-yl, 4,5-dihydroxyhex-6-yl, 5,6-dihydroxyhex-6-yl, 1,2-dihydroxy-2-methylpent-5-yl, 2,3-dihydroxy-2-methylpent-5-yl, 3,4-di-hydroxy-2-methylpent-5-yl, 4,5-dihydroxy-2-methylpent-5-yl, 2-hydroxy-2-hydroxymethylpent-5-yl, 1,2-dihydroxy-3-methylpent-5-yl, 2,3-dihydroxy-3-methylpent-5-yl, 3,4-dihydroxy-3-methylpent-5-yl, 4,5-dihydroxy-3-methylpent-5-yl, 3-hydroxy-3-hydroxymethylpent-5-yl, 1,2-dihydroxy-4-methylpent-5-yl, 2,3-dihydroxy-4-methylpent-5-yl, 3,4-dihydroxy-4-methylpent-5-yl, 4,5-dihydroxy-4-methylpent-5-yl, 4-hydroxy-4-hydroxymethylpent-5-yl, 1,2-dihydroxy-5-methylpent-5-yl, 2,3-di-hydroxy-5-methylpent-5-yl, 3,4-dihydroxy-5-methylpent-5-yl, 4,5-dihydroxy-5-methylpent-5-yl, 5-hydroxy-5-hydroxymethylpent-5-yl, 1,2-dihydroxy-2,3-dimethylbut-4-yl, 2,3-dihydroxy-2,3-dimethylbut-4-yl, 3,4-dihydroxy-2,3-dimethylbut-4-yl, 2-hydroxy-2- hydroxymethyl-3-methylbut-4-yl, 3-hydroxy-3-hydroxymethyl-2-methylbut-4-yl;

$C_1$-$C_4$-haloalkyl and the haloalkyl moieties of phenyl-$C_1$-$C_4$-haloalkyl, heteroaryl-$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2-tetrafluoroethyl and 1-trifluoromethyl-1,2,2,2-tetrafluoroethyl;

$C_1$-$C_6$-haloalkyl and the haloalkyl moieties of $C_1$-$C_6$-haloalkylsulfonylamino, $C_1$-$C_6$-haloalkyl-$C_1$-$C_4$-thioalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and tridecafluorohexyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_2$-$C_6$-haloalkenyl and the $C_2$-$C_6$-haloalkenyl moieties of $C_2$-$C_6$-haloalkenyloxy-$C_1$-$C_4$-alkyl, $C_2$-$C_6$-haloalkenyl-$C_1$-$C_4$-thioalkyl, phenyl-$C_2$-$C_4$-haloalkenyl, heteroaryl-$C_2$-$C_4$-haloalkenyl: a $C_2$-$C_6$-alkenyl radical as mentioned above which is partially or fully substituted by fluorine, chlorine, bromine and/or iodine, for example 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromovinyl, 2-bromoallyl, 3-bromoallyl, 2,3-dibromoallyl, 3,3-dibromoallyl, 2,3,3-tribromoallyl or 2,3-dibromobut-2-enyl;

$C_2$-$C_6$-cyanoalkenyl: for example 2-cyanovinyl, 2-cyanoallyl, 3-cyanoallyl, 2,3-dicyanoallyl, 3,3-dicyanoallyl, 2,3,3-tricyanoallyl, 2,3-dicyanobut-2-enyl;

$C_2$-$C_6$-hydroxyalkenyl and the hydroxyl moieties of phenyl-$C_1$-$C_4$-hydroxyalkenyl, heteroaryl-$C_1$-$C_4$-hydroxyalkenyl: for example 2-hydroxyvinyl, 2-hydroxyallyl, 3-hydroxyallyl, 2,3-dihydroxyallyl, 3,3-dihydroxyallyl, 2,3,3-trihydroxyallyl, 2,3-dihydroxybut-2-enyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_2$-$C_6$-haloalkynyl and the $C_2$-$C_6$-haloalkynyl moieties of $C_2$-$C_6$-haloalkynyloxy-$C_1$-$C_4$-alkyl, $C_2$-$C_6$-haloalkynyl-$C_1$-$C_4$-thioalkyl, phenyl-$C_2$-$C_4$-haloalkynyl, heteroaryl-$C_2$-$C_4$-haloalkynyl: a $C_2$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_2$-$C_6$-cyanoalkynyl: for example 1,1-dicyanoprop-2-yn-1-yl, 3-cyanoprop-2-yn-1-yl, 4-cyanobut-2-yn-1-yl, 1,1-dicyanobut-2-yn-1-yl, 4-cyanobut-3-yn-1-yl, 5-cyanopent-3-yn-1-yl, 5-cyanopent-4-yn-1-yl, 6-cyanohex-4-yn-1-yl or 6-cyanohex-5-yn-1-yl;

$C_2$-$C_6$-hydroxyalkynyl and the hydroxy moieties of phenyl-$C_2$-$C_4$-hydroxyalkynyl: for example 1,1-dihydroxyprop-2-yn-1-yl, 3-hydroxyprop-2-yn-1-yl, 4-hydroxybut-2-yn-1-yl, 1,1-dihydroxybut-2-yn-1-yl, 4-hydroxybut-3-yn-1-yl, 5-hydroxypent-3-yn-1-yl, 5-hydroxypent-4-yn-1-yl, 6-hydroxyhex-4-yn-1-yl or 6-hydroxyhex-5-yn-1-yl;

$C_1$-$C_6$-alkylsulfinyl ($C_1$-$C_6$-alkyl-S(=O)—) and the $C_1$-$C_6$-alkylsulfinyl moieties of $C_1$-$C_6$-alkylsulfinyl-$C_1$-$C_4$-alkyl: for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-haloalkylsulfinyl and the $C_1$-$C_6$-haloalkylsulfinyl moieties of $C_1$-$C_6$-haloalkylsulfinyl-$C_1$-$C_4$-alkyl: a $C_1$-$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-thfluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and tridecafluorohexylsulfinyl;

$C_1$-$C_6$-alkylsulfonyl ($C_1$-$C_6$-alkyl-S(O)$_2$—) and the $C_1$-$C_6$-alkylsulfonyl moieties of $C_1$-$C_6$-alkylsulfonyl-$C_1$-$C_4$-alkyl, $C_1$-$C_6$-alkylsulfonylamino, $C_1$-$C_6$-alkyl-sulfonyl-amino-$C_1$-$C_4$-alkyl, $C_1$-$C_6$-alkylsulfonyl-($C_1$-$C_6$-alkylamino)-$C_1$-$C_4$-alkyl: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$-$C_6$-haloalkylsulfonyl and the $C_1$-$C_6$-haloalkylsulfonyl moieties of $C_1$-$C_6$-haloalkylsulfonyl-$C_1$-$C_4$-alkyl, $C_1$-$C_6$-haloalkylsulfonylamino: a $C_1$-$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and tridecafluorohexylsulfonyl;

$C_1$-$C_4$-alkoxy and also all the alkoxy moieties of hydroxycarbonyl-$C_1$-$C_4$-alkoxy, $C_1$-$C_4$-alkoxycarbonyl-$C_1$-$C_4$-alkoxy, $C_1$-$C_4$-alkoxy-$C_1$-$C_4$-alkoxy-$C_1$-$C_4$-alkyl and $C_1$-$C_4$-alkyl-$C_1$-$C_4$-alkoxycarbonylamino: for example methoxy, ethoxy, propoxy, 1-methylethoxy, butoxy, 1-methylpropoxy, 2-methylpropoxy and 1,1-dimethylethoxy;

$C_1$-$C_6$-alkoxy and the alkoxy moieties of hydroxycarbon-$C_1$-$C_6$-alkoxy, $C_1$-$C_6$-alkoxycarbonyl-$C_1$-$C_6$-alkoxy, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl and $C_1$-$C_6$-alkoxyimino-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy,1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichioropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy and the $C_1$-$C_6$-haloalkoxy moieties of $C_1$-$C_6$-haloalkoxy-$C_1$-$C_4$-alkyl, $C_1$-$C_6$-haloalkoxycarbonyl-$C_1$-$C_4$-alkyl: $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkoxy-$C_1$-$C_4$-alkyl and the $C_1$-$C_6$-alkoxy-$C_1$-$C_4$-alkyl moieties of $C_1$-$C_6$-alkoxy-$C_1$-$C_4$-alkoxy-$C_1$-$C_4$-alkyl: $C_1$-$C_4$-alkyl which is substituted by $C_1$-$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methyl-propoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)-ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)-propyl, 3-(methoxy)propyl, 3-(ethoxy)propyl, 3-(propoxy)propyl, 3-(1-methylethoxy)-propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methyl-propoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)-butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropm)butyl, 4-(2-methylpropoxy)butyl and 4-(1,1-dimethylethoxy)butyl;

$C_1$-$C_4$-alkoxycarbonyl and the alkoxycarbonyl moieties of $C_1$-$C_4$-alkoxycarbonyl-$C_1$-$C_4$-aralkoxy, $C_1$-$C_4$-alkoxy-$C_1$-$C_4$-alkoxycarbonyl and di-($C_1$-$C_4$-alkyl)amino-$C_1$-$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$-$C_6$-alkoxycarbonyl and the alkoxycarbonyl moieties of $C_1$-$C_6$-alkoxycarbonyl-$C_1$-$C_6$-alkoxy and $C_1$-$C_6$-alkoxycarbonylamino-$C_1$-$C_4$-alkyl: $C_1$-$C_4$-alkoxycarbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$-$C_4$-alkylthio and the $C_1$-$C_4$-alkylthio moieties of $C_1$-$C_6$-haloalkyl-$C_1$-$C_4$-thioalkyl, $C_2$-$C_6$-haloalkenyl-$C_1$-$C_4$-thioalkyl; $C_2$-$C_6$-haloalkynyl-$C_1$-$C_4$-thioalkyl: for example methylthio, ethylthio, propylthio, 1-methylethylthio, butylthio, 1-methylpropylthio, 2-methylpropylthio and 1,1-dimethylethylthio;

$C_1$-$C_6$-alkylthio and the $C_1$-$C_6$-alkylthio moieties of $C_1$-$C_6$-alkylthio-$C_1$-$C_4$-alkyl: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylamino and the $C_1$-$C_6$-alkylamino radicals of N—($C_1$-$C_6$-alkylamino)imino-$C_1$-$C_6$-alkyl, $C_1$-$C_6$-alkylamino-$C_1$-$C_4$-alkyl, $C_1$-$C_6$-alkylsulfonyl-($C_1$-$C_6$-alkylamino)-$C_1$-$C_4$-alkyl, $C_1$-$C_6$-alkylcarbonyl-($C_1$-$C_6$-alkylamino)-$C_1$-$C_4$-alkyl and [$C_1$-$C_6$-alkyl)amino] cyanoimino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di-($C_1$-$C_4$-alkyl)amino: for example N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)-amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propyl-amino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di-($C_1$-$C_6$-alkylamino and the dialkylamino radicals of N-(di-$C_1$-$C_6$-alkylamino)imino-$C_1$-$C_6$-alkyl, di($C_1$-$C_6$-alkyl)amino-$C_1$-$C_4$-alkyl, [di($C_1$-$C_6$-alkyl)aminocarbonyloxy]-$C_1$-$C_4$-alkyl, {di[di($C_1$-$C_6$-alkyl)amino]carbonyloxy}-$C_1$-$C_4$-alkyl and [di($C_1$-$C_6$-alkyl)amino] cyanoimino: di-($C_1$-$C_4$-alkyl)amino as mentioned above, and also, for example, N,N-dipentylamino, N,N-dihexylamino, N-methyl-N-pentylamino, N-ethyl-N-pentylamino, N-methyl-N-hexylamino and N-ethyl-N-hexylamino;

($C_1$-$C_4$-alkylamino)carbonyl and the ($C_1$-$C_4$-alkylamino) carbonyl moieties of ($C_1$-$C_4$-alkylamino)carbonylamino: for example methylaminocarbonyl, ethylaminocarbonyl, propylaminocarbonyl, 1-methylethylaminocarbonyl, butylaminocarbonyl, 1-methylpropylaminocarbonyl, 2-methylproylaminocarbonyl or 1,1-dimethylethylaminocarbonyl;

($C_1$-$C_4$-alkylamino)thiocarbonyl and also the ($C_1$-$C_4$-alkylamino)thiocarbonyl moieties of ($C_1$-$C_4$-alkylamino) thiocarbonylamino: for example methylaminothiocarbonyl, ethylaminothiocarbonyl, propylaminothiocarbonyl, 1-methylethylaminothiocarbonyl, butylaminothiocarbonyl, 1-methylpropylaminothiocarbonyl, 2-methylpropylaminothiocarbonyl or 1,1-dimethylethylaminothiocarbonyl;

di-($C_1$-$C_4$-alkyl)aminocarbonyl and also di-($C_1$-$C_4$-alkyl) aminocarbonyl moieties of di-($C_1$-$C_4$-alkyl)aminocarbonylamino: for example N,N-dimethylaminocarbonyl, N,N-diethylaminocarbonyl, N,N-di-(1-methylethyl) aminocarbonyl, N,N-dipropylaminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)

aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

($C_1$-$C_6$-alkylamino)carbonyl and also the ($C_1$-$C_6$-alkylamino)carbonyl moieties of ($C_1$-$C_6$-alkylamino)carbonylamino, ($C_1$-$C_6$-alkylamino)carbonyloxy-$C_1$-$C_4$-alkyl, $C_1$-$C_6$-alkylaminocarbonyl-$C_1$-$C_4$-alkyl and [($C_1$-$C_6$-alkyl)aminocarbonylamino]-$C_1$-$C_4$-alkyl: ($C_1$-$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di-($C_1$-$C_6$-alkyl)aminocarbonyl and also the di-($C_1$-$C_6$-alkyl)aminocarbonyl moieties of di-($C_1$-$C_6$-alkyl)aminocarbonylamino, di($C_1$-$C_6$-alkyl)aminocarbonyl-$C_1$-$C_4$-alkyl and [di($C_1$-$C_6$-alkyl)aminocarbonylamino]-$C_1$-$C_4$-alkyl: di-($C_1$-$C_4$-alkyl)aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)-aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)-aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di-($C_1$-$C_6$-alkyl)aminothiocarbonyl: for example N,N-dimethylaminothiocarbonyl, N,N-diethylaminothiocarbonyl, N,N-di-(1-methylethyl)aminothiocarbonyl, N,N-dipropylaminothiocarbonyl, N,N-dibutylaminothiocarbonyl, N,N-di-(1-methylpropyl)aminothiocarbonyl, N,N-di-(2-methylpropyl)aminothiocarbonyl, N,N-di-(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)-aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylamino-thiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)-aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N- hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)-aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)-aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)-aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)-aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

three- to six-membered heterocyclyl and also the three- to six-membered heterocyclyl moieties of three- to six-membered heterocyclyl-$C_1$-$C_4$-alkyl: monocyclic saturated or partially unsaturated hydrocarbons having three to six ring members as mentioned above which, in addition to carbon atoms, may contain one to four nitrogen atoms, or one to three nitrogen atoms and one oxygen or sulfur atom, or one to three oxygen atoms, or one to three sulfur atoms, and which may be attached via a carbon atom or a nitrogen atom.

for example 2-oxiranyl, 2-oxetanyl, 3-oxetanyl, 2-aziridinyl, 3-thietanyl, 1-azetidinyl, 2-azetidinyl, for example 2-tetrahydrofuranyl, 3-tetrahydrofuranyl, 2-tetrahydrothienyl, 3-tetra-hydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 1,2,3,4-tetrazolidin-5-yl, for example 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl, 1,2,3,4-tetrazolidin-1-yl, for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-di-hydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl, for example 4,5-dihydropyrrol-1-yl, 2,5-dihydropyrrol-1-yl, 4,5-dihydroisoxazol-2-yl, 2,3-dihydroisoxazol-1-yl, 4,5-dihydroisothiazol-1-yl, 2,3-dihydroisothiazol-1-yl, 2,3-dihydropyrazol-1-yl, 4,5-dihydropyrazol-1-yl, 3,4-dihydropyrazol-1-yl, 2,3-dihydroimidazol-1-yl, 4,5-dihydroimidazol-1-yl, 2,5-dihydroimidazol-1-yl, 2,3-dihydrooxazol-2-yl, 3,4-dihydrooxazol-2-yl, 2,3-dihydrothiazol-2-yl, 3,4-dihydrothiazol-2-yl, for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-3-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5- hexahydrotriazin-2-yl, 1,2,4-hexahydrotriazin-3-yl, tetrahydro-1,3-oxazin-2-yl, tetrahydro-1,3-oxazin-6-yl, 2-morpholinyl, 3-morpholinyl, 1,3,5-trioxan-2-yl, for example 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl, for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

aryl and the aryl moiety of aryl-($C_1$-$C_6$-alkyl): a monocyclic to tricyclic aromatic carbocycle having 6 to 14 ring members, such as, for example, phenyl, naphthyl and anthracenyl;

heteroaryl and the heteroaryl radicals in heteroaryl-$C_1$-$C_4$-alkyl, heteroaryl-$C_1$-$C_4$-alkyl, heteroaryl-$C_2$-$C_4$-alkenyl, heteroaryl-$C_2$-$C_4$-alkynyl, heteroaryl-$C_1$-$C_4$-haloalkyl, heteroaryl-$C_2$-$C_4$-haloalkenyl, heteroaryl-$C_2$-$C_4$-haloalkynyl, heteroaryl-$C_1$-$C_4$-hydroxyalkyl, heteroaryl-$C_2$-$C_4$-hydroxyalkenyl, heteroaryl-$C_2$-$C_4$-hydroxyalkynyl, heteroarylcarbonyl-$C_1$-$C_4$-alkyl, heteroarylcarbonyloxy-$C_1$-$C_4$-alkyl, heteroaryloxycarbonyl-$C_1$-$C_4$-alkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl:

mono- or bicyclic aromatic heteroaryl having 5 to 10 ring members which, in addition to carbon atoms, contains 1 to 4 nitrogen atoms or 1 to 3 nitrogen atoms and one oxygen or one sulfur atom or one oxygen or one sulfur atom, for example monocycles, such as furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazol-2-yl, imidazol-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl), tetrazol-5-yl, pyridyl (for example pyridin-2-yl, pyridin-3-yl, pyridin-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl), tetrazinyl (for example 1,2,4,5-tetrazin-3-yl); and also bicycles, such as the benzo-fused derivatives of the abovementioned monocycles, for example quinolinyl, isoquinolinyl, indolyl, benzothienyl, benzofuranyl, benzoxazolyl, benzothiazolyl, benzoisothiazolyl, benzimidazolyl, benzopyrazolyl, benzothiadiazolyl, benzotriazolyl.

5- or 6-membered heteroaryl having one to four nitrogen atoms or one to three nitrogen atoms and one oxygen or sulfur atom or having one oxygen or sulfur atom: for example aromatic 5-membered heterocycles which are attached via a carbon atom and which, in addition to carbon atoms, may contain one to four nitrogen atoms or one to three nitrogen atoms and one sulfur or oxygen atom or one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; for example aromatic 6-membered heterocycles which are attached via a carbon atom and which, in addition to carbon atoms, may contain one to four, preferably one to three, nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

All phenyl and aryl rings or heterocyclyl and heteroaryl radicals and all phenyl components in phenyl-$C_1$-$C_6$-alkyl, phenylcarbonyl, phenylcarbonyl-$C_1$-$C_6$-alkyl, phenylcarbonylamino-$C_1$-$C_4$-alkyl, phenoxycarbonyl, phenylaminocarbonyl, phenylsulfonylaminocarbonyl, N—($C_1$-$C_6$-alkyl)-N-phenylaminocarbonyl and phenyl-$C_1$-$C_6$-alkylcarbonyl, all aryl components in aryl($C_1$-$C_4$-alkyl), all heteroaryl components in mono- or bicyclic heteroaryl and all heterocyclyl components in heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-heterocyclylaminocarbonyl and heterocyclyl-$C_1$-$C_6$-alkylcarbonyl are, unless indicated otherwise, preferably unsubstituted or carry one to three halogen atoms and/or one nitro group, one cyano radical and/or one or two methyl, trifluoromethyl, methoxy or trifluoromethoxy substituents.

In a particular embodiment, the variables of the heteroaroyl-substituted serineamides of the formula (I) are as defined below, these definitions being, both on their own and in combination with one another, preferred embodiments of the compounds of the formula (I):

Preference is given to the heteroaroyl-substituted serineamides of the formula (I) in which A is 5-membered heteroaryl having one to four nitrogen atoms or one to three nitrogen atoms and one oxygen or sulfur atom or having one oxygen or sulfur atom;
particularly preferably 5-membered heteroaryl selected from the group consisting of thienyl, furyl, pyrazolyl, imidazolyl, thiazolyl and oxazolyl;
especially preferably 5-membered heteroaryl selected from the group consisting of thienyl, furyl, pyrazolyl and imidazolyl;
where the heteroaryl radicals mentioned are substituted by a $C_1$-$C_6$-haloalkyl radical, preferably in 2-position by a $C_1$-$C_6$-haloalkyl radical, and may carry 1 to 3 radicals from the group consisting of halogen, cyano, $C_1$-$C_6$-alkyl, $C_3$-$C_6$-cycloalkyl, $C_1$-$C_6$-alkoxy, $C_1$-$C_6$-haloalkoxy and $C_1$-$C_6$-alkoxy-$C_1$-$C_4$-alkyl.

Preference is also given to the heteroaroyl-substituted serineamides of the formula (I) in which A is 5-membered heteroaryl having one to four nitrogen atoms or one to three nitrogen atoms and one oxygen or sulfur atom or having one oxygen or sulfur atom;
particularly preferably 5-membered heteroaryl selected from the group consisting of thienyl, furyl, pyrazolyl, imidazolyl, thiazolyl and oxazolyl;
especially preferably 5-membered heteroaryl selected from the group consisting of thienyl, furyl, pyrazolyl and imidazolyl;
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is also given to the heteroaroyl-substituted serineamides of the formula (I) in which A is a 5-membered heteroaryl having one to four nitrogen atoms or one to three nitrogen atoms and one oxygen or sulfur atom or having one oxygen atom;
particularly preferably 5-membered heteroaryl selected from the group consisting of furyl, pyrazolyl, imidazolyl, thiazolyl and oxazolyl,
especially preferably 5-membered heteroaryl selected from the group consisting of furyl, pyrazolyl and imidazolyl;
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is also given to the heteroaroyl-substituted serineamides of the formula (I) in which A is 6-membered heteroaryl having one to four nitrogen atoms;
particularly preferably pyridyl or pyrimidyl,
especially preferably pyrimidyl,
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is also given to the heteroaroyl-substituted serineamides of the formula (I), in which A is 5- or 6-membered heteroaryl having one to four nitrogen atoms, or having one to three nitrogen atoms and one oxygen or sulfur atom, or having one oxygen or sulfur atom,
which are substituted by a $C_1$-$C_6$-haloalkyl radical, preferably in the 2-position by a $C_1$-$C_6$-haloalkyl radical, and may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is also given to the heteroaroyl-substituted serineamides of the formula (I) in which A is 5- or 6-membered heteroaryl selected from the group consisting of pyrrolyl, thienyl, furyl, pyrazolyl, imidazolyl, thiazolyl, oxazolyl, tetrazolyl, pyridyl and pyrimidinyl,
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;
particularly preferably 5- or 6-membered heteroaryl selected from the group consisting of thienyl, furyl, pyrazolyl, imidazolyl, thiazolyl, oxazolyl and pyridyl;
where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;
especially preferably 5-membered heteroaryl selected from the group consisting of thienyl, furyl, pyrazolyl, imidazolyl, thiazolyl and oxazolyl,
where the heteroaryl radicals mentioned may be partially halogenated and/or may carry 1 to 2 radicals from the group consisting of $C_1$-$C_6$-alkyl and $C_1$-$C_4$-haloalkyl;
most preferably 5-membered heteroaryl selected from the group consisting of thienyl, furyl, pyrazolyl and imidazolyl;
where the heteroaryl radicals mentioned may be partially halogenated and/or may carry 1 to 2 radicals from the group consisting of $C_1$-$C_6$-alkyl and $C_1$-$C_4$-haloalkyl.

Preference is also given to the heteroaroyl-substituted serineamides of the formula (I) in which A is 5- or 6-membered heteroaryl selected from the group consisting of pyrrolyl, furyl, pyrazolyl, imidazolyl, thiazolyl, oxazolyl, tetrazolyl, pyridyl and pyrimidinyl,
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl,
particularly preferably 5- or 6-membered heteroaryl selected from the group consisting of furyl, pyrazolyl, imidazolyl, thiazolyl, oxazolyl and pyridyl,
where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;
especially preferably 5-membered heteroaryl selected from the group consisting of furyl, pyrazolyl, imidazolyl, thiazolyl and oxazolyl,
where the heteroaryl radicals mentioned may be partially halogenated and/or may carry 1 to 2 radicals from the group consisting of $C_1$-$C_6$-alkyl and $C_1$-$C_4$-haloalkyl;
most preferably 5-membered heteroaryl selected from the group consisting of furyl, pyrazolyl and imidazolyl,
where the heteroaryl radicals mentioned may be partially halogenated and/or may carry 1 to 2 radicals from the group consisting of $C_1$-$C_6$-alkyl and $C_1$-$C_4$-haloalkyl.

Preference is also given to the heteroaroyl-substituted serineamides of the formula (I) in which A is 5- or 6-membered heteroaryl which is attached via carbon and selected from the group consisting of A1 to A14

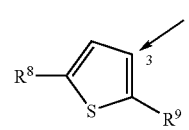

A1

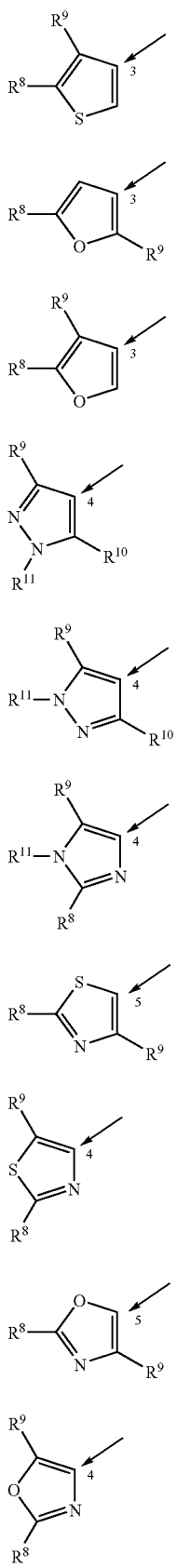

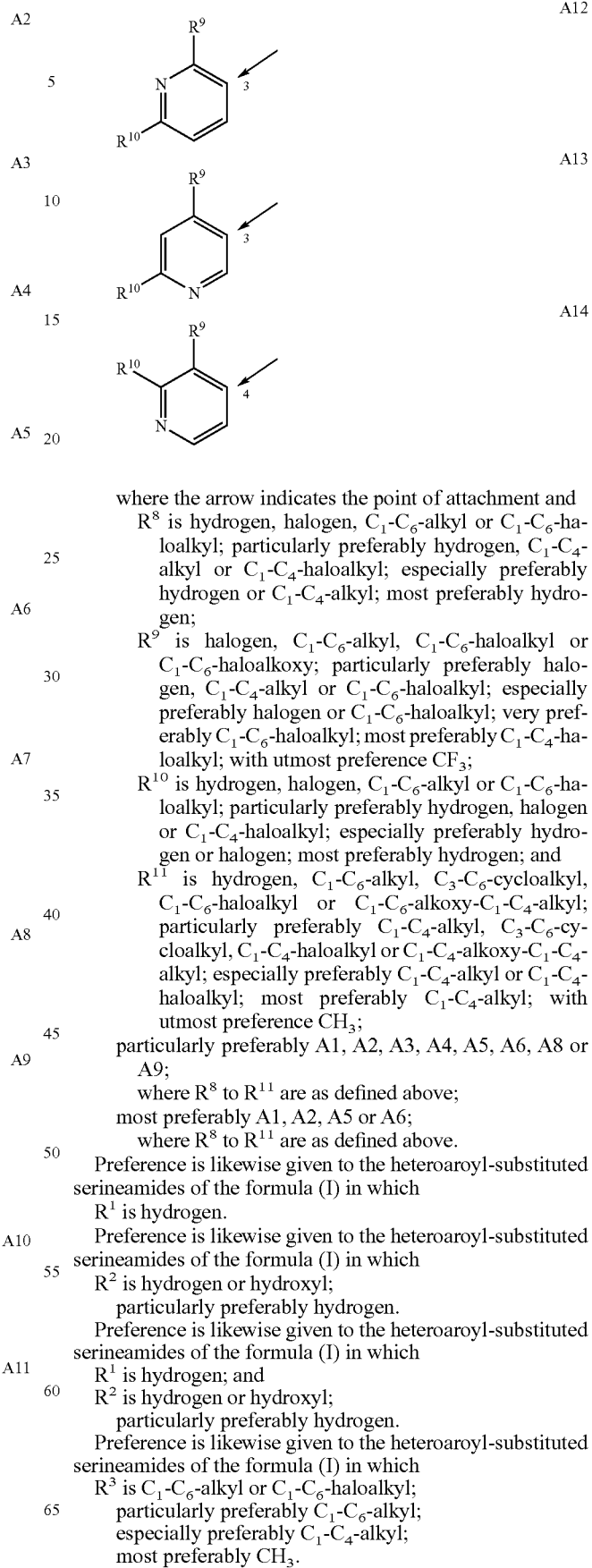

where the arrow indicates the point of attachment and
R$^8$ is hydrogen, halogen, C$_1$-C$_6$-alkyl or C$_1$-C$_6$-haloalkyl; particularly preferably hydrogen, C$_1$-C$_4$-alkyl or C$_1$-C$_4$-haloalkyl; especially preferably hydrogen or C$_1$-C$_4$-alkyl; most preferably hydrogen;

R$^9$ is halogen, C$_1$-C$_6$-alkyl, C$_1$-C$_6$-haloalkyl or C$_1$-C$_6$-haloalkoxy; particularly preferably halogen, C$_1$-C$_4$-alkyl or C$_1$-C$_6$-haloalkyl; especially preferably halogen or C$_1$-C$_6$-haloalkyl; very preferably C$_1$-C$_6$-haloalkyl; most preferably C$_1$-C$_4$-haloalkyl; with utmost preference CF$_3$;

R$^{10}$ is hydrogen, halogen, C$_1$-C$_6$-alkyl or C$_1$-C$_6$-haloalkyl; particularly preferably hydrogen, halogen or C$_1$-C$_4$-haloalkyl; especially preferably hydrogen or halogen; most preferably hydrogen; and R$^{11}$ is hydrogen, C$_1$-C$_6$-alkyl, C$_3$-C$_6$-cycloalkyl, C$_1$-C$_6$-haloalkyl or C$_1$-C$_6$-alkoxy-C$_1$-C$_4$-alkyl; particularly preferably C$_1$-C$_4$-alkyl, C$_3$-C$_6$-cycloalkyl, C$_1$-C$_4$-haloalkyl or C$_1$-C$_4$-alkoxy-C$_1$-C$_4$-alkyl; especially preferably C$_1$-C$_4$-alkyl or C$_1$-C$_4$-haloalkyl; most preferably C$_1$-C$_4$-alkyl; with utmost preference CH$_3$;

particularly preferably A1, A2, A3, A4, A5, A6, A8 or A9;
where R$^8$ to R$^{11}$ are as defined above;
most preferably A1, A2, A5 or A6;
where R$^8$ to R$^{11}$ are as defined above.

Preference is likewise given to the heteroaroyl-substituted serineamides of the formula (I) in which
R$^1$ is hydrogen.

Preference is likewise given to the heteroaroyl-substituted serineamides of the formula (I) in which
R$^2$ is hydrogen or hydroxyl;
particularly preferably hydrogen.

Preference is likewise given to the heteroaroyl-substituted serineamides of the formula (I) in which
R$^1$ is hydrogen; and
R$^2$ is hydrogen or hydroxyl;
particularly preferably hydrogen.

Preference is likewise given to the heteroaroyl-substituted serineamides of the formula (I) in which
R$^3$ is C$_1$-C$_6$-alkyl or C$_1$-C$_6$-haloalkyl;
particularly preferably C$_1$-C$_6$-alkyl;
especially preferably C$_1$-C$_4$-alkyl;
most preferably CH$_3$.

Preference is likewise given to the heteroaroyl-substituted serineamides of the formula (I), in which R$^4$ is hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_3$-$C_6$-cycloalkylcarbonyl, $C_1$-$C_6$-alkoxycarbonyl, $C_1$-$C_6$-alkylaminocarbonyl, $C_1$-$C_6$-alkylsulfonylaminocarbonyl, ($C_1$-$C_6$)alkylaminothiocarbonyl, di-($C_1$-$C_6$-alkyl)aminocarbonyl, N—($C_1$-$C_6$-alkoxy)-N—($C_1$-$C_6$-alkyl)aminocarbonyl, di-($C_1$-$C_6$-alkyl)-aminothiocarbonyl, $C_1$-$C_6$-alkoxyimino-$C_1$-$C_6$-alkyl, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di-($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl, or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenylsulfonylaminocarbonyl or phenyl-$C_1$-$C_6$-alkylcarbonyl, where the phenyl ring may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or

SO$_2$R$^7$;

particularly preferably hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_1$-$C_6$-alkoxycarbonyl, sulfonylaminocarbonyl, ($C_1$-$C_6$)alkylaminocarbonyl, di-($C_1$-$C_6$-alkyl)amino-carbonyl, N—($C_1$-$C_6$-alkoxy)-N—($C_1$-$C_6$-alkyl)aminocarbonyl, ($C_1$-$C_6$) alkylaminothiocarbonyl or di-($C_1$-$C_6$-alkyl) aminothiocarbonyl, where the alkyl or alkoxy radicals mentioned may be partially or fully halogenated and/or may carry one to three of the following groups: cyano, $C_1$-$C_4$-alkoxy, $C_1$-$C_4$-alkoxycarbonyl, $C_1$-$C_4$-alkylaminocarbonyl, di-($C_1$-$C_4$-alkyl)aminocarbonyl or $C_1$-$C_4$-alkylcarbonyloxy;

phenyl-$C_1$-$C_6$-alkyl, phenylcarbonyl, phenylcarbonyl-$C_1$-$C_6$-alkyl, phenylsulfonylaminocarbonyl or phenyl-$C_1$-$C_6$-alkylcarbonyl, where the phenyl ring may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or

SO$_2$R$^7$;

especially preferably hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_1$-$C_6$-alkoxycarbonyl, ($C_1$-$C_6$-alkyl)aminocarbonyl, di-($C_1$-$C_6$-alkyl)aminocarbonyl, N—($C_1$-$C_6$-alkoxy)-N—($C_1$-$C_6$-alkyl)aminocarbonyl, ($C_1$-$C_6$)alkylaminothiocarbonyl, di-($C_1$-$C_6$-alkyl)-aminothiocarbonyl, phenyl-$C_1$-$C_6$-alkyl, phenylcarbonyl, phenylcarbonyl-$C_1$-$C_6$-alkyl or phenyl-$C_1$-$C_6$-alkylcarbonyl, where the phenyl ring may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or

SO$_2$R$^7$.

Preference is likewise given to the heteroaroyl-substituted serineamides of the formula (I), in which R$^4$ is hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_3$-$C_6$-cycloalkylcarbonyl, $C_1$-$C_6$-alkmcarbonyl, $C_1$-$C_6$-alkylaminocarbonyl, di-($C_1$-$C_6$-alkyl)aminocarbonyl, N—($C_1$-$C_6$-alkoxy)-N—($C_1$-$C_6$-alkyl)aminocarbonyl, ($C_1$-$C_6$)-alkylaminothiocarbonyl, di-($C_1$-$C_6$-alkyl)aminothiocarbonyl, $C_1$-$C_6$-alkoxyimino-$C_1$-$C_6$-alkyl, where the alkyl, cycloalkyl or alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di-($C_1$-$C_4$-alkyl)amino, $C_1$-$C_4$alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl or $C_1$-$C_4$-alkylcarbonyloxy; or

SO$_2$R$^7$.

Preference is likewise given to the heteroaroyl-substituted serineamides of the formula (I), in which R$^4$ is hydrogen, $C_1$-$C_6$-alkyl, $C_3$-$C_6$-alkenyl, $C_3$-$C_6$-alkynyl, formyl, $C_1$-$C_6$-alkylcarbonyl, $C_1$-$C_6$-alkoxycarbonyl, $C_1$-$C_6$-alkylaminocarbonyl, di-($C_1$-$C_6$-alkyl)aminocarbonyl, N—($C_1$-$C_6$-alkoxy)-N—($C_1$-$C_6$-alkyl) aminocarbonyl, where the alkyl and alkoxy radicals mentioned may be partially or fully halogenated and/or may carry one to three of the following groups: cyano, $C_1$-$C_4$-alkoxy, $C_1$-$C_4$-alkylaminocarbonyl or di-($C_1$-$C_4$-alkyl)aminocarbonyl;

phenyl-$C_1$-$C_6$-alkyl, phenylcarbonyl, phenylcarbonyl-$C_1$-$C_6$-alkyl, phenyl-aminocarbonyl or N—($C_1$-$C_6$-alkyl)-N-(phenyl)aminocarbonyl, where the phenyl may be partially or fully halogenated and/or may carry one to three of the following groups: cyano, $C_1$-$C_4$-alkyl or $C_1$-$C_4$-haloalkyl; or

SO$_2$R$^7$;

particularly preferably hydrogen, formyl, $C_1$-$C_4$-alkylcarbonyl, $C_1$-$C_4$-alkylaminocarbonyl, di-($C_1$-$C_4$-alkyl) aminocarbonyl, phenylaminocarbonyl, N—($C_1$-$C_4$alkyl)-N-(phenyl)aminocarbonyl, SO$_2$CH$_3$, SO$_2$CF$_3$ or SO$_2$(C$_6$H$_5$).

Preference is likewise given to the heteroaroyl-substituted serineamides of the formula (I), in which R$^5$ and R$^6$ together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom or 2 oxygen or sulfur atoms, where the ring is unsubstituted or substituted as indicated in formula (I), and where the ring is monocyclic or fused to a further 3- to 6-membered saturated or partially unsaturated ring which is carbocyclic or contains 1 or 2 nitrogen atoms, 0 to 1 nitrogen atom or 1 oxygen atom or sulfur atom, 2 oxygen atoms or sulfur atoms, 0 to 1 nitrogen atom and 1 oxygen atom and 1 sulfur atom, where the fused ring is unsubstituted or substituted by 1 to 3, in the case of halogen also up to the maximum possible number, substituents from the group consisting of halogen, $C_1$-$C_6$-alkyl, $C_1$-$C_6$-haloalkyl and $C_1$-$C_6$-alkoxy, and where the ring is not bridged or bridged by a 1- to 3-membered saturated or unsaturated chain which contains no heteroatoms or contains 1 nitrogen atom, 0 or 1 nitrogen atom and 1 oxygen atom or 1 sulfur atom, where the bridge is unsubstituted or substituted by 1 to 3, in the case of halogen also up to the maximum possible number, substituents from the group consisting of halogen, $C_1$-$C_6$-alkyl, hydroxyl and $C_1$-$C_6$-alkoxy; particularly preferably together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 to 1 nitrogen atom and 1 oxygen and 1 sulfur atom, 2 oxygen or sulfur atoms, where the ring is unsubstituted or substituted by 1 to 3, in the case of halogen also up to the maximum possible number, substituents from the group consisting of halogen, $C_1$-$C_6$-alkyl, hydroxyl, $C_1$-$C_6$-alkoxy, formyl, $C_1$-$C_6$-alkyl-carbonyl, $C_1$-$C_6$-alkoxycarbonyl, $C_1$-$C_6$-alkylaminocarbonyl, di-($C_1$-$C_6$-alkyl)-aminocarbonyl, alkylsulfonylamino, carbonyl, alkoxyimino, where the alkyl and alkoxy radicals mentioned may be partially or fully halogenated and/or may carry one to three of the following groups: cyano, hydroxyl and $C_1$-$C_4$-alkoxy, phenyl, partially or fully halogenated, and where the ring is monocyclic or fused to a further 3- to 6-membered saturated or partially unsaturated ring which is carbocyclic or contains 1 or 2 nitrogen atoms, 0 to 1 nitrogen atom and 1 oxygen atom or sulfur atom, 2 oxygen atoms or sulfur atoms, 0 to 1 nitrogen atom and 1 oxygen atom and 1 sulfur atom, where the fused ring is unsubstituted or substituted by 1 to 3, in the case of halogen also up to the maximum possible number, substituents from the group consisting of halogen, $C_1$-$C_6$-alkyl, $C_1$-$C_6$-haloalkyl and $C_1$-$C_6$-alkoxy, and where the ring is not bridged or bridged by a 1- to 3-membered saturated or unsaturated chain which contains no heteroatoms or contains one nitrogen atom or 0 or 1 nitrogen atom and 1 oxygen atom or 1 sulfur atom, where the bridge is unsubstituted or substituted by 1 to 3, in the case of halogen also up to the maximum possible number, substituents from the group consisting of halogen, $C_1$-$C_6$-alkyl, hydroxyl and $C_1$-$C_6$-alkoxy.

Preference is likewise given to the heteroaroyl-substituted serineamides of the formula (I), in which $R^5$ and $R^6$ together with the carbon atom to which they are attached are a 3- to 12-membered monocyclic saturated or partially unsaturated ring which is carbocyclic or contains 1 to 3 nitrogen atoms, 0 to 3 nitrogen atoms and 1 oxygen atom or sulfur atom, 0 to 2 nitrogen atoms and 2 oxygen or sulfur atoms, 0 or 1 nitrogen atom and 1 oxygen and 1 sulfur atom, 3 oxygen or sulfur atoms, 2 oxygen atoms and 1 sulfur atom, or 1 oxygen and 2 sulfur atoms, where the ring is unsubstituted or substituted as indicated in formula (I);

particularly preferably together with the carbon atom to which they are attached are a 3- to 7-membered monocyclic saturated or partially unsaturated ring which is carbocyclic or contains 1 or 2 nitrogen atoms, 0 or 1 nitrogen atom and 1 oxygen atom or sulfur atom, 0 to 1 nitrogen atom and 1 oxygen and 1 sulfur atom, 3 oxygen or sulfur atoms, where the ring is unsubstituted or substituted as indicated in formula (I);

very particularly preferably together with the carbon atom to which they are attached are a 3- to 7-membered monocyclic saturated or partially unsaturated ring which is carbocyclic or contains 1 to 3 nitrogen atoms, 0 to 3 nitrogen atoms and 1 oxygen atom or sulfur atom, 0 to 2 nitrogen atoms and 2 oxygen or sulfur atoms, 0 or 1 nitrogen atom and 1 oxygen and 1 sulfur atom, 3 oxygen or sulfur atoms, 2 oxygen atoms and 1 sulfur atom, or 1 oxygen and 2 sulfur atoms, where the ring is unsubstituted or substituted by 1 to 3, in the case of halogen also up to the maximum possible number, substituents from the group consisting of halogen, $C_1$-$C_6$-alkyl, hydroxyl, $C_1$-$C_6$-alkoxy, formyl, $C_1$-$C_6$-alkyl-carbonyl, $C_1$-$C_6$-alkoxycarbonyl, $C_1$-$C_6$-alkylaminocarbonyl, di-($C_1$-$C_6$-alkyl)aminocarbonyl, alkylsulfonylamino, carbonyl, alkoxyimino, where the alkyl and alkoxy radicals mentioned may be partially or fully halogenated and/or may carry one to three of the following groups: cyano, hydroxyl, $C_1$-$C_4$-alkoxy, phenyl, partially or fully halogenated.

Preference is likewise given to the heteroaroyl-substituted serineamides of the formula (I), in which $R^5$ and $R^6$ together with the carbon atom to which they are attached are a 3- to 12-membered saturated or partially unsaturated ring which is carbocyclic or contains 1 to 3 nitrogen atoms, 0 to 3 nitrogen atoms and 1 oxygen or sulfur atom, 0 to 2 nitrogen atoms and 2 oxygen or sulfur atoms, 0 or 1 nitrogen atom and 1 oxygen and 1 sulfur atom, 3 oxygen or sulfur atoms, 2 oxygen atoms and 1 sulfur atom, or 1 oxygen and 2 sulfur atoms, where the ring is unsubstituted or substituted as indicated in formula (I); and where the ring is fused to a further 3- to 7-membered saturated, partially unsaturated or fully unsaturated ring which is carbocyclic or contains 1 to 3 nitrogen atoms, 0 to 2 nitrogen atoms and 1 oxygen atom or sulfur atom, 0 or 1 nitrogen atom and 2 oxygen atoms or sulfur atoms, 0 to 1 nitrogen atom and 1 oxygen atom and 1 sulfur atom, 2 oxygen atoms and 1 sulfur atom or 1 oxygen atom and 2 sulfur atoms, where the fused ring is unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl;

particularly preferably together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom, 2 oxygen or sulfur atoms, where the ring is unsubstituted or substituted as indicated in formula (I);

and where the ring is fused to a further 3- to 7-membered saturated, partially unsaturated or fully unsaturated ring which is carbocyclic or contains 1 to 3 nitrogen atoms, 0 to 2 nitrogen atoms and 1 oxygen atom or sulfur atom, 0 or 1 nitrogen atom and 2 oxygen atoms or sulfur atoms, 0 or 1 nitrogen atom and 1 oxygen atom and 1 sulfur atom, 2 oxygen atoms and 1 sulfur atom or 1 oxygen atom and 2 sulfur atoms, where the fused ring is unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl;

very particularly preferably together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom, 2 oxygen or sulfur atoms, where the ring is unsubstituted or substituted by 1 to 3, in the case of halogen also up to the maximum possible number, substituents from the group consisting of halogen, $C_1$-$C_6$-alkyl, hydroxyl, $C_1$-$C_6$-alkoxy, formyl, $C_1$-$C_6$-alkyl-carbonyl, $C_1$-$C_6$-alkoxycarbonyl, $C_1$-$C_6$-alkylaminocarbonyl, di-($C_1$-$C_6$-alkyl)aminocarbonyl, alkylsulfonylamino, carbonyl, alkoxyimino, where the alkyl and alkoxy radicals mentioned may be partially or fully halogenated and/or may carry one to three of the following groups: cyano, hydroxyl, $C_1$-$C_4$-alkoxy, phenyl, partially or fully halogenated, and where the ring may be fused to a further 3- to 6-membered saturated or partially unsaturated ring which is carbocyclic or contains 1 or 2 nitrogen atoms, 0 or 1 nitrogen atom and 1 oxygen atom or sulfur atom, 2 oxygen atoms or sulfur atoms, 0 or 1 nitrogen atom and 1 oxygen atom and 1 sulfur atom, where the fused ring is unsubstituted or substituted by 1 to 3, in the case of halogen also up to the maximum possible number, substituents from the group consisting of halogen, $C_1$-$C_6$-alkyl, $C_1$-$C_6$-haloalkyl and $C_1$-$C_6$-alkoxy.

Preference is likewise given to the heteroaroyl-substituted serineamides of the formula (I), in which $R^5$ and $R^6$ together with the carbon atom to which they are attached are a 3- to 12-membered saturated or partially unsaturated ring which is carbocyclic or contains 1 to 3 nitrogen atoms, 0 to 3 nitrogen atoms and 1 oxygen or sulfur atom, 0 to 2 nitrogen atoms and 2 oxygen or sulfur atoms, 0 or 1 nitrogen atom and 1 oxygen and 1 sulfur atom, 3 oxygen or sulfur atoms, 2 oxygen atoms and 1 sulfur atom, or 1 oxygen and 2 sulfur atoms, where the ring is unsubstituted or substituted as indicated in formula (I), and where the ring is bridged by a 1- to 4-membered saturated or unsaturated chain which contains no heteroatoms or contains 1 or 2 nitrogen atoms, 0 or 1 nitrogen atom and 1 oxygen atom or 1 sulfur atom, 0 or 1 nitrogen atom and 2 oxygen atoms or 2 sulfur atoms, or 0 or 1 nitrogen atom and 1 oxygen atom and 1 sulfur atom, where the bridges are unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl;

particularly preferably together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom, 2 oxygen or sulfur atoms, where the ring is unsubstituted or substituted as indicated in formula (I), and where the ring is bridged by a 1- to 4-membered saturated or unsaturated chain which contains no heteroatoms or contains 1 to 2 nitrogen atoms, 0 or 1 nitrogen atom and 1 oxygen atom or 1 sulfur atom, 0 or 1 nitrogen atom and 2 oxygen atoms or 2 sulfur atoms or 0 or 1 nitrogen atom and 1 oxygen atom and 1 sulfur atom, where the bridge is unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl;

very particularly preferably together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom, 2 oxygen or sulfur atoms, where the ring is unsubstituted or substituted by 1 to 3, in the case of halogen also up to the maximum possible number, substituents from the group consisting of halogen, $C_1$-$C_6$-alkyl, hydroxyl, $C_1$-$C_6$-alkoxy, formyl, $C_1$-$C_6$-alkyl-carbonyl, $C_1$-$C_6$-alkoxycarbonyl, $C_1$-$C_6$-alkylaminocarbonyl, di-($C_1$-$C_6$-alkyl)aminocarbonyl, alkylsulfonylamino, carbonyl, alkoxyimino, where the alkyl and alkoxy radicals mentioned may be partially or fully halogenated and/or may carry one to three of the following groups: cyano, hydroxyl, $C_1$-$C_4$-alkoxy, phenyl, partially or fully halogenated, and where the ring is bridged by a 1- to 4-membered saturated or unsaturated chain which contains no heteroatoms or contains 1 to 2 nitrogen atoms, 0 or 1 nitrogen atom and 1 oxygen or 1 sulfur atom, 0 or 1 nitrogen atom and 2 oxygen atoms or 2 sulfur atoms or 0 or 1 nitrogen atom and 1 oxygen atom and 1 sulfur atom, where the bridge is unsubstituted or substituted by 1 to 3, in the case of halogen also up to the maximum possible number, substituents from the group consisting of halogen, cyano, nitro, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl.

Preference is likewise given to the heteroaroyl-substituted serineamides of the formula (I), in which $R^7$ is $C_1$-$C_6$-alkyl, $C_1$-$C_6$-haloalkyl or phenyl, where the phenyl radical may be partially or fully halogenated and/or may be substituted by $C_1$-$C_4$-alkyl;

particularly preferably $C_1$-$C_4$-alkyl, $C_1$-$C_4$-haloalkyl or phenyl;

especially preferably methyl, trifluoromethyl or phenyl.

Particular preference is given to the heteroaroyl-substituted serineamides of the formula (I) in which A is 5- or 6-membered heteroaryl selected from the group consisting of thienyl, furyl, pyrazolyl, imidazolyl, thiazolyl, oxazolyl and pyridyl;

where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;

$R^1$ and $R^2$ are hydrogen;

$R^3$ is $C_1$-$C_4$-alkyl,
particularly preferably $CH_3$;

$R^4$ is hydrogen, formyl, $C_1$-$C_4$-alkylcarbonyl, $C_1$-$C_4$-alkylaminocarbonyl, di-($C_1$-$C_4$-alkyl)aminocarbonyl, phenylaminocarbonyl, N—($C_1$-$C_4$-alkyl)-N-(phenyl)aminocarbonyl, $SO_2CH_3$, $SO_2CF_3$ or $SO_2(C_6H_5)$;

$R^5$ and $R^6$ together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom, 2 oxygen or sulfur atoms, where the ring is unsubstituted or substituted by 1 to 3, in the case of halogen also up to the maximum possible number, substituents from the group consisting of halogen, $C_1$-$C_6$-alkyl, hydroxyl, $C_1$-$C_6$-alkoxy, formyl, $C_1$-$C_6$-alkyl-carbonyl, $C_1$-$C_6$-alkoxycarbony, $C_1$-$C_6$-alkylaminocarbonyl, di-($C_3$_$C_6$-alkyl)aminocarbonyl, alkylsulfonylamino, carbonyl, alkoxyimino, where the alkyl and alkoxy radicals mentioned may be partially or fully halogenated and/or may carry one to three of the following groups: cyano, hydroxyl, $C_1$-$C_4$-alkoxy, phenyl, partially or fully halogenated, and the ring is monocyclic or fused to a further 3- to 6-membered saturated or partially unsaturated ring which is carbocyclic or contains 1 to 2 nitrogen atoms, 0 or 1 nitrogen atom and 1 oxygen atom or sulfur atom, 2 oxygen atoms or sulfur atoms, 0 or 1 nitrogen atom and 1 oxygen atom and 1 sulfur atom, where the fused ring is unsubstituted or substituted by 1 to 3, in the case of halogen also up to the maximum possible number, substituents from the group consisting of halogen, $C_1$-$C_6$-alkyl, $C_1$-$C_6$-haloalkyl and $C_1$-$C_6$-alkoxy, or the ring is bridged by a 1- to 3-membered saturated or unsaturated chain which contains no heteroatoms or contains 1 nitrogen atom, 0 or 1 nitrogen atom and 1 oxygen atom or 1 sulfur atom, where the bridge is unsubstituted or substituted by 1 to 3, in the case of halogen also up to the maximum possible number, substituents from the group consisting of halogen, $C_1$-$C_6$-alkyl, hydroxyl and $C_1$-$C_6$-alkoxy.

Most preference is given to the compounds of the formula (I.a) (corresponds to formula (I) where A=A-1 where $R^8$=H; $R^9$=$CF_3$, $R^1$, $R^2$ and $R^5$=H; $R^3$=$CH_3$), in particular to the compounds of the formula I.a.1 to I.a.138 of Table 1, where the definitions of the variables A and $R^1$ to $R^6$ are of particular importance for the compounds according to the invention not only in combination with one another, but in each case also on their own.

TABLE 1

I.a

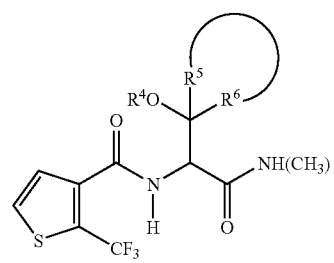

| No. | $R^4$ | $R^5 + R^6$ |
|---|---|---|
| I.a.1.1 | H | —$CH_2$—$CH_2$— |
| I.a.1.2 | H | —$CH_2$—$CH_2$—$CH_2$— |
| I.a.1.3 | H | —$CH_2$—O—$CH_2$— |
| I.a.1.4 | H | —$CH_2$—$CH_2$—$CH_2$—$CH_2$— |
| I.a.1.5 | H | —$CHCH_3$—$CH_2$—$CH_2$—$CHCH_3$— |
| I.a.1.6 | H | —$CH_2$—$CH_2$—$CH_2$—$CHCH_3$— |
| I.a.1.7 | H | —$CH_2$—$CH_2$—$CH_2$—$CH(OCH_3)$— |
| I.a.1.8 | H | —$CH_2$—$CH_2$—O—$CH_2$— |
| I.a.1.9 | H | —$CH_2$—$CH_2$—O—$CHCH_3$— |
| I.a.1.10 | H | —$CH_2$—$CH_2$—O—$CH(OCH_3)$— |
| I.a.1.11 | H | —$CH_2$—O—$CH_2$—$CHCH_3$— |
| I.a.1.12 | H | —$CH_2$—O—$CH_2$—$CH(OCH_3)$— |
| I.a.1.13 | H | —$CH_2$—$CH_2$—N(COH)—$CH_2$— |
| I.a.1.14 | H | —$CH_2$—$CH_2$—N($COCH_3$)—$CH_2$— |
| I.a.1.15 | H | —$CH_2$—$CH_2$—N($COOCH_3$)—$CH_2$— |
| I.a.1.16 | H | —$CH_2$—$CH_2$—N($CONHCH_3$)—$CH_2$— |
| I.a.1.17 | H | —$CH_2$—$CH_2$—N($CON(CH_3)_2$)—$CH_2$— |
| I.a.1.18 | H | —$CH_2$—$CH_2$—$CH_2$—$CH_2$—$CH_2$— |
| I.a.1.19 | H | —$CH_2$—$CH_2$—$CH_2$—$CH_2$—$CHCH_3$— |
| I.a.1.20 | H | —$CH_2$—$CH_2$—$CH_2$—$CH_2$—$CH(OCH_3)$— |
| I.a.1.21 | H | —$CH_2$—$CH_2$—$CH_2$—O—$CH_2$— |
| I.a.1.22 | H | —$CH_2$—$CH_2$—$CH_2$—O—$CHCH_3$— |
| I.a.1.23 | H | —$CH_2$—$CH_2$—$CH_2$—O—$CH(OCH_3)$— |
| I.a.1.24 | H | —$CH_2$—$CH_2$—O—$CH_2$—$CH_2$— |
| I.a.1.25 | H | —$CH_2$—$CH_2$—O—$CH_2$—$CHCH_3$— |
| I.a.1.26 | H | —$CH_2$—$CH_2$—$CH_2$—O—$CH(OCH_3)$— |
| I.a.1.27 | H | —$CH_2$—O—$CH_2$—$CH_2$—$CH_2$— |
| I.a.1.28 | H | —$CH_2$—O—$CH_2$—$CH_2$—$CHCH_3$— |

TABLE 1-continued

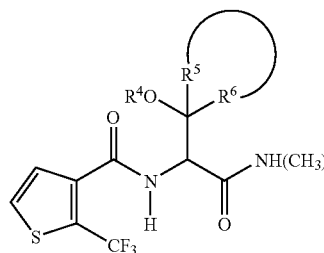

I.a

| No. | R⁴ | R⁵ + R⁶ |
|---|---|---|
| I.a.1.29 | H | —CH₂—O—CH₂—CH₂—CH(OCH₃)— |
| I.a.1.30 | H | —CH₂—O—CH₂—O—CH₂— |
| I.a.1.31 | H | —CH₂—CH₂—CH₂—N(COH)—CH₂— |
| I.a.1.32 | H | —CH₂—CH₂—CH₂—N(COCH₃)—CH₂— |
| I.a.1.33 | H | —CH₂—CH2—CH₂—N(COOCH₃)—CH₂— |
| I.a.1.34 | H | —CH₂—CH₂—CH₂—N(CONHCH₃)—CH₂— |
| I.a.1.35 | H | —CH₂—CH₂—CH₂—N(CON(CH₃)₂)—CH₂— |
| I.a.1.36 | H | —CH₂—CH₂—N(COH)—CH₂—CH₂— |
| I.a.1.37 | H | —CH₂—CH₂—N(COCH₃)—CH₂—CH₂— |
| I.a.1.38 | H | —CH₂—CH₂—N(COOCH₃)—CH₂—CH₂— |
| I.a.1.39 | H | —CH₂—CH₂—N(CONHCH₃)—CH₂—CH₂— |
| I.a.1.40 | H | —CH₂—CH₂—N(CON(CH₃)₂)—CH₂—CH₂— |
| I.a.1.41 | H | —CH₂—CH₂—CH₂—CH₂—CH₂—CH₂— |
| I.a.1.42 | H | —CH₂—O—CH₂—CH₂—O—CH₂— |
| I.a.1.43 | C(O)CH₃ | —CH₂—CH₂— |
| I.a.1.44 | C(O)CH₃ | —CH₂—CH₂—CH₂— |
| I.a.1.45 | C(O)CH₃ | —CH₂—O—CH₂— |
| I.a.1.46 | C(O)CH₃ | —CH₂—CH₂—CH₂—CH₂— |
| I.a.1.47 | C(O)CH₃ | —CHCH₃—CH₂—CH₂—CHCH₃— |
| I.a.1.48 | C(O)CH₃ | —CH₂—CH₂—CH₂—CHCH₃— |
| I.a.1.49 | C(O)CH₃ | —CH₂—CH₂—CH₂—CH(OCH₃)— |
| I.a.1.50 | C(O)CH₃ | —CH₂—CH₂—O—CH₂— |
| I.a.1.51 | C(O)CH₃ | —CH₂—CH₂—O—CHCH₃— |
| I.a.1.52 | C(O)CH₃ | —CH₂—CH₂—O—CH(OCH₃)— |
| I.a.1.53 | C(O)CH₃ | —CH₂—O—CH₂—CHCH₃— |
| I.a.1.54 | C(O)CH₃ | —CH₂—O—CH₂—CH(COH₃)— |
| I.a.1.55 | C(O)CH₃ | —CH₂—CH₂—N(COH)—CH₂— |
| I.a.1.56 | C(O)CH₃ | —CH₂—CH₂—N(COCH₃)—CH₂— |
| I.a.1.57 | C(O)CH₃ | —CH₂—CH₂—N(COOCH₃)—CH₂— |
| I.a.1.58 | C(O)CH₃ | —CH₂—CH₂—N(CONHCH₃)—CH₂— |
| I.a.1.59 | C(O)CH₃ | —CH₂—CH₂—N(CON(CH₃)₂)—CH₂— |
| I.a.1.60 | C(O)CH₃ | —CH₂—CH₂—CH₂—CH₂—CH₂— |
| I.a.1.61 | C(O)CH₃ | —CH₂—CH₂—CH₂—CH₂—CHCH₃— |
| I.a.1.62 | C(O)CH₃ | —CH₂—CH₂—CH₂—CH₂—CH(OCH₃)— |
| I.a.1.63 | C(O)CH₃ | —CH₂—CH₂—CH₂—O—CH₂— |
| I.a.1.64 | C(O)CH₃ | —CH₂—CH₂—CH₂—O—CHCH₃— |
| I.a.1.65 | C(O)CH₃ | —CH₂—CH₂—CH₂—O—CH(OCH₃)— |
| I.a.1.66 | C(O)CH₃ | —CH₂—CH₂—O—CH₂—CH₂— |
| I.a.1.67 | C(O)CH₃ | —CH₂—CH₂—O—CH₂—CHCH₃— |
| I.a.1.68 | C(O)CH₃ | —CH₂—CH₂—CH₂—O—CH(OCH₃)— |
| I.a.1.69 | C(O)CH₃ | —CH₂—O—CH₂—CH₂—CH₂— |
| I.a.1.70 | C(O)CH₃ | —CH₂—O—CH₂—CH₂—CHCH₃— |
| I.a.1.71 | C(O)CH₃ | —CH₂—O—CH₂—CH₂—CH(OCH₃)— |
| I.a.1.72 | C(O)CH₃ | —CH₂—O—CH₂—O—CH₂— |
| I.a.1.73 | C(O)CH₃ | —CH₂—CH₂—CH₂—N(COH)—CH₂— |
| I.a.1.74 | C(O)CH₃ | —CH₂—CH₂—CH₂—N(COCH₃)—CH₂— |
| I.a.1.75 | C(O)CH₃ | —CH₂—CH2—CH₂—N(COOCH₃)—CH₂— |
| I.a.1.76 | C(O)CH₃ | —CH₂—CH₂—CH₂—N(CONHCH₃)—CH₂— |
| I.a.1.77 | C(O)CH₃ | —CH₂—CH₂—CH₂—N(CON(CH₃)₂)—CH₂— |
| I.a.1.78 | C(O)CH₃ | —CH₂—CH₂—N(COH)—CH₂—CH₂— |
| I.a.1.79 | C(O)CH₃ | —CH₂—CH₂—N(COCH₃)—CH₂—CH₂— |
| I.a.1.80 | C(O)CH₃ | —CH₂—CH₂—N(COOCH₃)—CH₂—CH₂— |
| I.a.1.81 | C(O)CH₃ | —CH₂—CH₂—N(CONHCH₃)—CH₂—CH₂— |
| I.a.1.82 | C(O)CH₃ | —CH₂—CH₂—N(CON(CH₃)₂)—CH₂—CH₂— |
| I.a.1.83 | C(O)CH₃ | —CH₂—CH₂—CH₂—CH₂—CH₂—CH₂— |
| I.a.1.84 | C(O)CH₃ | —CH₂—O—CH₂—CH₂—O—CH₂— |
| I.a.1.85 | C(O)NHCH₃ | —CH₂—CH₂— |
| I.a.1.86 | C(O)NHCH₃ | —CH₂—CH₂—CH₂— |
| I.a.1.87 | C(O)NHCH₃ | —CH₂—O—CH₂— |
| I.a.1.88 | C(O)NHCH₃ | —CH₂—CH₂—CH₂—CH₂— |
| I.a.1.89 | C(O)NHCH₃ | —CHCH₃—CH₂—CH₂—CHCH₃— |
| I.a.1.90 | C(O)NHCH₃ | —CH₂—CH₂—CH₂—CHCH₃— |
| I.a.1.91 | C(O)NHCH₃ | —CH₂—CH₂—CH₂—CH(OCH₃)— |
| I.a.1.92 | C(O)NHCH₃ | —CH₂—CH₂—O—CH₂— |

TABLE 1-continued

I.a

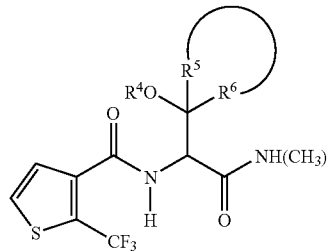

| No. | R⁴ | R⁵ + R⁶ |
| --- | --- | --- |
| I.a.1.93 | C(O)NHCH₃ | —CH₂—CH₂—O—CHCH₃— |
| I.a.1.94 | C(O)NHCH₃ | —CH₂—CH₂—O—CH(OCH₃)— |
| I.a.1.95 | C(O)NHCH₃ | —CH₂—O—CH₂—CHCH₃— |
| I.a.1.96 | C(O)NHCH₃ | —CH₂—O—CH₂—CH(OCH₃)— |
| I.a.1.97 | C(O)NHCH₃ | —CH₂—CH₂—N(COH)—CH₂— |
| I.a.1.98 | C(O)NHCH₃ | —CH₂—CH₂—N(COCH₃)—CH₂— |
| I.a.1.99 | C(O)NHCH₃ | —CH₂—CH₂—N(COOCH₃)—CH₂— |
| I.a.1.100 | C(O)NHCH₃ | —CH₂—CH₂—N(CONHCH₃)—CH₂— |
| I.a.1.101 | C(O)NHCH₃ | —CH₂—CH₂—N(CON(CH₃)₂)—CH₂— |
| I.a.1.102 | C(O)NHCH₃ | —CH₂—CH₂—CH₂—CH₂—CH₂— |
| I.a.1.103 | C(O)NHCH₃ | —CH₂—CH₂—CH₂—CH₂—CHCH₃— |
| I.a.1.104 | C(O)NHCH₃ | —CH₂—CH₂—CH₂—CH₂—CH(OCH₃)— |
| I.a.1.105 | C(O)NHCH₃ | —CH₂—CH₂—CH₂—O—CH₂— |
| I.a.1.106 | C(O)NHCH₃ | —CH₂—CH₂—CH₂—O—CHCH₃— |
| I.a.1.107 | C(O)NHCH₃ | —CH₂—CH₂—CH₂—O—CH(OCH₃)— |
| I.a.1.108 | C(O)NHCH₃ | —CH₂—CH₂—O—CH₂—CH₂— |
| I.a.1.109 | C(O)NHCH₃ | —CH₂—CH₂—O—CH₂—CHCH₃— |
| I.a.1.110 | C(O)NHCH₃ | —CH₂—CH₂—O—CH₂—CH(OCH₃)— |
| I.a.1.111 | C(O)NHCH₃ | —CH₂—O—CH₂—CH₂—CH₂— |
| I.a.1.112 | C(O)NHCH₃ | —CH₂—O—CH₂—CH₂—CHCH₃— |
| I.a.1.113 | C(O)NHCH₃ | —CH₂—O—CH₂—CH₂—CH(OCH₃)— |
| I.a.1.114 | C(O)NHCH₃ | —CH₂—O—CH₂—O—CH₂— |
| I.a.1.115 | C(O)NHCH₃ | —CH₂—CH₂—CH₂—N(COH)—CH₂— |
| I.a.1.116 | C(O)NHCH₃ | —CH₂—CH₂—CH₂—N(COCH₃)—CH₂— |
| I.a.1.117 | C(O)NHCH₃ | —CH₂—CH2—CH₂—N(COOCH₃)—CH₂— |
| I.a.1.118 | C(O)NHCH₃ | —CH₂—CH₂—CH₂—N(CONHCH₃)—CH₂— |
| I.a.1.119 | C(O)NHCH₃ | —CH₂—CH₂—CH₂—N(CON(CH₃)₂)—CH₂— |
| I.a.1.120 | C(O)NHCH₃ | —CH₂—CH₂—N(COH)—CH₂—CH₂— |
| I.a.1.121 | C(O)NHCH₃ | —CH₂—CH₂—N(COCH₃)—CH₂—CH₂— |
| I.a.1.122 | C(O)NHCH₃ | —CH₂—CH₂—N(COOCH₃)—CH₂—CH₂— |
| I.a.1.123 | C(O)NHCH₃ | —CH₂—CH₂—N(CONHCH₃)—CH₂—CH₂— |
| I.a.1.124 | C(O)NHCH₃ | —CH₂—CH₂—N(CON(CH₃)₂)—CH₂—CH₂— |
| I.a.1.125 | C(O)NHCH₃ | —CH₂—CH₂—CH₂—CH₂—CH₂—CH₂— |
| I.a.1.126 | C(O)NHCH₃ | —CH₂—O—CH₂—CH₂—O—CH₂— |
| I.a.1.127 | CON(CH₃)₂ | —CH₂—CH₂— |
| I.a.1.128 | CON(CH₃)₂ | —CH₂—CH₂—CH₂— |
| I.a.1.129 | CON(CH₃)₂ | —CH₂—O—CH₂— |
| I.a.1.130 | CON(CH₃)₂ | —CH₂—CH₂—CH₂—CH₂— |
| I.a.1.131 | CON(CH₃)₂ | —CHCH₃—CH₂—CH₂—CHCH₃— |
| I.a.1.132 | CON(CH₃)₂ | —CH₂—CH₂—CH₂—CHCH₃— |
| I.a.1.133 | CON(CH₃)₂ | —CH₂—CH₂—CH₂—CH(OCH₃)— |
| I.a.1.134 | CON(CH₃)₂ | —CH₂—CH₂—O—CH₂— |
| I.a.1.135 | CON(CH₃)₂ | —CH₂—CH₂—O—CHCH₃— |
| I.a.1.136 | CON(CH₃)₂ | —CH₂—CH₂—O—CH(OCH₃)— |
| I.a.1.137 | CON(CH₃)₂ | —CH₂—O—CH₂—CHCH₃— |
| I.a.1.138 | CON(CH₃)₂ | —CH₂—O—CH₂—CH(OCH₃)— |
| I.a.1.139 | CON(CH₃)₂ | —CH₂—CH₂—N(COH)—CH₂— |
| I.a.1.140 | CON(CH₃)₂ | —CH₂—CH₂—N(COCH₃)—CH₂— |
| I.a.1.141 | CON(CH₃)₂ | —CH₂—CH₂—N(COOCH₃)—CH₂— |
| I.a.1.142 | CON(CH₃)₂ | —CH₂—CH₂—N(CONHCH₃)—CH₂— |
| I.a.1.143 | CON(CH₃)₂ | —CH₂—CH₂—N(CON(CH₃)₂)—CH₂— |
| I.a.1.144 | CON(CH₃)₂ | —CH₂—CH₂—CH₂—CH₂—CH₂— |
| I.a.1.145 | CON(CH₃)₂ | —CH₂—CH₂—CH₂—CH₂—CHCH₃— |
| I.a.1.146 | CON(CH₃)₂ | —CH₂—CH₂—CH₂—CH₂—CH(OCH₃)— |
| I.a.1.147 | CON(CH₃)₂ | —CH₂—CH₂—CH₂—O—CH₂— |
| I.a.1.148 | CON(CH₃)₂ | —CH₂—CH₂—CH₂—O—CHCH₃— |
| I.a.1.149 | CON(CH₃)₂ | —CH₂—CH₂—CH₂—O—CH(OCH₃)— |
| I.a.1.150 | CON(CH₃)₂ | —CH₂—CH₂—O—CH₂—CH₂— |
| I.a.1.151 | CON(CH₃)₂ | —CH₂—CH₂—O—CH₂—CHCH₃— |
| I.a.1.152 | CON(CH₃)₂ | —CH₂—CH₂—O—CH₂—CH(OCH₃)— |
| I.a.1.153 | CON(CH₃)₂ | —CH₂—O—CH₂—CH₂—CH₂— |
| I.a.1.154 | CON(CH₃)₂ | —CH₂—O—CH₂—CH₂—CHCH₃— |
| I.a.1.155 | CON(CH₃)₂ | —CH₂—O—CH₂—CH₂—CH(OCH₃)— |
| I.a.1.156 | CON(CH₃)₂ | —CH₂—O—CH₂—O—CH₂— |

TABLE 1-continued

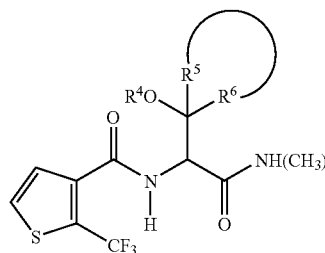

I.a

| No. | $R^4$ | $R^5 + R^6$ |
|---|---|---|
| I.a.1.157 | $CON(CH_3)_2$ | $-CH_2-CH_2-CH_2-N(COH)-CH_2-$ |
| I.a.1.158 | $CON(CH_3)_2$ | $-CH_2-CH_2-CH_2-N(COCH_3)-CH_2-$ |
| I.a.1.159 | $CON(CH_3)_2$ | $-CH_2-CH_2-CH_2-N(COOCH_3)-CH_2-$ |
| I.a.1.160 | $CON(CH_3)_2$ | $-CH_2-CH_2-CH_2-N(CONHCH_3)-CH_2-$ |
| I.a.1.161 | $CON(CH_3)_2$ | $-CH_2-CH_2-CH_2-N(CON(CH_3)_2)-CH_2-$ |
| I.a.1.162 | $CON(CH_3)_2$ | $-CH_2-CH_2-N(COH)-CH_2-CH_2-$ |
| I.a.1.163 | $CON(CH_3)_2$ | $-CH_2-CH_2-N(COCH_3)-CH_2-CH_2-$ |
| I.a.1.164 | $CON(CH_3)_2$ | $-CH_2-CH_2-N(COOCH_3)-CH_2-CH_2-$ |
| I.a.1.165 | $CON(CH_3)_2$ | $-CH_2-CH_2-N(CONHCH_3)-CH_2-CH_2-$ |
| I.a.1.166 | $CON(CH_3)_2$ | $-CH_2-CH_2-N(CON(CH_3)_2)-CH_2-CH_2-$ |
| I.a.1.167 | $CON(CH_3)_2$ | $-CH_2-CH_2-CH_2-CH_2-CH_2-CH_2-$ |
| I.a.1.168 | $CON(CH_3)_2$ | $-CH_2-O-CH_2-CH_2-O-CH_2-$ |

Most preference is likewise given to the compounds of the formula I.b, in particular to the compounds of the formulae I.b.1 to I.b.168, which differ from the corresponding compounds of the formulae I.a.1 to I.a.168 in that A is A1 where $R^8=CH_3$ and $R^9=CF_3$:

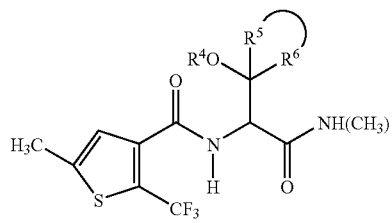

I.b

Most preference is likewise given to the compounds of the formula I.c, in particular to the compounds of the formulae I.c.1 to I.c.168, which differ from the corresponding compounds of the formulae I.a.1 to I.a.168 in that A is A2 where $R^8=H$ and $R^9=CF_3$:

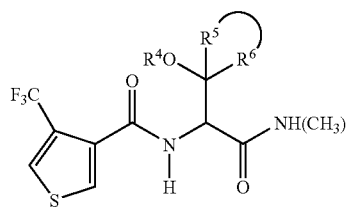

I.c

Most preference is likewise given to the compounds of the formula I.d, in particular to the compounds of the formulae I.d.1 to I.d.168, which differ from the corresponding compounds of the formulae I.a.1 to I.a.168 in that A is A3 where $R^8=H$ and $R^9=CF_3$:

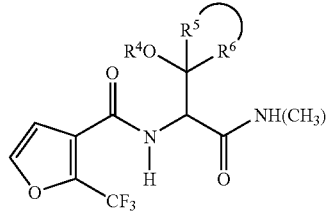

I.d

Most preference is likewise given to the compounds of the formula I.e, in particular to the compounds of the formulae I.e.1 to I.e.168, which differ from the corresponding compounds of the formulae I.a.1 to I.a.168 in that A is A3 where $R^8=CH_3$ and $R^9=CF_3$:

I.e

Most preference is likewise given to the compounds of the formula I.f, in particular to the compounds of the formulae I.f.1 to I.f.168, which differ from the corresponding compounds of the formulae I.a.1 to I.a.168 in that A is A4 where $R^8=H$ and $R^9=CF_3$:

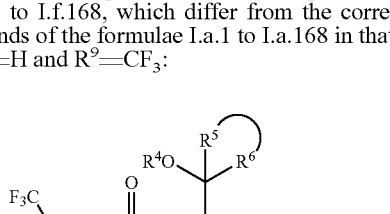

I.f

Most preference is likewise given to the compounds of the formula I.g, in particular to the compounds of the formulae I.g.1 to I.g.168, which differ from the corresponding compounds of the formulae I.a.1 to I.a.168 in that A is A5 where $R^{11}$=H, $R^9$=$CF_3$ and $R^{10}$=H:

I.g

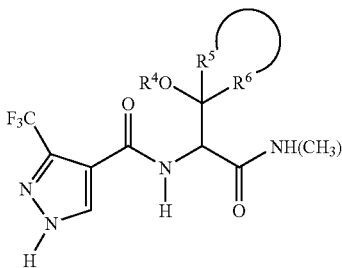

Most preference is likewise given to the compounds of the formula I.h, in particular to the compounds of the formulae I.h.1 to I.h.168, which differ from the corresponding compounds of the formulae I.a.1 to I.a.168 in that A is A5 where $R^{11}$=$CH_3$, $R^9$=$CF_3$ and $R^{10}$=H:

I.h

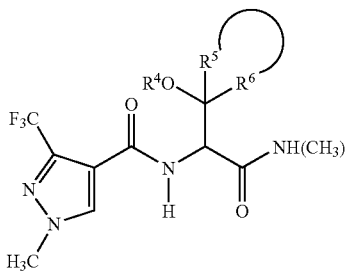

Most preference is likewise given to the compounds of the formula I.j, in particular to the compounds of the formulae I.j.1 to I.j.168, which differ from the corresponding compounds of the formulae I.a.1 to I.a.168 in that A is A8 where $R^8$=H and $R^9$=$CF_3$:

I.j

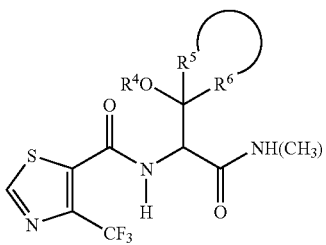

Most preference is likewise given to the compounds of the formula I.k, in particular to the compounds of the formulae I.k.1 to I.k.168, which differ from the corresponding compounds of the formulae I.a.1 to I.a.168 in that A is A8 where $R^8$=$CH_3$ and $R^9$=$CF_3$:

I.k

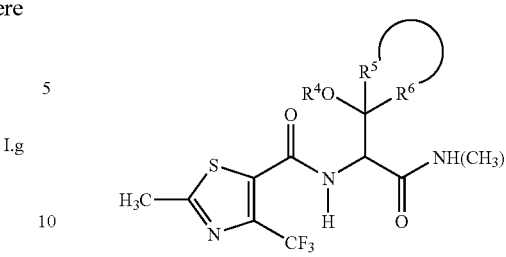

The heteroaroyl-substituted serineamides of the formula (I) can be obtained by different routes, for example by the following processes:

Process A

Serine derivatives of the formula (V) are initially reacted with heteroaryl acids/heteroaryl acid derivatives of the formula (IV) to give the corresponding heteroaroyl derivatives of the formula (III) which are then reacted with amines of the formula (II) to give the desired heteroaroyl-substituted serineamides of the formula (I):

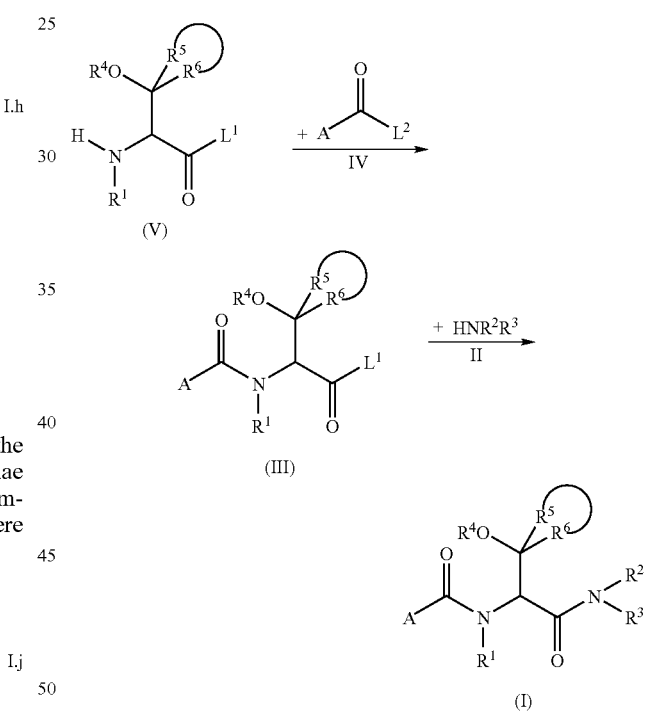

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl.

The reaction of the serine derivatives of the formula (V) with heteroaryl acids/heteroaryl acid derivatives of the formula (IV) where $L^2$ is hydroxyl to give heteroaroyl derivatives of the formula (III) is carried out in the presence of an activating reagent and a base, usually at temperatures of from 0° C. to the boiling point of the reaction mixture, preferably from 0° C. to 110° C., particularly preferably at room temperature, in an inert organic solvent [cf. Bergmann, E. D.; et al., J Chem Soc 1951, 2673; Zhdankin, V. V.; et al., Tetrahedron Lett. 2000, 41 (28), 5299-5302; Martin, S. F. et al., Tetrahedron Lett.1998, 39 (12), 1517-1520; Jursic, B. S. et al., Synth Commun 2001, 31 (4), 555-564; Albrecht, M. et al., Synthesis 2001, (3), 468-472; Yadav, L. D. S. et al., Indian J. Chem B. 41(3), 593-595(2002); Clark, J. E. et al., Synthesis (10), 891-894 (1991)].

Suitable activating reagents are condensing agents, such as, for example, polystyrene-bound dicyclohexylcarbodiimide, diisopropylcarbodiimide, carbonyldiimidazole, chloroformic esters, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)phosphoryl chloride (BOPCl) or sulfonyl chlorides, such as methanesulfonyl chloride, toluenesulfonyl chloride or benzenesulfonyl chloride.

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, and also dimethyl sulfoxide, dimethylformamide (DMF), dimethylacetamide (DMA) and N-methylpyrrolidone (NMP), or else in water; particular preference is given to methylene chloride, THF and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine and pyridine.

The bases are generally employed in equimolar amounts. However, they can also be used in excess or, if appropriate, as solvent.

The starting materials are generally reacted with one another in equimolar amounts. It may be advantageous to use an excess of (IV), based on (V).

The reaction mixtures are worked up in a customary manner, for example by mixing with water, separating the phases and, if appropriate, chromatographic purification of the crude products. Some of the intermediates and end products are obtained in the form of viscous oils which are purified or freed from volatile components under reduced pressure and at moderately elevated temperature. If the intermediates and end products are obtained as solids, purification can also be carried out by recrystallization or digestion.

The reaction of the serine derivatives of the formula (V) with heteroaryl acids/heteroaryl acid derivatives of the formula (IV) where $L^2$ is halogen, $C_1$-$C_6$-alkylcarbonyl, $C_1$-$C_6$-alkoxycarbonyl, $C_1$-$C_4$-alkylsulfonyl, phosphoryl or isoureyl to give heteroaroyl derivatives of the formula (III) is carried out in the presence of a base, usually at temperatures of from 0° C. to the boiling point of the reaction mixture, preferably at from 0° C. to 100° C., particularly preferably at room temperature, in an inert organic solvent [cf. Bergmann, E. D.; et al., J Chem Soc 1951, 2673; Zhdankin, V. V.; et al., Tetrahedron Lett. 2000, 41 (28), 5299-5302; Martin, S. F. et al., Tetrahedron Lett. 1998, 39 (12), 1517-1520; Jursic, B. S. et al., Synth Commun 2001, 31 (4), 555-564; Albrecht, M. et al., Synthesis 2001, (3), 468-472; Yadav, L. D. S. et al., Indian J. Chem B. 41(3), 593-595(2002); Clark, J. E. et al., Synthesis (10), 891-894 (1991)].

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, and also dimethyl sulfoxide, dimethylformamide (DMF), dimethylacetamide (DMA) and N-methylpyrrolidone (NMP), or else in water; particular preference is given to methylene chloride, THF and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine and pyridine.

The bases are generally employed in equimolar amounts. However, they can also be used in excess or, if appropriate, as solvent.

The starting materials are generally reacted with one another in equimolar amounts. It may be advantageous to use an excess of (IV), based on (V).

Work-up and isolation of the products can be carried out in a manner known per se.

It is, of course, also possible to initially react the serine derivatives of the formula (V) in an analogous manner with amines of the formula (II) to give the corresponding amides which are then reacted with heteroaryl acids/heteroaryl acid derivatives of the formula (IV) to give the desired heteroaroyl-substituted serineamides of the formula (I).

The serine derivatives of the formula (V) (for example where $L^1$=hydroxyl or $C_1$-$C_6$-alkoxy) required for preparing the heteroaroyl derivatives of the formula (III) are known from the literature, even in enantiomerically and diastereomerically pure form, or they can be prepared in accordance with the literature cited:
 by condensation of glycine enolate equivalents with cyclic ketones [Blaser, D. et al., Liebigs Ann. Chem. 10, 1067-1078 (1991); Seethaler, T. et al., Liebigs Ann. Chem. 1, 11-17 (1991); Weltenauer, G. et al., Gazz. Chim. Ital. 81, 162 (1951); Dalla Croce, P. et al., Heterocycles 52(3), 1337-1344 (2000); Van der Werf, A. W. et al., J. Chem. Soc. Chem. Commun. 100, 682-683 (1991); Caddick, S. et al., Tetrahedron 57 (30), 6615-6626 (2001); Owa, T. et al., Chem. Lett. 1, 83-86 (1988); Alker, D. et al., Tetrahedron 54 (22), 6089-6098 (1998); Rousseau, J. F. et al., J. Org. Chem. 63 (8), 2731-2737 (1998); Saeed, A. et al., Tetrahedron 48 (12), 2507-2514 (1992); Dong, L. et al., J. Org. Chem. 67 (14), 4759-4770 (2002)].

by aminohydroxylation of acrylic acid derivatives [Zhang, H. X. et al., Tetrahedron Asymmetr. 11(16), 3439-3447 (2000); Fokin, V. V. et al., Angew. Chem. Int. Edit. 40(18), 3455 (2001); Sugiyama, H. et al., Tetrahedron Lett. 43(19), 3489-3492 (2002); Bushey, M. L. et al., J. Org. Chem. 64(9), 2984-2985 (1999); Raatz, D. et al., Synlett (12), 1907-1910 (1999)].

by nucleophilic substitution of leaving groups in the 2-position of 3-hydroxypropionic acid derivatives [Owa, T. et al., Chem. Lett. (11), 1873-1874 (1988); Boger, D. L. et al., J. Org. Chem. 57(16), 4331-4333 (1992); Alcaide, B. et al., Tetrahedron Lett. 36(30), 5417-5420 (1995)].

by condensation of ketones with nucleophiles with formation of oxazolines and subsequent hydrolysis [Evans, D. A. et al., Angew. Chem. Int. Edit. 40(10), 1884-1888 (2001); Ito, Y. et al., Tetrahedron Lett. 26(47), 5781-5784 (1985); Togni, A. et al., J. Organomet. Chem. 381 (1), C21-5 (1990); Longmire, J. M. et al., Organometallics 17(20), 4374-4379 (1998); Suga, H. et al., J. Org. Chem. 58(26), 7397-7405 (1993)].

by oxidative cyclization of 2-acylaminopropionic acid derivatives to give oxazolines and subsequent hydrolysis (JP10101655).

The heteroaroyl acids/heteroaryl acid derivatives of the formula (IV) required for preparing the heteroaroyl derivatives of the formula (III) are commercially available or can be prepared analogously to procedures known from the literature from the corresponding halide by a Grignard reaction [for example A. Mannschuk et al., Angew. Chem. 100, 299 (1988)].

The reaction of the heteroaroyl derivatives of the formula (III) where $L^1$=hydroxyl or salts thereof with amines of the formula (II) to give the desired heteroaroyl-substituted serineamides of the formula (I) is carried out in the presence of an activating reagent and, if appropriate, in the presence of a base, usually at temperatures of from 0° C. to the boiling point of the reaction mixture, preferably at from 0° C. to 100° C., particularly preferably at room temperature, in an inert organic solvent [cf. Perich, J. W., Johns, R. B., J. Org. Chem. 53 (17), 4103-4105 (1988); Somlai, C. et al., Synthesis (3), 285-287 (1992); Gupta, A. et al., J. Chem. Soc. Perkin Trans. 2, 1911 (1990); Guan et al., J. Comb. Chem. 2, 297 (2000)].

Suitable activating reagents are condensing agents, such as, for example, polystyrene-bound dicyclohexylcarbodiimide, diisopropylcarbodiimide, carbonyldiimidazole, chloroformic esters, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)phosphoryl chloride (BOPCl) or sulfonyl chlorides, such as methanesulfonyl chloride, toluenesulfonyl chloride or benzenesulfonyl chloride.

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide (DMF), dimethylacetamide (DMA) and N-methylpyrrolidone (NMP), or else in water; particular preference is given to methylene chloride, THF, methanol, ethanol and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine, ethyldiisopropylamine, N-methylmorpholine and pyridine.

The bases are generally employed in catalytic amounts; however, they can also be employed in equimolar amounts, in excess or, if appropriate, as solvent.

The starting materials are generally reacted with one another in equimolar amounts. It may be advantageous to use an excess of (II), based on (III).

Work-up and isolation of the products can be carried out in a manner known per se.

The reaction of the heteroaroyl derivatives of the formula (III) where $L^1$=$C_1$-$C_6$-alkoxy with amines of the formula (II) to give the desired heteroaroyl-substituted serineamides of the formula (I) is usually carried out at temperatures of from 0° C. to the boiling point of the reaction mixture, preferably from 0° C. to 100° C., particularly preferably at room temperature, in an inert organic solvent, if appropriate in the presence of a base [cf. Kawahata, N. H. et al., Tetrahedron Lett. 43 (40), 7221-7223 (2002); Takahashi, K. et al., J. Org. Chem. 50 (18), 3414-3415 (1985); Lee, Y. et al., J. Am. Chem. Soc. 121 (36), 8407-8408 (1999)].

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide (DMF), dimethylacetamide (DMA) and N-methylpyrrolidone (NMP), or else in water; particular preference is given to methylene chloride, THF, methanol, ethanol and water.

It is also possible to use mixtures of the solvents mentioned.

If appropriate, the reaction can be carried out in the presence of a base. Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine, ethyldiisopropylamine, N-methylmorpholine and pyridine.

The bases are generally employed in catalytic amounts; however, they can also be employed in equimolar amounts, in excess or, if appropriate, as solvent.

The starting materials are generally reacted with one another in equimolar amounts. It may be advantageous to use an excess of (II), based on (III).

Work-up and isolation of the products can be carried out in a manner known per se.

The amines of the formula (II) required for preparing the heteroaroyl-substituted serineamides of the formula (I) are commercially available.

Process B

Heteroaroyl derivatives of the formula (III) where $R^4$=hydrogen can also be obtained by condensing acylated glycine derivatives of the formula (VIII) where the acyl group may be a cleavable protective group, such as benzyloxycarbonyl (cf. (VIIIa) where Σ=benzyl) or tert-butyloxycarbonyl (cf. (VIIIa) where Σ=tert-butyl), with carbonyl compounds (VII) to give the corresponding aldol products (VI). The protective group is then cleaved and the resulting serine derivative of the formula (V) where $R^4$=hydrogen is acylated using heteroaryl acid derivatives of the formula (IV).

Analogously, it is also possible to convert an acylated glycine derivative of the formula (VIII) where the acyl group is a substituted heteroaroyl radical (cf. VIIIb) in the presence of a base with a carbonyl compound VII into the heteroaroyl derivative III where $R^4$=hydrogen:

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl.

The reaction of the glycine derivatives (VIII) with carbonyl compounds (VII) to give the corresponding aldol product (VI) or heteroaroyl derivative (III) where $R^4$=hydrogen is usually carried out at temperatures of from −100° C. to the boiling point of the reaction mixture, preferably at from −80° C. to 20° C., particularly preferably at from −80° C. to −20° C., in an inert organic solvent in the presence of a base [cf. J.-F. Rousseau et al., J. Org. Chem. 63, 2731-2737 (1998)].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and tetrahydrofuran, and also dimethyl sulfoxide, dimethylformamide and dimethylacetamide, particularly preferably diethyl ether, dioxane and tetrahydrofuran.

It is also possible to use mixtures of the solvents mentioned.

Suitable bases are, in general, inorganic compounds, such as alkali metal and alkaline earth metal hydrides, such as lithium hydride, sodium hydride, potassium hydride and calcium hydride, alkali metal amides, such as lithium diisopropylamide and lithium hexamethyldisilazide, organometallic compounds, in particular alkali metal alkyls, such as methyllithium, butyllithium and phenyllithium, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to sodium hydride, lithium hexamethyldisilazide and lithium diisopropylamide.

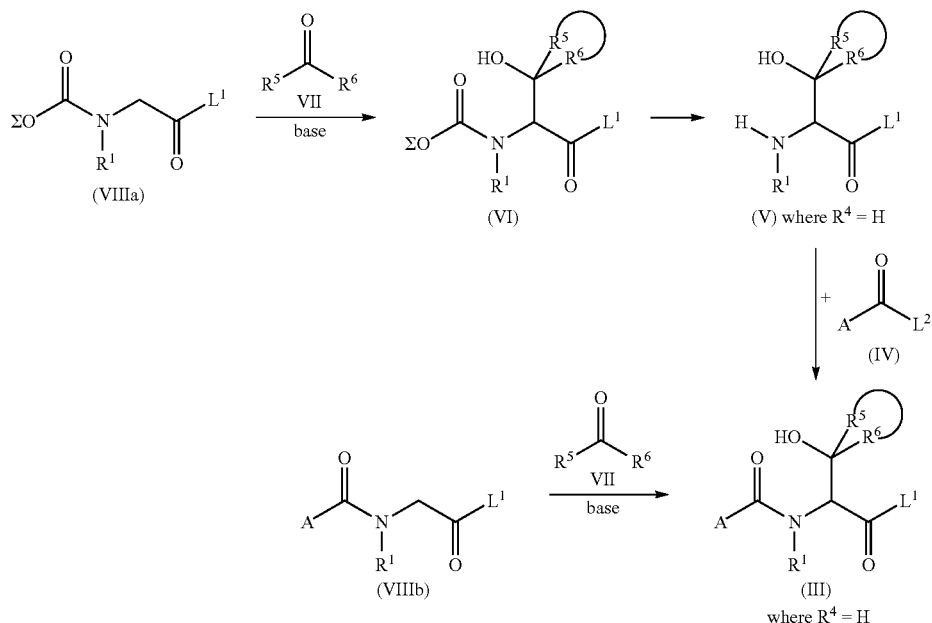

The bases are generally employed in equimolar amounts; however, they can also be used catalytically, in excess or, if appropriate, as solvents.

The starting materials are generally reacted with one another in equimolar amounts. It may be advantageous to employ an excess of base and/or carbonyl compounds (VII), based on the glycine derivatives (VIII).

Work-up and isolation of the products can be carried out in the manner known per se.

The glycine derivatives of the formula (VIII) required for preparing the compounds (I) are commercially available, known from the literature [for example H. Pessoa-Mahana et al., Synth. Comm. 32, 1437 (2002)] or can be prepared in accordance with the literature cited.

The protective group is cleaved off by methods known from the literature, giving serine derivatives of the formula (V) where $R^4$=hydrogen [cf. J.-F. Rousseau et al., J. Org. Chem. 63, 2731-2737 (1998); J. M. Andres, Tetrahedron 56, 1523 (2000)]; in the case of Σ=benzyl by hydrogenolysis, preferably using hydrogen and Pd/C in methanol; in the case of Σ=tert-butyl using acid, preferably hydrochloric acid in dioxane.

The reaction of the serine derivatives (V) where $R^4$=hydrogen with heteroaryl acids/heteroaryl acid derivatives (IV) to give heteroaroyl derivatives (III) where $R^4$=hydrogen is usually carried out analogously to the reaction mentioned in process A of the serine derivatives of the formula (V) with heteroaryl acids/heteroaryl acid derivatives of the formula (IV) to give heteroaroyl derivatives (III).

Analogously to process A, the heteroaroyl derivatives of the formula (III) where $R^4$=hydrogen can then be reacted with amines of the formula (II) to give the desired heteroaroyl-substituted serineamides of the formula (I) where $R^4$=hydrogen which can then be derivatized with compounds of the formula (IX) to give heteroaroyl-substituted serineamides of the formula (I) [cf., for example, Yokokawa, F. et al., Tetrahedron Lett. 42 (34), 5903-5908 (2001); Arrault, A. et al., Tetrahedron Lett. 43 (22), 4041-4044 (2002)].

It is also possible to derivatize the heteroaroyl derivatives of the formula (III) where $R^4$=hydrogen initially with compounds of the formula (IX) to give further heteroaroyl derivatives of the formula (III) [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)], followed by reaction with amines of the formula (II) analogously to process A, giving the desired heteroaroyl-substituted serineamides of the formula (I):

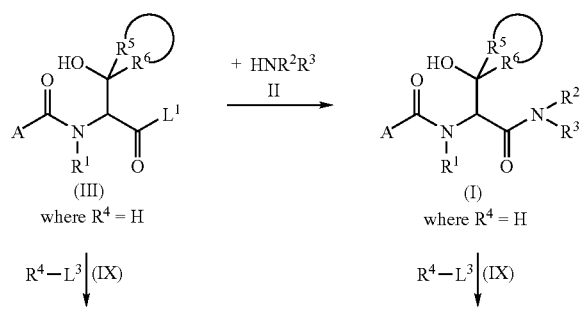

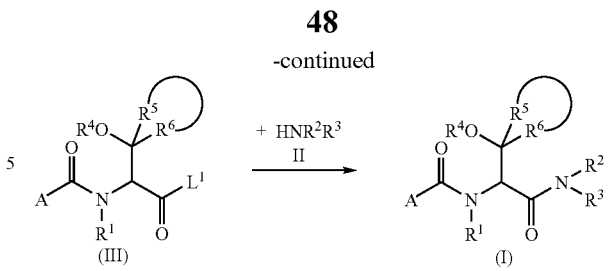

-continued $L^1$ is a nucleophilically displaceable leaving group, for example hydroxyl or $C_1$-$C_6$-alkoxy.

$L^3$ is a nucleophilically displaceable leaving group, for example halogen, hydroxyl, or $C_1$-$C_6$-alkoxy.

The reaction of the heteroaroyl derivatives of the formula (III) (where, if appropriate, $R^4$=hydrogen) with amines of the formula (II) to give heteroaroyl-substituted serineamides of the formula (I) (where, if appropriate, $R^4$=hydrogen) is usually carried out analogously to the reaction of the heteroaroyl derivatives of the formula (III) with amines of the formula (II) described in process A.

The reaction of the heteroaroyl derivatives of the formula (III) where $R^4$=hydrogen or of the heteroaroyl-substituted serineamides of the formula (I) where $R^4$=hydrogen with compounds of the formula (IX) to give heteroaroyl derivatives of the formula (III) or heteroaroyl-substituted serineamides of the formula (I) is usually carried out at temperatures of from 0° C. to 100° C., preferably from 10° C. to 50° C., in an inert organic solvent in the presence of a base [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide, particularly preferably dichloromethane, tert-butyl methyl ether, dioxane and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to sodium hydroxide, sodium hydride and triethylamine.

The bases are generally employed in equimolar amounts; however, they can also be employed catalytically, in excess or, if appropriate, as solvents.

The starting materials are generally reacted with one another in equimolar amounts. It may be advantageous to use an excess of base and/or (IX), based on (III) or (I).

Work-up and isolation of the products can be carried out in a manner known per se.

The required compounds of the formula (VIII) are commercially available.

Process C

Heteroaroyl derivatives of the formula (III) where $R^4$=hydrogen and $R^6$=—C(OH)R'R" can also be obtained by dihydroxylating vinylglycines of the formula (XIV) with an oxidizing agent such as osmium tetroxide or permanganate:

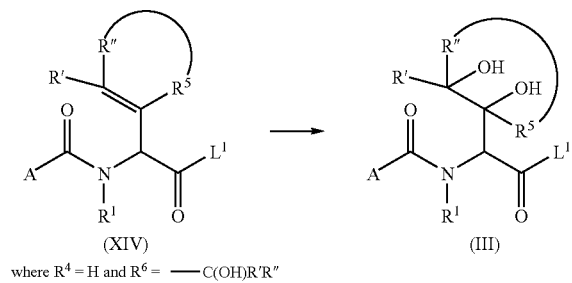

where $R^4$ = H and $R^6$ = —C(OH)R'R"

$L^1$ is a nucleophilically displaceable leaving group, for example hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R" is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

This reaction is usually carried out at temperatures of from −78° C. to the boiling point of the reaction mixture, preferably from −10° C. to 120° C., especially preferably from 0° C. to 50° C., in an inert organic solvent, if appropriate in the presence of a reoxidizing agent, such as, for example, N-methylmorpholine N-oxide (D. Johnson et al., Tetrahedron 2000, 56, 5, 781).

Suitable solvents are halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide, dimethylacetamide and water; particularly preferably acetone or water.

It is also possible to use mixtures of the solvents mentioned.

The starting materials are generally reacted with one another in equimolar amounts. It may be advantageous to employ an excess of oxidizing agent, based on XIV.

The reaction mixtures are worked up in a customary manner, for example by mixing with water, separating the phases and, if appropriate, chromatographic purification of the crude products. Some of the intermediates and end products are obtained in the form of viscous oils which can be purified or freed from volatile components under reduced pressure and at moderately elevated temperature. If the intermediates and end products are obtained as solids, purification can also be carried out by recrystallization or digestion.

The vinylglycines of the formula (XIV) required for preparing the heteroaryl derivatives of the formula (III) where $R^4$=hydrogen and $R^6$=—C(OH)R'R" are known from the literature [D. B. Berkowitz et al., J. Org. Chem. 2000, 65, 10, 2907; M. Koen et al., J. Chem. Soc. Perkin I 1997, 4, 487], or they can be prepared in accordance with the literature cited.

The heteroaroyl derivatives of the formula (III) where $R^4$=hydrogen and $R^6$=—C(OH)R'R" can then be reacted with amines of the formula (II) analogously to process A to give the desired heteroaroyl-substituted serineamides of the formula (I) where $R^4$=hydrogen and $R^6$=—C(OH)R'R", which can then be derivatized with compounds of the formula (IX) to give heteroaroyl-substituted serineamides of the formula (I) where $R^6$=—C(OR$^4$)R'R" [cf., for example, Yokokawa, F. et al., Tetrahedron Lett. 42 (34), 5903-5908 (2001); Arrault, A. et al., Tetrahedron Lett. 43(22), 4041-4044 (2002)];

it is also possible to derivatize the heteroaroyl derivatives of the formula (III) where $R^4$=hydrogen initially with compounds of the formula (IX) to give further heteroaroyl derivatives of the formula (III) where $R^6$=—C(OR$^4$)R'R" analogously to process B [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)]; followed by reaction analogously to process A with amines of the formula (II) to give the desired heteroaroyl-substituted serineamides of the formula (I) where $R^6$=—C(OR$^4$)R'R":

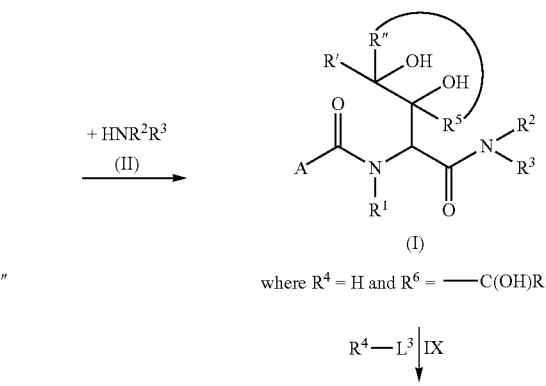

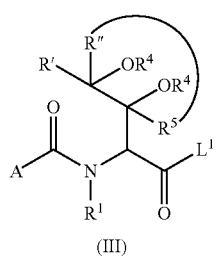 + HNR²R³ (II) → 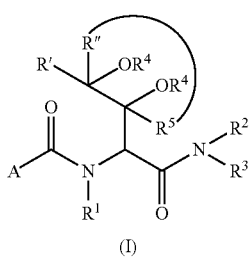

(III) where R⁶ = —C(OR4)R'R''

(I) where R⁶ = —C(OR⁴)R'R''

$L^1$ is a nucleophilically displaceable leaving group, for example hydroxyl or $C_1$-$C_6$-alkoxy.

$L^3$ is a nucleophilically displaceable leaving group, for example halogen, hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R'' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

Process D

Heteroaroyl derivatives of the formula (III) where $R^4$=hydrogen and $R^6$=—C(Nuc)R'R'' can also be obtained by epoxidizing vinylglycines of the formula (XIV) with an epoxidizing agent to give epoxyglycines of the formula (XV), followed by a nucleophilic epoxide opening:

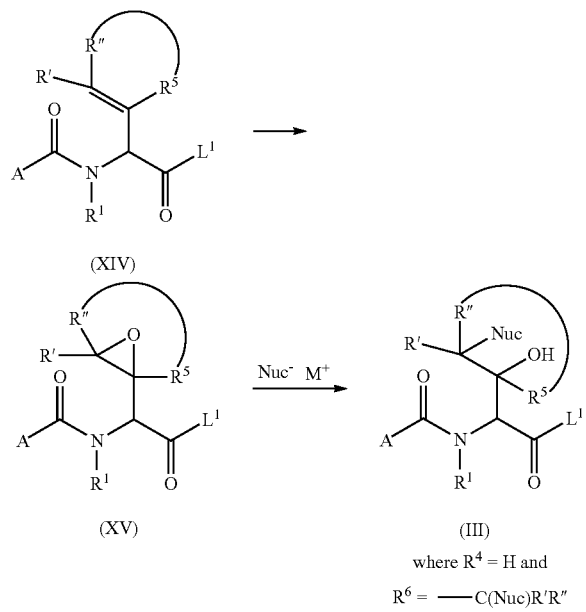

where $R^4$ = H and
$R^6$ = —C(Nuc)R'R''

$L^1$ is a nucleophilically displaceable leaving group, for example hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R'' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

Nuc⁻M⁺ is, for example, a thiolate, such as, for example, sodium thiophenolate, an alkoxide, such as potassium phenoxide, or an amide, such as sodium imidazolate.

The epoxidation is usually carried out at temperatures of from −78° C. to the boiling point of the reaction mixture, preferably from −20° C. to 50° C., especially preferably from 0° C. to 30° C., in an inert organic solvent [cf. P. Meffre et al., Tetrahedron Lett. 1990, 31, 16, 2291].

Suitable for use as epoxidizing agents are peracids and peroxides (for example meta-chloroperbenzoic acid, peracetic acid, dimethyldioxirane, hydrogen peroxide).

Suitable solvents are halogenated hydrocarbons, such as methylene chloride, chloroform and chlorobenzene, alcohols, such as methanol, ethanol, n-propanol, isopropanol, n-butanol and tert-butanol, and also water, particularly preferably halogenated hydrocarbons and water.

It is also possible to use mixtures of the solvents mentioned.

The starting materials are generally reacted with one another in equimolar amounts. It may be advantageous to use an excess of epoxidizing agent, based on (XIV).

The reaction mixtures are worked up in a customary manner, for example by mixing with water, separating the phases and, if appropriate, chromatographic purification of the crude products. Some of the intermediates and end products are obtained in the form of viscous oils which can be purified or freed from volatile components under reduced pressure and at moderately elevated temperature. If the intermediates and end products are obtained as solids, purification can also be carried out by recrystallization or by digestion.

The vinylglycines of the formula (XIV) required for preparing the heteroaroyl derivatives of the formula (III) where $R^4$=hydrogen and $R^6$=—C(OH)R'R'' are known from the literature [D. B. Berkowitz et al., J. Org. Chem. 2000, 65, 10, 2907; M. Koen et al., J. Chem. Soc. Perkin 1 1997, 4, 487], or they can be prepared in accordance with the literature cited.

The epoxide opening is usually carried out at temperatures of from −78° C. to the boiling point of the reaction mixture, preferably from −20° C. to 100° C., especially preferably from 0° C. to 50° C., in an inert organic solvent, if appropriate in the presence of a catalyst [cf. P. Meffre et al., Tetrahedron Lett. 1990, 31, 16, 2291; M. R. Paleo et al., J. Org. Chem. 2003, 68, 1, 130].

Suitable solvents are alcohols, such as methanol, ethanol, n-propanol, isopropanol, n-butanol and tert-butanol and also dimethyl sulfoxide, dimethylformamide and dimethylacetamide and water, particularly preferably methanol and water.

It is also possible to use mixtures of the solvents mentioned.

Suitable for use as acidic catalysts are Lewis acids, such as boron trifluoride, aluminum trichloride, iron(III) chloride, tin(IV) chloride, titanium(IV) chloride, zinc(II) chloride and magnesium perchlorate.

The catalyst is employed in a customary manner in a ratio of from 1 to 100 mol %, preferably from 1 to 10 mol %, based on the compound (XV).

The starting materials are generally reacted with one another in equimolar amounts. It may be advantageous to use an excess of Nuc⁻M⁺, based on (XV).

The reaction mixtures are worked up in a customary manner, for example by mixing with water, separating the phases and, if appropriate, chromatographic purification of the crude products. Some of the intermediates and end products are obtained in the form of viscous oils which are purified or freed from volatile components under reduced pressure and at moderately elevated temperature. If the intermediates and end products are obtained as solids, purification can also be carried out by recrystallization or digestion.

The heteroaroyl derivatives of the formula (III) where $R^4$=hydrogen and $R^6$=—C(Nuc)R'R" can then be reacted with amines of the formula (II) analogously to process A to give the desired benzoyl-substituted serineamides of the formula (I) where $R^4$=hydrogen and $R^6$=—C(Nuc)R'R", which can then be derivatized with compounds of the formula (IX) to give heteroaroyl-substituted serineamides of the formula (I) where $R^6$=—C(Nuc)R'R" [cf., for example, Yokokawa, F. et al., Tetrahedron Lett. 42 (34), 5903-5908 (2001); Arrault, A. et al., Tetrahedron Lett. 43(22), 4041-4044 (2002)].

It is also possible to derivatize the heteroaroyl derivatives of the formula (III) where $R^4$=hydrogen initially with compounds of the formula (IX) to give further benzoyl derivatives of the formula (III) where $R^6$=—C(Nuc)R'R" analogously to process B [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)], followed by reaction analogously to process A with amines of the formula (II) to give the desired heteroaroyl-substituted serineamides of the formula (I) where $R^6$=—C(Nuc)R'R":

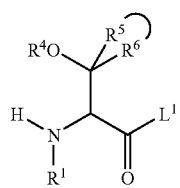

(V)

$L^1$ is a nucleophilically displaceable leaving group, for example hydroxyl or $C_1$-$C_6$-alkoxy.

$L^3$ is a nucleophilically displaceable leaving group, for example halogen, hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R" is hydrogen, $C_1$-$C_6$-akyl, $C_1$-$C_6$-haloalkyl, $C_1$-$C_6$-hydroxyalkyl, phenyl or $C_1$-$C_6$-alkoxycarbonyl.

Nuc$^-$M$^+$ is, for example, a thiolate, such as, for example, sodium thiophenolate, an alkoxide, such as potassium phenoxide, or an amide, such as sodium imidazolate.

Heteroaroyl derivatives of the formula (III)

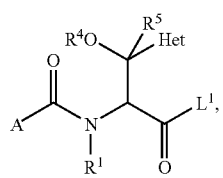

(III)

where A, $R^1$ and $R^4$, $R^5$ and $R^6$ are as defined above and $L^1$ is hydroxyl or $C_1$-$C_6$-alkoxy also form part of the subject-matter of the present invention.

The particularly preferred embodiments of the intermediates with respect to variables correspond to those of the radicals A, $R^1$ and $R^4$ to $R^6$ of formula (I).

Particular preference is given to heteroaroyl derivatives of the formula (III) in which A is 5- or 6-membered heteroaryl selected from the group consisting of thienyl, furyl, pyrazolyl, imidazolyl, thiazolyl, oxazolyl and pyridyl;

where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;

$R^1$ is hydrogen;

$R^4$ is hydrogen, formyl, $C_1$-$C_4$-alkylcarbonyl, $C_1$-$C_4$-alkylaminocarbonyl, di-($C_1$-$C_4$-alkyl)aminocarbonyl, phenylaminocarbonyl, N—($C_1$-$C_4$-alkyl)-N-(phenyl)aminocarbonyl, $SO_2CH_3$, $SO_2CF_3$ or $SO_2(C_6H_5)$;

$R^5$ and $R^6$ together with the carbon atom to which they are attached are a 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom, 2 oxygen or sulfur atoms, where the ring is unsubstituted or substituted by 1 to 3, in the case of halogen also up to the maximum possible number, substituents from the group consisting of halogen, $C_1$-$C_6$-alkyl, hydroxyl, $C_1$-$C_6$-alkoxy, formyl, $C_1$-$C_6$-alkyl-carbonyl, $C_1$-$C_6$-alkoxycarbonyl, $C_1$-$C_6$-alkylaminocarbonyl, di-($C_1$-$C_6$-alkyl)-aminocarbonyl, alkylsulfonylamino, carbonyl, alkoxyimino, where the alkyl and alkoxy radicals mentioned may be partially or fully halogenated and/or may carry one to three of the following groups: cyano, hydroxyl, $C_1$-$C_4$-alkoxy, phenyl, partially or fully halogenated, and the ring is monocyclic or fused to a further 3- to 6-membered saturated or partially unsaturated ring which is carbocyclic or contains 1 or 2 nitrogen atoms, 0 or 1 nitrogen atom and 1 oxygen atom or sulfur atom, 2 oxygen atoms or sulfur atoms, 0 or 1 nitrogen atom and 1 oxygen atom and 1 sulfur atom, where the fused ring is unsubstituted or substituted by 1 to 3, in the case of halogen also up to the maximum possible number, substituents from the group consisting of halogen, $C_1$-$C_6$-alkyl, $C_1$-$C_6$-haloalkyl and $C_1$-$C_6$-alkoxy, or the ring is bridged by a 1- to 3-membered saturated or unsaturated chain which contains no heteroatoms or contains 1 nitrogen atom, 0 or 1 nitrogen atom and 1 oxygen atom or 1 sulfur atom, where the bridge is unsubstituted or substituted by 1 to 3, in the case of halogen also up to the maximum possible number, substituents from the group consisting of halogen, $C_1$-$C_6$-alkyl, hydroxyl and $C_1$-$C_6$-alkoxy.

The examples below serve to illustrate the invention.

PREPARATION EXAMPLES

Example 1

Dimethylcarbamic acid 1-{methylcarbamoyl-[(1-methyl-3-trifluoromethyl-1H-pyrazole-4-carbonyl)amino]methyl}cyclobutyl ester

1.1 Ethyl[(1-methyl-3-trifluoromethyl-1H-pyrazole-4-carbonyl)amino]acetate

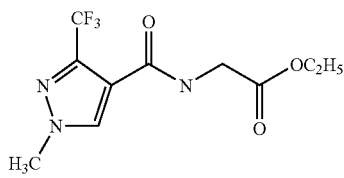

3.63 g (25.8 mmol) of glycine ethyl ester hydrochloride were dissolved in $CH_2Cl_2$, THF, 5.00 g (25.8 mmol) of 1-methyl-3-trifluoromethyl-4-carboxylic acid and 7.82 g of triethylamine (77.3 mmol) were added at RT and 6.56 g (25.8 mmol) of bis-(2-oxo)-3-oxazolidinyl)phosphonyl chloride were added at 0° C. The mixture was stirred at 0° C. for 3 h and then at RT for 16 h. The solvents were then removed, the residue was taken up in ethyl acetate, washed and dried and the solvent was removed. This gave 3.88 g (54% of theory) of the title compound as a red oil.

$^1$H-NMR (DMSO): δ=1.20 (t, 3H); 3.95 (s, 6H); 4.15 (q, 2H); 8.35 (s, 1H); 8.65 (t, 1H).

1.2 Ethyl(1-hydroxycyclobutyl)-[(3-trifluoromethyl-1H-pyrazole-4-carbonyl)amino]-acetate (Cpd.3.1)

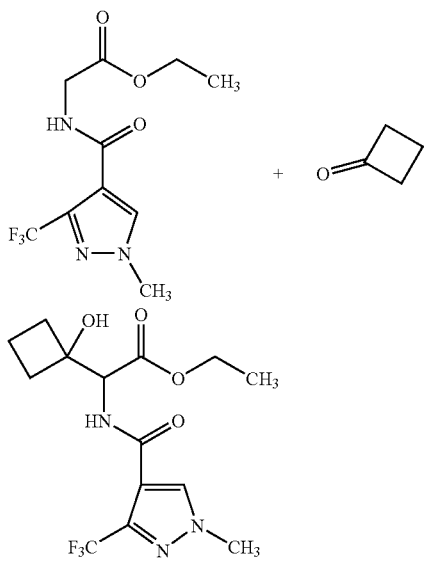

23.0 ml of hexamethyldisilazane (mmol) were dissolved in 200 ml of THF, and 46 ml of 2.5M (115 mmol) of butyllithium solution in hexane were added dropwise at −78° C. After 30 min, 7.90 g (22.3 mmol) of ethyl [(1-methyl-3-trifluoromethyl-1H-pyrazole-4-carbonyl)amino]acetate, dissolved in 50 ml of THF, were added dropwise, and the mixture was stirred at −78° C. for 1.5 h. 3.0 g (42.8 mmol) of cyclobutanone and 4.14 g (29.2 mmol) of $BF_3$-etherate, dissolved in 50 ml of THF, were added dropwise, and the mixture was stirred at −78° C. for 2 h, at −50° C. for 1 h and at 0° C. for 1 h. 100 ml of saturated $NH_4Cl$ solution were added dropwise, and the mixture was stirred for 30 min. The organic phase was separated off and the solvents were removed under reduced pressure. This gave 9.88 g (100%) of colorless crystals which were reacted without further purification.

1H-NMR (DMSO): 1.2 (t, 3H); 1.5-2.2 (m, 6H); 4.1 (m, 2H); 4.6 (d, 1H); 5.4 (s, 1H); 8.0 (d, 1H); 8.5 (s, 1H)

MS (M+H): 350

The intermediates of formula (III) listed in Table 3 below were prepared in an analogous manner.

1.3 N-[(1-hydroxycyclobutyl)methylcarbamoylmethyl]-1-methyl-3-trifluoromethyl-1H-pyrazole-4-carboxamide

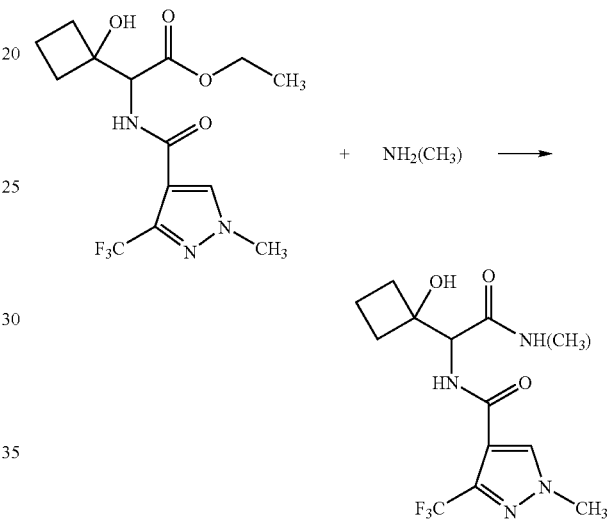

9.00 g (25.8 mmol) of ethyl[(1-methyl-3-trifluoromethyl-1H-pyrazole-4-carbonyl)-amino]acetate were dissolved in 400 ml of methanol, and methylamine was introduced at 0° C. for 1 h. The resulting precipitate was filtered off with suction and washed with pentane. This gave 4.7 g of colorless crystals.

1H-NMR (DMSO): 1.5-2.1 (m, 5H); 2.4 (m, 1H); 2.6(d, 3H); 3.9 (s, 3H); 4.5 (d, 1H); 5.3 (s, 1H); 7.8 (s, 1H); 7.9 (d, 1H); 8.5 (s, 1H)

MS (M+H):335

MP: 210° C.

1.4 Dimethylcarbamic acid 1-{methylcarbamoyl-[(1-methyl-3-trifluoromethyl-1H-pyrazol-4-carbonyl)amino]methyl}cyclobutyl ester

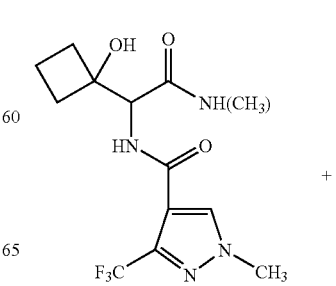

-continued

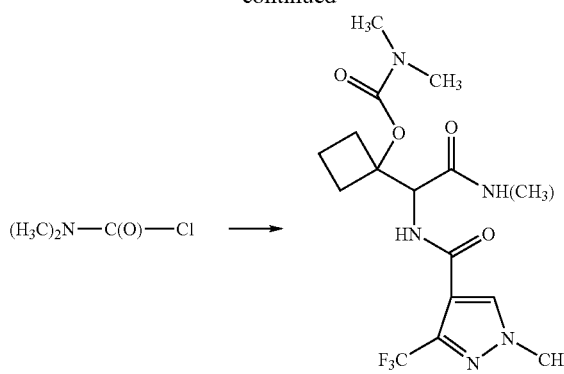

600 mg (1.79 mmol) of N-[(1-hydroxycyclobutyl)methyl-carbamoylmethyl]-1-methyl-3-trifluoromethyl-1H-pyrazole-4-carboxamide were dissolved in 30 ml of THF, and 0.130 g (2.75 mmol) of sodium hydride (60% in mineral oil) was added. 300 mg (2.79 mmol) of dimethylcarbamoyl chloride were added, and the mixture was stirred at 23° C. for 15 h. The mixture was concentrated, the residue was taken up in ethyl acetate and the mixture was washed with water, dried with $Na_2SO_4$ and reconcentrated. This gave 650 mg (1.62 mmol, 90% of theory) of colorless crystals.

1H-NMR (DMSO): 1.2 (m, 1H); 1.6 (m, 1H); 1.8 (m, 1H); 2.4 (m, 3H); 2.6 (d, 3H); 2.8 (2s, 6H); 3.9 (s, 3H); 8.0 (m, 1H); 8.3 (d, 1H); 8.4 (s, 1H)

MS (M+H): 406

MP: 190° C.

The compounds of formula (I) listed in Table 2 below were prepared in an analogous manner.

TABLE 2

(I)

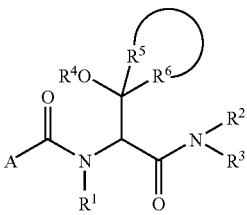

| No. | A | $R^1$ | $R^2$ | $R^3$ | $R^4$ |
|---|---|---|---|---|---|
| 2.1 | 1-$CH_3$-3-$CF_3$-4-pyrazolyl | H | H | $CH_3$ | H |
| 2.2 | 1-$CH_3$-3-$CF_3$-4-pyrazolyl | H | H | $CH_3$ | H |
| 2.3 | 1-$CH_3$-3-$CF_3$-4-pyrazolyl | H | H | $CH_3$ | (CO)N($CH_3$)$_2$ |
| 2.4 | 1-$CH_3$-3-$CF_3$-4-pyrazolyl | H | H | $CH_3$ | (CO)NH($CH_3$) |
| 2.5 | 1-$CH_3$-3-$CF_3$-4-pyrazolyl | H | H | $CH_3$ | (CO)$NH_2$ |
| 2.6 | 1-$CH_3$-3-$CF_3$-4-pyrazolyl | H | H | $CH_3$ | H |
| 2.7 | 1-$CH_3$-3-$CF_3$-4-pyrazolyl | H | H | $CH_3$ | (CO)N($CH_3$)$_2$ |
| 2.8 | 1-$CH_3$-3-$CF_3$-4-pyrazolyl | H | H | $CH_3$ | (CO)N($CH_3$)$_2$ |
| 2.9 | 1-$CH_3$-3-$CF_3$-4-pyrazolyl | H | H | $CH_3$ | (CO)N($CH_3$)$_2$ |
| 2.10 | 1-$CH_3$-3-$CF_3$-4-pyrazolyl | H | H | $CH_3$ | H |
| 2.11 | 1-$CH_3$-3-$CF_3$-4-pyrazolyl | H | H | $CH_3$ | H |
| 2.12 | 1-$CH_3$-3-$CF_3$-4-pyrazolyl | H | H | $CH_3$ | (CO)N($CH_3$)$_2$ |
| 2.13 | 1-$CH_3$-3-$CF_3$-4-pyrazolyl | H | H | $CH_3$ | (CO)$NH_2$ |
| 2.14 | 1-$CH_3$-3-$CF_3$-4-pyrazolyl | H | H | $CH_3$ | H |
| 2.15 | 1-$CH_3$-3-$CF_3$-4-pyrazolyl | H | H | $CH_3$ | (CO)N($CH_3$)$_2$ |
| 2.16 | 1-$CH_3$-3-$CF_3$-4-pyrazolyl | H | H | $CH_3$ | H |
| 2.17 | 1-$CH_3$-3-$CF_3$-4-pyrazolyl | H | H | $CH_3$ | H |
| 2.18 | 1-$CH_3$-3-$CF_3$-4-pyrazolyl | H | H | $CH_3$ | H |
| 2.19 | 1-$CH_3$-3-$CF_3$-4-pyrazolyl | H | H | $CH_3$ | (CO)$CH_3$ |
| 2.20 | 1-$CH_3$-3-$CF_3$-4-pyrazolyl | H | H | $CH_3$ | (CO)NH($CH_3$) |
| 2.21 | 1-$CH_3$-3-$CF_3$-4-pyrazolyl | H | H | $CH_3$ | H |
| 2.22 | 1-$CH_3$-3-$CF_3$-4-pyrazolyl | H | H | $CH_3$ | (CO)N($CH_3$)$_2$ |
| 2.23 | 1-$CH_3$-3-$CF_3$-4-pyrazolyl | H | H | $CH_3$ | H |
| 2.24 | 1-$CH_3$-3-$CF_3$-4-pyrazolyl | H | H | $CH_3$ | (CO)NH($CH_3$) |
| 2.25 | 1-$CH_3$-3-$CF_3$-4-pyrazolyl | H | H | $CH_3$ | H |
| 2.26 | 1-$CH_3$-3-$CF_3$-4-pyrazolyl | H | H | $CH_3$ | H |
| 2.27 | 1-$CH_3$-3-$CF_3$-4-pyrazolyl | H | H | $CH_3$ | (CO)NH($CH_3$) |
| 2.28 | 1-$CH_3$-3-$CF_3$-4-pyrazolyl | H | H | $CH_3$ | (CO)NH($CH_3$) |
| 2.29 | 1-$CH_3$-3-$CF_3$-4-pyrazolyl | H | H | $CH_3$ | H |
| 2.30 | 1-$CH_3$-3-$CF_3$-4-pyrazolyl | H | H | $CH_3$ | H |
| 2.31 | 1-$CH_3$-3-$CF_3$-4-pyrazolyl | H | H | $CH_3$ | (CO)NH($CH_3$) |
| 2.32 | 1-$CH_3$-3-$CF_3$-4-pyrazolyl | H | H | $CH_3$ | (CO)N($CH_3$)$_2$ |
| 2.33 | 1-$CH_3$-3-$CF_3$-4-pyrazolyl | H | H | $CH_3$ | H |
| 2.34 | 1-$CH_3$-3-$CF_3$-4-pyrazolyl | H | H | $CH_3$ | (CO)N($CH_3$)$_2$ |
| 2.35 | 1-$CH_3$-3-$CF_3$-4-pyrazolyl | H | H | $CH_3$ | (CO)$CH_3$ |
| 2.36 | 1-$CH_3$-3-$CF_3$-4-pyrazolyl | H | H | $CH_3$ | (CO)N($CH_3$)$_2$ |
| 2.37 | 1-$CH_3$-3-$CF_3$-4-pyrazolyl | H | H | $CH_3$ | (CO)NH($CH_3$) |
| 2.38 | 1-$CH_3$-3-$CF_3$-4-pyrazolyl | H | H | $CH_3$ | (CO)$NH_2$ |
| 2.39 | 1-$CH_3$-3-$CF_3$-4-pyrazolyl | H | H | $CH_3$ | (CO)NH($CH_3$) |
| 2.40 | 1-$CH_3$-3-$CF_3$-4-pyrazolyl | H | H | $CH_3$ | H |
| 2.41 | 1-$CH_3$-3-$CF_3$-4-pyrazolyl | H | H | $CH_3$ | H |
| 2.42 | 1-$CH_3$-3-$CF_3$-4-pyrazolyl | H | H | $CH_3$ | H |
| 2.43 | 1-$CH_3$-3-$CF_3$-4-pyrazolyl | H | H | $CH_3$ | (CO)NH($CH_3$) |
| 2.44 | 1-$CH_3$-3-$CF_3$-4-pyrazolyl | H | H | $CH_3$ | (CO)N($CH_3$)$_2$ |

TABLE 2-continued

| | | | | | |
|---|---|---|---|---|---|
| 2.45 | 1-CH₃-3-CF₃-4-pyrazolyl | H | H | CH₃ | (CO)NH₂ |
| 2.46 | 1-CH₃-3-CF₃-4-pyrazolyl | H | H | CH₃ | (CO)N(CH₃)₂ |
| 2.47 | 1-CH₃-3-CF₃-4-pyrazolyl | H | H | CH₃ | (CO)NH₂ |
| 2.48 | 1-CH₃-3-CF₃-4-pyrazolyl | H | H | CH₃ | (CO)N(CH₃)₂ |
| 2.49 | 1-CH₃-3-CF₃-4-pyrazolyl | H | H | CH₃ | (CO)NH(CH₃) |
| 2.50 | 1-CH₃-3-CF₃-4-pyrazolyl | H | H | CH₃ | (CO)N(CH₃)₂ |
| 2.51 | 1-CH₃-3-CF₃-4-pyrazolyl | H | H | CH₃ | (CO)NH(CH₃) |
| 2.52 | 1-CH₃-3-CF₃-4-pyrazolyl | H | H | CH₃ | (CO)CH₃ |
| 2.53 | 1-CH₃-3-CF₃-4-pyrazolyl | H | H | CH₃ | (CO)N(CH₃)₂ |
| 2.54 | 1-CH₃-3-CF₃-4-pyrazolyl | H | H | CH₃ | H |
| 2.55 | 1-CH₃-3-CF₃-4-pyrazolyl | H | H | CH₃ | (CO)N(CH₃)₂ |
| 2.56 | 1-CH₃-3-CF₃-4-pyrazolyl | H | H | CH₃ | H |
| 2.57 | 1-CH₃-3-CF₃-4-pyrazolyl | H | H | CH₃ | H |
| 2.58 | 1-CH₃-3-CF₃-4-pyrazolyl | H | H | CH₃ | H |
| 2.59 | 1-CH₃-3-CF₃-4-pyrazolyl | H | H | CH₃ | H |
| 2.60 | 1-CH₃-3-CF₃-4-pyrazolyl | H | H | CH₃ | (CO)N(CH₃)₂ |
| 2.61 | 1-CH₃-3-CF₃-4-pyrazolyl | H | H | CH₃ | (CO)N(CH₃)₂ |
| 2.62 | 1-CH₃-3-CF₃-4-pyrazolyl | H | H | CH₃ | (CO)N(CH₃)₂ |
| 2.63 | 1-CH₃-3-CF₃-4-pyrazolyl | H | H | CH₃ | (CO)N(CH₃)₂ |
| 2.64 | 1-CH₃-3-CF₃-4-pyrazolyl | H | H | CH₃ | (CO)N(CH₃)₂ |
| 2.65 | 1-CH₃-3-CF₃-4-pyrazolyl | H | H | CH₃ | H |
| 2.66 | 1-CH₃-3-CF₃-4-pyrazolyl | H | H | CH₃ | H |
| 2.67 | 1-CH₃-3-CF₃-4-pyrazolyl | H | H | CH₃ | (CO)CH₃ |
| 2.68 | 1-CH₃-3-CF₃-4-pyrazolyl | H | H | CH₃ | (CO)N(CH₃)₂ |
| 2.69 | 1-CH₃-3-CF₃-4-pyrazolyl | H | H | CH₃ | (CO)NH(CH₃) |
| 2.70 | 1-CH₃-3-CF₃-4-pyrazolyl | H | H | CH₃ | (CO)N(CH₃)₂ |
| 2.71 | 1-CH₃-3-CF₃-4-pyrazolyl | H | H | CH₃ | (CO)N(CH₃)₂ |
| 2.72 | 1-CH₃-3-CF₃-4-pyrazolyl | H | H | CH₃ | (CO)N(CH₃)₂ |
| 2.73 | 1-CH₃-3-CF₃-4-pyrazolyl | H | H | CH₃ | (CO)NH(CH₃) |
| 2.74 | 1-CH₃-3-CF₃-4-pyrazolyl | H | H | CH₃ | (CO)N(CH₃)₂ |
| 2.75 | 1-CH₃-3-CF₃-4-pyrazolyl | H | H | CH₃ | (CO)N(CH₃)₂ |
| 2.76 | 1-CH₃-3-CF₃-4-pyrazolyl | H | H | CH₃ | H |
| 2.77 | 1-CH₃-3-CF₃-4-pyrazolyl | H | H | CH₃ | H |
| 2.78 | 1-CH₃-3-CF₃-4-pyrazolyl | H | H | CH₃ | H |
| 2.79 | 1-CH₃-3-CF₃-4-pyrazolyl | H | H | CH₃ | (CO)N(CH₃)₂ |
| 2.80 | 1-CH₃-3-CF₃-4-pyrazolyl | H | H | CH₃ | (CO)N(CH₃)₂ |
| 2.81 | 1-CH₃-3-CF₃-4-pyrazolyl | H | H | CH₃ | (CO)N(CH₃)₂ |
| 2.82 | 1-CH₃-3-CF₃-4-pyrazolyl | H | H | CH₃ | (CO)N(CH₃)₂ |
| 2.83 | 1-CH₃-3-CF₃-4-pyrazolyl | H | H | CH₃ | (CO)N(CH₃)₂ |
| 2.84 | 1-CH₃-3-CF₃-4-pyrazolyl | H | H | CH₃ | (CO)N(CH₃)₂ |
| 2.85 | 1-CH₃-3-CF₃-4-pyrazolyl | H | H | CH₃ | (CO)N(CH₃)₂ |
| 2.86 | 1-CH₃-3-CF₃-4-pyrazolyl | H | H | CH₃ | H |
| 2.87 | 1-CH₃-3-CF₃-4-pyrazolyl | H | H | CH₃ | (CO)N(CH₃)₂ |
| 2.88 | 1-CH₃-3-CF₃-4-pyrazolyl | H | H | CH₃ | (CO)NH(CH₃) |
| 2.89 | 1-CH₃-3-CF₃-4-pyrazolyl | H | H | CH₃ | (CO)CH₃ |
| 2.90 | 1-CH₃-3-CF₃-4-pyrazolyl | H | H | CH₃ | (CO)CH₃ |
| 2.91 | 1-CH₃-3-CF₃-4-pyrazolyl | H | H | CH₃ | H |
| 2.92 | 1-CH₃-3-CF₃-4-pyrazolyl | H | H | CH₃ | (CO)NH(CH₃) |
| 2.93 | 1-CH₃-3-CF₃-4-pyrazolyl | H | H | CH₃ | H |
| 2.94 | 1-CH₃-3-CF₃-4-pyrazolyl | H | H | CH₂CH₃ | H |
| 2.95 | 1-CH₃-3-CF₃-4-pyrazolyl | H | H | CH₂CH₃ | H |
| 2.96 | 1-CH₃-3-CF₃-4-pyrazolyl | H | H | CH₂CH₃ | H |
| 2.97 | 1-CH₃-3-CF₃-4-pyrazolyl | H | H | CH₂CH₃ | H |
| 2.98 | 1-CH₃-3-CF₃-4-pyrazolyl | H | H | CH₃ | H |
| 2.99 | 1-CH₃-3-CF₃-4-pyrazolyl | H | H | CH₃ | H |
| 2.100 | 1-CH₃-3-CF₃-4-pyrazolyl | H | H | CH₃ | (CO)N(CH₃)₂ |
| 2.101 | 1-CH₃-3-CF₃-4-pyrazolyl | H | H | CH₃ | (CO)NH(CH₃) |
| 2.102 | 1-CH₃-3-CF₃-4-pyrazolyl | H | H | CH₃ | (CO)NH₂ |
| 2.103 | 1-CH₃-3-CF₃-4-pyrazolyl | H | H | CH₃ | H |
| 2.104 | 1-CH₃-3-CF₃-4-pyrazolyl | H | H | CH₃ | (CO)N(CH₃)₂ |
| 2.105 | 1-CH₃-3-CF₃-4-pyrazolyl | H | H | CH₃ | (CO)N(CH₃)₂ |
| 2.106 | 1-CH₃-3-CF₃-4-pyrazolyl | H | H | CH₃ | (CO)N(CH₃)₂ |
| 2.107 | 1-CH₃-3-CF₃-4-pyrazolyl | H | H | CH₃ | H |
| 2.108 | 1-CH₃-3-CF₃-4-pyrazolyl | H | H | CH₃ | H |
| 2.109 | 1-CH₃-3-CF₃-4-pyrazolyl | H | H | CH₃ | (CO)N(CH₃)₂ |
| 2.110 | 1-CH₃-3-CF₃-4-pyrazolyl | H | H | CH₃ | (CO)NH₂ |
| 2.111 | 1-CH₃-3-CF₃-4-pyrazolyl | H | H | CH₃ | H |
| 2.112 | 1-CH₃-3-CF₃-4-pyrazolyl | H | H | CH₃ | (CO)N(CH₃)₂ |
| 2.113 | 1-CH₃-3-CF₃-4-pyrazolyl | H | H | CH₃ | H |
| 2.114 | 1-CH₃-3-CF₃-4-pyrazolyl | H | H | CH₃ | H |
| 2.115 | 1-CH₃-3-CF₃-4-pyrazolyl | H | H | CH₃ | H |
| 2.116 | 1-CH₃-3-CF₃-4-pyrazolyl | H | H | CH₃ | (CO)CH₃ |
| 2.117 | 1-CH₃-3-CF₃-4-pyrazolyl | H | H | CH₃ | (CO)NH(CH₃) |
| 2.118 | 1-CH₃-3-CF₃-4-pyrazolyl | H | H | CH₃ | H |
| 2.119 | 1-CH₃-3-CF₃-4-pyrazolyl | H | H | CH₃ | (CO)N(CH₃)₂ |
| 2.120 | 1-CH₃-3-CF₃-4-pyrazolyl | H | H | CH₃ | H |
| 2.121 | 1-CH₃-3-CF₃-4-pyrazolyl | H | H | CH₃ | (CO)NH(CH₃) |
| 2.122 | 1-CH₃-3-CF₃-4-pyrazolyl | H | H | CH₃ | H |
| 2.123 | 1-CH₃-3-CF₃-4-Pyrazolyl | H | H | CH₃ | H |
| 2.124 | 1-CH₃-3-CF₃-4-pyrazolyl | H | H | CH₃ | (CO)NH(CH₃) |

TABLE 2-continued

| No. | | | | | |
|---|---|---|---|---|---|
| 2.125 | 1-CH$_3$-3-CF$_3$-4-pyrazolyl | H | H | CH$_3$ | (CO)NH(CH$_3$) |
| 2.126 | 1-CH$_3$-3-CF$_3$-4-pyrazolyl | H | H | CH$_3$ | H |
| 2.127 | 1-CH$_3$-3-CF$_3$-4-pyrazolyl | H | H | CH$_3$ | H |
| 2.128 | 1-CH$_3$-3-CF$_3$-4-pyrazolyl | H | H | CH$_3$ | (CO)NH(CH$_3$) |
| 2.129 | 1-CH$_3$-3-CF$_3$-4-pyrazolyl | H | H | CH$_3$ | (CO)N(CH$_3$)$_2$ |
| 2.130 | 1-CH$_3$-3-CF$_3$-4-pyrazolyl | H | H | CH$_3$ | H |
| 2.131 | 1-CH$_3$-3-CF$_3$-4-pyrazolyl | H | H | CH$_3$ | (CO)N(CH$_3$)$_2$ |
| 2.132 | 1-CH$_3$-3-CF$_3$-4-pyrazolyl | H | H | CH$_3$ | (CO)CH$_3$ |
| 2.133 | 1-CH$_3$-3-CF$_3$-4-pyrazolyl | H | H | CH$_3$ | (CO)N(CH$_3$)$_2$ |
| 2.134 | 1-CH$_3$-3-CF$_3$-4-pyrazolyl | H | H | CH$_3$ | (CO)NH(CH$_3$) |
| 2.135 | 1-CH$_3$-3-CF$_3$-4-pyrazolyl | H | H | CH$_3$ | (CO)NH$_2$ |
| 2.136 | 1-CH$_3$-3-CF$_3$-4-pyrazolyl | H | H | CH$_3$ | (CO)NH(CH$_3$) |
| 2.137 | 1-CH$_3$-3-CF$_3$-4-pyrazolyl | H | H | CH$_3$ | H |
| 2.138 | 1-CH$_3$-3-CF$_3$-4-pyrazolyl | H | H | CH$_3$ | H |
| 2.139 | 1-CH$_3$-3-CF$_3$-4-pyrazolyl | H | H | CH$_3$ | H |
| 2.140 | 1-CH$_3$-3-CF$_3$-4-pyrazolyl | H | H | CH$_3$ | (CO)NH(CH$_3$) |
| 2.141 | 1-CH$_3$-3-CF$_3$-4-pyrazolyl | H | H | CH$_3$ | (CO)N(CH$_3$)$_2$ |
| 2.142 | 1-CH$_3$-3-CF$_3$-4-pyrazolyl | H | H | CH$_3$ | (CO)NH$_2$ |
| 2.143 | 1-CH$_3$-3-CF$_3$-4-pyrazolyl | H | H | CH$_3$ | (CO)N(CH$_3$)$_2$ |
| 2.144 | 1-CH$_3$-3-CF$_3$-4-pyrazolyl | H | H | CH$_3$ | (CO)NH$_2$ |
| 2.145 | 1-CH$_3$-3-CF$_3$-4-pyrazolyl | H | H | CH$_3$ | (CO)N(CH$_3$)$_2$ |
| 2.146 | 1-CH$_3$-3-CF$_3$-4-pyrazolyl | H | H | CH$_3$ | (CO)NH(CH$_3$) |
| 2.147 | 1-CH$_3$-3-CF$_3$-4-Pprazolyl | H | H | CH$_3$ | (CO)N(CH$_3$)$_2$ |
| 2.148 | 1-CH$_3$-3-CF$_3$-4-pyrazolyl | H | H | CH$_3$ | (CO)NH(CH$_3$) |
| 2.149 | 1-CH$_3$-3-CF$_3$-4-pyrazolyl | H | H | CH$_3$ | (CO)CH$_3$ |
| 2.150 | 1-CH$_3$-3-CF$_3$-4-pyrazolyl | H | H | CH$_3$ | (CO)N(CH$_3$)$_2$ |
| 2.151 | 1-CH$_3$-3-CF$_3$-4-pyrazolyl | H | H | CH$_3$ | H |
| 2.152 | 1-CH$_3$-3-CF$_3$-4-pyrazolyl | H | H | CH$_3$ | (CO)N(CH$_3$)$_2$ |
| 2.153 | 1-CH$_3$-3-CF$_3$-4-pyrazolyl | H | H | CH$_3$ | H |
| 2.154 | 1-CH$_3$-3-CF$_3$-4-pyrazolyl | H | H | CH$_3$ | H |
| 2.155 | 1-CH$_3$-3-CF$_3$-4-pyrazolyl | H | H | CH$_3$ | H |
| 2.156 | 1-CH$_3$-3-CF$_3$-4-pyrazolyl | H | H | CH$_3$ | H |
| 2.157 | 1-CH$_3$-3-CF$_3$-4-pyrazolyl | H | H | CH$_3$ | (CO)N(CH$_3$)$_2$ |
| 2.158 | 1-CH$_3$-3-CF$_3$-4-pyrazolyl | H | H | CH$_3$ | (CO)N(CH$_3$)$_2$ |
| 2.159 | 1-CH$_3$-3-CF$_3$-4-pyrazolyl | H | H | CH$_3$ | (CO)N(CH$_3$)$_2$ |
| 2.160 | 1-CH$_3$-3-CF$_3$-4-pyrazolyl | H | H | CH$_3$ | (CO)N(CH$_3$)$_2$ |
| 2.161 | 1-CH$_3$-3-CF$_3$-4-pyrazolyl | H | H | CH$_3$ | (CO)N(CH$_3$)$_2$ |
| 2.162 | 1-CH$_3$-3-CF$_3$-4-pyrazolyl | H | H | CH$_3$ | H |
| 2.163 | 1-CH$_3$-3-CF$_3$-4-pyrazolyl | H | H | CH$_3$ | H |
| 2.164 | 1-CH$_3$-3-CF$_3$-4-pyrazolyl | H | H | CH$_3$ | (CO)CH$_3$ |
| 2.165 | 1-CH$_3$-3-CF$_3$-4-pyrazolyl | H | H | CH$_3$ | (CO)N(CH$_3$)$_2$ |
| 2.166 | 1-CH$_3$-3-CF$_3$-4-pyrazolyl | H | H | CH$_3$ | (CO)NH(CH$_3$) |
| 2.167 | 1-CH$_3$-3-CF$_3$-4-pyrazolyl | H | H | CH$_3$ | (CO)N(CH$_3$)$_2$ |
| 2.168 | 1-CH$_3$-3-CF$_3$-4-pyrazolyl | H | H | CH$_3$ | (CO)N(CH$_3$)$_2$ |
| 2.169 | 1-CH$_3$-3-CF$_3$-4-pyrazolyl | H | H | CH$_3$ | (CO)N(CH$_3$)$_2$ |
| 2.170 | 1-CH$_3$-3-CF$_3$-4-pyrazolyl | H | H | CH$_3$ | (CO)NH(CH$_3$) |
| 2.171 | 1-CH$_3$-3-CF$_3$-4-pyrazolyl | H | H | CH$_3$ | (CO)N(CH$_3$)$_2$ |
| 2.172 | 1-CH$_3$-3-CF$_3$-4-pyrazolyl | H | H | CH$_3$ | (CO)N(CH$_3$)$_2$ |
| 2.173 | 1-CH$_3$-3-CF$_3$-4-pyrazolyl | H | H | CH$_3$ | H |
| 2.174 | 1-CH$_3$-3-CF$_3$-4-pyrazolyl | H | H | CH$_3$ | H |
| 2.175 | 1-CH$_3$-3-CF$_3$-4-pyrazolyl | H | H | CH$_3$ | H |
| 2.176 | 1-CH$_3$-3-CF$_3$-4-pyrazolyl | H | H | CH$_3$ | (CO)N(CH$_3$)$_2$ |
| 2.177 | 1-CH$_3$-3-CF$_3$-4-pyrazolyl | H | H | CH$_3$ | (CO)N(CH$_3$)$_2$ |
| 2.178 | 1-CH$_3$-3-CF$_3$-4-pyrazolyl | H | H | CH$_3$ | (CO)N(CH$_3$)$_2$ |
| 2.179 | 1-CH$_3$-3-CF$_3$-4-pyrazolyl | H | H | CH$_3$ | (CO)N(CH$_3$)$_2$ |
| 2.180 | 1-CH$_3$-3-CF$_3$-4-pyrazolyl | H | H | CH$_3$ | (CO)N(CH$_3$)$_2$ |
| 2.181 | 1-CH$_3$-3-CF$_3$-4-pyrazolyl | H | H | CH$_3$ | (CO)N(CH$_3$)$_2$ |
| 2.182 | 1-CH$_3$-3-CF$_3$-4-pyrazolyl | H | H | CH$_3$ | (CO)N(CH$_3$)$_2$ |
| 2.183 | 1-CH$_3$-3-CF$_3$-4-pyrazolyl | H | H | CH$_3$ | H |
| 2.184 | 1-CH$_3$-3-CF$_3$-4-pyrazolyl | H | H | CH$_3$ | (CO)N(CH$_3$)$_2$ |
| 2.185 | 1-CH$_3$-3-CF$_3$-4-pyrazolyl | H | H | CH$_3$ | (CO)NH(CH$_3$) |
| 2.186 | 1-CH$_3$-3-CF$_3$-4-pyrazolyl | H | H | CH$_3$ | (CO)CH$_3$ |
| 2.187 | 1-CH$_3$-3-CF$_3$-4-pyrazolyl | H | H | CH$_3$ | (CO)CH$_3$ |
| 2.188 | 1-CH$_3$-3-CF$_3$-4-pyrazolyl | H | H | CH$_3$ | H |
| 2.189 | 1-CH$_3$-3-CF$_3$-4-pyrazolyl | H | H | CH$_3$ | (CO)NH(CH$_3$) |
| 2.190 | 1-CH$_3$-3-CF$_3$-4-pyrazolyl | H | H | CH$_3$ | H |

| No. | R$^5$+ R$^6$ | Salt | MS (m$^+$ + H) | Mp (° C.) |
|---|---|---|---|---|
| 2.1 | —CH$_2$—O—C(CH$_3$)$_2$—O—CH$_2$— | | 395 | 162 |
| 2.2 | —CH$_2$—CH$_2$—O—CH$_2$—CH$_2$— | | 365 | 195 |
| 2.3 | —CH$_2$—CH$_2$—O—CH$_2$—CH$_2$— | | 436 | 222 |
| 2.4 | —CH$_2$—CH$_2$—O—CH$_2$—CH$_2$— | | 422 | 198 |
| 2.5 | —CH$_2$—CH$_2$—O—CH$_2$—CH$_2$— | | 408 | 198 |
| 2.6 | —CH$_2$—CH$_2$—O—CH$_2$—CH$_2$— | | 381 | 223 |
| 2.7 | —CH$_2$—CH$_2$—O—CH$_2$—CH$_2$— | | 452 | 215 |
| 2.8 | —CH$_2$—CH$_2$—S(O)—CH$_2$—CH$_2$— | | 468 | 225 |
| 2.9 | —CH$_2$—CH$_2$—S(O)$_2$—CH$_2$—CH$_2$— | | 484 | |
| 2.10 | —CH$_2$—CH$_2$—CH$_2$—CH$_2$—CH$_2$— | | 363 | 211 |

TABLE 2-continued

| | | | |
|---|---|---|---|
| 2.11 | —CH$_2$—CH$_2$—CH$_2$—CH$_2$— | 349 | 204 |
| 2.12 | —CH$_2$—CH$_2$—CH$_2$—CH$_2$—CH$_2$— | 434 | 195 |
| 2.13 | —CH$_2$—CH$_2$—CH$_2$—CH$_2$—CH$_2$— | 406 | 205 |
| 2.14 | —CH$_2$—CH$_2$—O—CH(CH$_3$)— | 365 | 210 |
| 2.15 | —CH$_2$—CH$_2$—S—CH$_2$— | 438 | 205 |
| 2.16 | —CH$_2$—CH$_2$—S—CH$_2$— | 367 | 215 |
| 2.17 | —CH$_2$—CH$_2$—CH$_2$—CH(CH$_2$CH$_2$CONHCH$_3$)— | 434 | 156 |
| 2.18 | —CH$_2$—CH$_2$—N(COOC(CH$_3$)$_3$)—CH$_2$— | 450 | 215 |
| 2.19 | —CH$_2$—CH$_2$—CH$_2$—CH$_2$— | 405 | 182 |
| 2.20 | —CH$_2$—CH$_2$—CH$_2$—CH$_2$—CH$_2$— | 420 | 145 |
| 2.21 | —CH$_2$—CH$_2$—C(—O—CH$_2$—CH$_2$—O—)—CH$_2$—CH$_2$— | 421 | 214 |
| 2.22 | —CH$_2$—CH$_2$—C(—O—CH$_2$—CH$_2$—O—)—CH$_2$CH$_2$— | 492 | 220 |
| 2.23 | —CH$_2$—CH$_2$—CH(OSi(CH$_3$)$_2$C(CH$_3$)$_3$)—CH$_2$—CH$_2$— | 493 | 174 |
| 2.24 | —CH$_2$—CH$_2$—O—CH(CH$_3$)— | 422 | 200 |
| 2.25 | —CH$_2$—CH$_2$—CH$_2$—CH(CH$_3$)— | 363 | 203 |
| 2.26 | —CH(CH$_3$)—CH$_2$—CH$_2$—CH(CH$_3$)— | 377 | 194 |
| 2.27 | —CH(CH$_3$)—CH$_2$—CH$_2$—CH(CH$_3$)— | 434 | 192 |
| 2.28 | —CH$_2$—CH$_2$—N(COOC(CH$_3$)$_3$)—CH$_2$— | 507 | |
| 2.29 | —CH$_2$—CH$_2$—CH$_2$—CH$_2$—CH$_2$—CH$_2$— | 391 | 175 |
| 2.30 | —CH$_2$—CH$_2$—CH$_2$—CH$_2$—CH$_2$—CH$_2$— | 377 | 185 |
| 2.31 | —CH$_2$—CH$_2$—CH$_2$—CH$_2$—CH$_2$— | 434 | 177 |
| 2.32 | —CH$_2$—CH$_2$—N(COO(CH$_3$)$_3$)—CH$_2$—CH$_2$— | 535 | 224 |
| 2.33 | —CH$_2$—CH$_2$—CH$_2$— | 335 | 210 |
| 2.34 | —CH$_2$—CH$_2$—CH$_2$— | 406 | 190 |
| 2.35 | —CH$_2$—CH$_2$—CH$_2$— | 391 | 170 |
| 2.36 | —CH$_2$—CH$_2$—CH$_2$—CH$_2$— | 420 | 228 |
| 2.37 | —CH$_2$—CH$_2$—CH$_2$—CH$_2$— | 406 | |
| 2.38 | —CH$_2$—CH$_2$—CH$_2$—CH$_2$— | 392 | 218 |
| 2.39 | —CH$_2$—CH$_2$—CH$_2$— | 392 | 200 |
| 2.40 | CH$_2$—CH—CH=CH—CH$_2$—CH— (with bridge between CH$_2$ and CH) | 373 | 132 |
| 2.41 | —CH—CH$_2$—CH$_2$—CH—CH$_2$— (bridged by CH$_2$) | 375 | 210 |
| 2.42 | —CH—CH=CH—CH—CH$_2$— (bridged by CH$_2$) | 373 | 192 |
| 2.43 | —CH—CH$_2$—CH$_2$—CH—CH$_2$— (bridged by CH$_2$) | 431 | 194 |
| 2.44 | —CH—CH$_2$—CH$_2$—CH—CH$_2$— (bridged by CH$_2$) | 446 | 207 |
| 2.45 | —CH—CH=CH—CH—CH$_2$— (bridged by CH$_2$) | 416 | 190 |
| 2.46 | —CH$_2$—CH$_2$—CH(OSi(CH$_3$)$_2$C(CH$_3$)$_3$)—CH$_2$—CH$_2$— | 537 | 175 |
| 2.47 | —CH—CH$_2$—CH$_2$—CH—CH$_2$— (bridged by CH$_2$) | 418 | 182 |
| 2.48 | —CH—CH=CH—CH—CH$_2$— (bridged by CH$_2$) | 444 | 210 |
| 2.49 | CH$_2$—CH—CH=CH—CH$_2$—CH— (bridged) | 429 | 95 |
| 2.50 | CH$_2$—CH—CH=CH—CH$_2$—CH— (bridged) | 444 | 156 |
| 2.51 | CH$_2$—CH—CH=CH—CH$_2$—CH— (bridged) | 429 | 182 |
| 2.52 | —CH$_2$—CH$_2$—CH$_2$— | 377 | 190 |
| 2.53 | —CH$_2$—CH$_2$—CH(OH)—CH$_2$—CH$_2$— | 450 | |

TABLE 2-continued

| | | | | |
|---|---|---|---|---|
| 2.54 | —CH₂—CH₂—CH(OH)—CH₂—CH₂— | | 379 | 80 |
| 2.55 | —CH₂—CH₂—C(O)—CH₂—CH₂— | | 448 | 188 |
| 2.56 | —CH₂—CH₂—CH₂—O—CH₂— | | 365 | |
| 2.57 | —CH₂—CH₂—N(CON(CH₃)₂)—CH₂—CH₂— | | 435 | 222 |
| 2.58 | —CH₂—CH₂—N(COCH₃)—CH₂—CH₂— | | 406 | |
| 2.59 | —CH₂—CH₂—NH—CH₂—CH₂— | HCl | 364 | |
| 2.60 | —CH₂—CH₂—N(CON(CH₃)₂)—CH₂—CH₂— | | 596 | 184 |
| 2.61 | —CH₂—CH₂—N(COCH₃)—CH₂—CH₂— | | 477 | 88 |
| 2.62 | —CH₂—CH₂—N(CH₃)—CH₂—CH₂— | | 449 | 212 |
| 2.63 | —CH₂—CH₂—NH—CH₂—CH₂— | HCl | 471 | 175 |
| 2.64 | —CH₂—CH₂—N(CH₂CN)—CH₂—CH₂— | | 474 | 197 |
| 2.65 | —CH₂—CH₂—O—CH₂— | | 351 | |
| 2.66 | —CH₂—O—CH₂— | | 337 | |
| 2.67 | 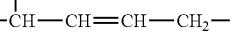 | | 415 | |
| 2.68 | —CH₂—O—CH₂— | | 408 | |
| 2.69 | —CH₂—CH₂—O—CH₂— | | 408 | |
| 2.70 | —CH₂—CH₂—O—CH₂— | | 422 | |
| 2.71 | —CH₂—CH₂—O—CH(CH₃)— | | 436 | 152 |
| 2.72 | —CH₂—CH₂—CH₂—CH(CH₃)— | | 434 | 198 |
| 2.73 | —CH₂—CH₂—CH₂—CH(CH₃)— | | 420 | 160 |
| 2.74 | —CH₂—CH₂—N(COOC(CH₃)₃)—CH₂— | | 521 | |
| 2.75 | —CH₂—CH₂—CH₂—CH₂—CH₂— | | 448 | 188 |
| 2.76 | —C(—NH—CH₃)=C(—O—CH₃)—C(=O)— | | 406 | 120 |
| 2.77 | —C(—O—CH₃)=C(—O—CH₃)—C(=O)— | | 407 | |
| 2.78 | —C(—O—CH₃)=C(—OH)—C(=O)— | | 393 | 165 |
| 2.79 | —CH₂—CH₂—NH—CH₂— | CF₃CO₂H | 420 | |
| 2.80 | —CH₂—CH₂—N(COO(CH₃))—CH₂— | | 479 | |
| 2.81 | —CH₂—CH₂—CH₂—O—CH₂— | | 436 | 198 |
| 2.82 | —CH₂—CH₂—C(=N—N—CO—CH₃)—CH₂—CH₂— | | 520 | |
| 2.83 | —CH₂—CH₂—C(=N—N—SO₂—CH₃)—CH₂—CH₂— | | 540 | |
| 2.84 | —CH₂—CH₂—C(=N—OH)—CH₂—CH₂— | | 463 | |
| 2.85 | —CH₂—CH₂—C(=N—O—CH₃)—CH₂—CH₂— | | 477 | |
| 2.86 | —CH₂—CH₂—CF₂—CH₂—CH₂— | | 399 | |
| 2.87 | —CH₂—CH₂—CF₂—CH₂—CH₂— | | 470 | |
| 2.88 | —CH₂—CH₂—CF₂—CH₂—CH₂— | | 456 | |
| 2.89 | 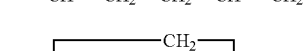 | | 417 | 95 |
| 2.90 |  | | 415 | |
| 2.91 | 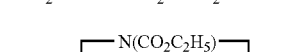 | | 462 | |
| 2.92 | 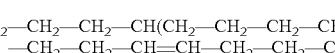 | | 519 | 134 |
| 2.93 | —CH₂—CH₂—CH₂—CH(CH₂—CH₂—CH₂—CH₂—CH₃)— | | 419 | 148 |
| 2.94 | —CH₂—CH₂—CH=CH—CH₂—CH₂—CH₂— | | 404 | |
| 2.95 | —CH₂—CH₂—CH₂— | | 350 | |
| 2.96 | 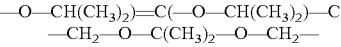 | | 390 | 97 |
| 2.97 | —C(—O—CH(CH₃)₂)=C(—O—CH(CH₃)₂)—C(=O)— | | 478 | |
| 2.98 | —CH₂—O—C(CH₃)₂—O—CH₂— | | 395 | 162 |
| 2.99 | —CH₂—CH₂—O—CH₂—CH₂— | | 365 | 195 |
| 2.100 | —CH₂—CH₂—O—CH₂—CH₂— | | 436 | 222 |
| 2.101 | —CH₂—CH₂—O—CH₂—CH₂— | | 422 | 198 |
| 2.102 | —CH₂—CH₂—O—CH₂—CH₂— | | 408 | 198 |
| 2.103 | —CH₂—CH₂—S—CH₂—CH₂— | | 381 | 223 |
| 2.104 | —CH₂—CH₂—S—CH₂—CH₂— | | 452 | 215 |
| 2.105 | —CH₂—CH₂—S(O)—CH₂—CH₂— | | 468 | 225 |
| 2.106 | —CH₂—CH₂—S(O)₂—CH₂—CH₂— | | 484 | |
| 2.107 | —CH₂—CH₂—CH₂—CH₂— | | 363 | 211 |
| 2.108 | —CH₂—CH₂—CH₂—CH₂— | | 349 | 204 |
| 2.109 | —CH₂—CH₂—CH₂—CH₂—CH₂— | | 434 | 195 |
| 2.110 | —CH₂—CH₂—CH₂—CH₂—CH₂— | | 406 | 205 |
| 2.111 | —CH₂—CH₂—O—CH(CH₃)— | | 365 | 210 |

TABLE 2-continued

| | | | |
|---|---|---|---|
| 2.112 | —CH₂—CH₂—S—CH₂— | 438 | 205 |
| 2.113 | —CH₂—CH₂—S—CH₂— | 367 | 215 |
| 2.114 | —CH₂—CH₂—CH₂—CH(CH₂CH₂CONHCH₃)— | 434 | 156 |
| 2.115 | —CH₂—CH₂—N(COOC(CH₃)₃)—CH₂— | 450 | 215 |
| 2.116 | —CH₂—CH₂—CH₂—CH₂— | 405 | 182 |
| 2.117 | —CH₂—CH₂—CH₂—CH₂—CH₂— | 420 | 145 |
| 2.118 | —CH₂—CH₂—C(—O—CH₂—CH₂—O—)—CH₂—CH₂— | 421 | 214 |
| 2.119 | —CH₂—CH₂—C(—O—CH₂—CH₂—O—)—CH₂—CH₂— | 492 | 220 |
| 2.120 | —CH₂—CH₂—CH(OSi(CH₃)₂C(CH₃)₃)—CH₂—CH₂— | 493 | 174 |
| 2.121 | —CH₂—CH₂—O—CH(CH₃)— | 422 | 200 |
| 2.122 | —CH₂—CH₂—CH₂—CH(CH₃)— | 363 | 203 |
| 2.123 | —CH(CH₃)—CH₂—CH₂—CH(CH₃)— | 377 | 194 |
| 2.124 | —CH(CH₃)—CH₂—CH₂—CH(CH₃)— | 434 | 192 |
| 2.125 | —CH₂—CH₂—N(COOC(CH₃)₃)—CH₂— | 507 | |
| 2.126 | —CH₂—CH₂—CH₂—CH₂—CH₂—CH₂— | 391 | 175 |
| 2.127 | —CH₂—CH₂—CH₂—CH₂—CH₂—CH₂— | 377 | 185 |
| 2.128 | —CH₂—CH₂—CH₂—CH₂—CH₂—CH₂— | 434 | 177 |
| 2.129 | —CH₂—CH₂—N(COO(CH₃)₃)—CH₂—CH₂— | 535 | 224 |
| 2.130 | —CH₂—CH₂—CH₂— | 335 | 210 |
| 2.131 | —CH₂—CH₂—CH₂— | 406 | 190 |
| 2.132 | —CH₂—CH₂—CH₂—CH₂— | 391 | 170 |
| 2.133 | —CH₂—CH₂—CH₂—CH₂— | 420 | 228 |
| 2.134 | —CH₂—CH₂—CH₂—CH₂— | 406 | |
| 2.135 | —CH₂—CH₂—CH₂—CH₂— | 392 | 218 |
| 2.136 | —CH₂—CH₂—CH₂— | 392 | 200 |
| 2.137 | 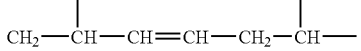 | 373 | 132 |
| 2.138 | 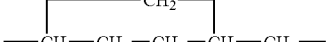 | 375 | 210 |
| 2.139 | 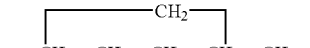 | 373 | 192 |
| 2.140 | 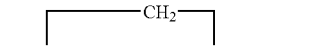 | 431 | 194 |
| 2.141 | 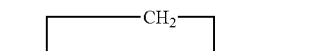 | 446 | 207 |
| 2.142 | 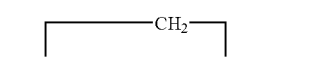 | 416 | 190 |
| 2.143 | —CH₂—CH₂—CH(OSi(CH₃)₂C(CH₃)₃)—CH₂—CH₂— | 537 | 175 |
| 2.144 | 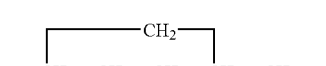 | 418 | 182 |
| 2.145 |  | 444 | 210 |
| 2.146 |  | 429 | 95 |
| 2.147 | 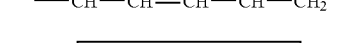 | 444 | 156 |
| 2.148 | 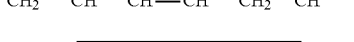 | 429 | 182 |
| 2.149 | —CH₂—CH₂—CH₂— | 377 | 190 |
| 2.150 | —CH₂—CH₂—CH(OH)—CH₂—CH₂— | 450 | |
| 2.151 | —CH₂—CH₂—CH(OH)—CH₂—CH₂— | 379 | 80 |
| 2.152 | —CH₂—CH₂—C(O)—CH₂—CH₂— | 448 | 188 |
| 2.153 | —CH₂—CH₂—CH₂—O—CH₂— | 365 | |
| 2.154 | —CH₂—CH₂—N(CON(CH₃)₂)—CH₂—CH₂— | 435 | 222 |

TABLE 2-continued

| | | | | |
|---|---|---|---|---|
| 2.155 | —CH₂—CH₂—N(COCH₃)—CH₂—CH₂— | | 406 | |
| 2.156 | —CH₂—CH₂—NH—CH₂—CH₂— | HCl | 364 | |
| 2.157 | —CH₃—CH₂—N(CON(CH₃)₂)—CH₂—CH₂— | | 596 | 184 |
| 2.158 | —CH₂—CH₂—N(COCH₃)—CH₂—CH₂— | | 477 | 88 |
| 2.159 | —CH₂—CH₂—N(CH₃)—CH₂—CH₂— | | 449 | 212 |
| 2.160 | —CH₂—CH₂—NH—CH₂—CH₂— | HCl | 471 | 175 |
| 2.161 | —CH₂—CH₂—N(CH₂CN)—CH₂—CH₂— | | 474 | 197 |
| 2.162 | —CH₂—CH₂—O—CH₂— | | 351 | |
| 2.163 | —CH₂—O—CH₂— | | 337 | |
| 2.164 | CH₂—CH—CH=CH—CH₂—CH— (bridged) | | 415 | |
| 2.165 | —CH₂—O—CH₂— | | 408 | |
| 2.166 | —CH₂—CH₂—O—CH₂— | | 408 | |
| 2.167 | —CH₂—CH₂—O—CH₂— | | 422 | |
| 2.168 | —CH₂—CH₂—O—CH(CH₃)— | | 436 | 152 |
| 2.169 | —CH₂—CH₂—CH₂—CH(CH₃)— | | 434 | 198 |
| 2.170 | —CH₂—CH₂—CH₂—CH(CH₃)— | | 420 | 160 |
| 2.171 | —CH₂—CH₂—N(COOC(CH₃)₃)—CH₂— | | 521 | |
| 2.172 | —CH₂—CH₂—CH₂—CH₂—CH₂— | | 448 | 188 |
| 2.173 | —C(—NH—CH₃)=C(—O—CH₃)—C(=O)— | | 406 | 120 |
| 2.174 | —C(—O—CH₃)=C(—O—CH₃)—C(=O)— | | 407 | |
| 2.175 | —C(—O—CH₃)=C(—OH)—C(=O)— | | 393 | 165 |
| 2.176 | —CH₂—CH₂—NH—CH₂— | CF₃CO₂H | 420 | |
| 2.177 | —CH₂—CH₂—N(COO(CH₃))—CH₂— | | 479 | |
| 2.178 | —CH₂—CH₂—CH₂—O—CH₂— | | 436 | 198 |
| 2.179 | —CH₂—CH₂—C(=N—N—CO—CH₃)—CH₂—CH₂— | | 520 | |
| 2.180 | —CH₂—CH₂—C(=N—N—SO₂—CH₃)—CH₂—CH₂— | | 540 | |
| 2.181 | —CH₂—CH₂—C(=N—OH)—CH₂—CH₂— | | 463 | |
| 2.182 | —CH₂—CH₂—C(=N—O—CH₃)—CH₂—CH₂— | | 477 | |
| 2.183 | —CH₂—CH₂—CF₂—CH₂—CH₂— | | 399 | |
| 2.184 | —CH₂—CH₂—CF₂—CH₂—CH₂— | | 470 | |
| 2.185 | —CH₂—CH₂—CF₂—CH₂—CH₂— | | 456 | |
| 2.186 | —CH—CH₂—CH₂—CH—CH₂— (bridged CH₂) | | 417 | 95 |
| 2.187 | —CH—CH=CH—CH—CH₂— (bridged CH₂) | | 415 | |
| 2.188 | —CH₂—CH—CH₂—CH₂—CH—CH₂— (bridged N(CO₂C₂H₅)) | | 462 | |
| 2.189 | —CH₂—CH—CH₂—CH₂—CH—CH₂— (bridged N(CO₂C₂H₅)) | | 519 | 134 |
| 2.190 | —CH₂—CH₂—CH₂—CH(CH₂—CH₂—CH₂—CH₂—CH₃)— | | 419 | 148 |

TABLE 3

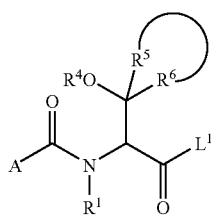

(III)

(Intermediates of formula III)

| No. | A | R¹ | R² | L¹ | R⁴ | R⁵ + R⁶ | MS (m⁺ + H) | Mp (° C.) |
|---|---|---|---|---|---|---|---|---|
| 3.1 | 1-CH₃-3-CF₃-4-pyrazolyl | H | H | —O—CH₂—CH₃ | H | —CH₂—CH₂—CH₂— | 350 | |
| 3.2 | 1-CH₃-3-CF₃-4-pyrazolyl | H | H | —O—CH₂—CH₃ | H | —CH₂—CH(O—CH₂CH(CH₃)₂)—CH2— | 422 | |

TABLE 3-continued

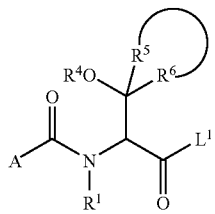

(III)

(Intermediates of formula III)

| No. | A | $R^1$ | $R^2$ | $L^1$ | $R^4$ | $R^5 + R^6$ | MS ($m^+ + H$) | Mp (° C.) |
|---|---|---|---|---|---|---|---|---|
| 3.3 | 1-$CH_3$-3-$CF_3$-4-pyrazolyl | H | H | —O—$CH_2$—$CH_3$ | H | —$CH_2$—$CH_2$—CH($CH_3$)—$CH_2$—$CH_2$— | 392 | |
| 3.4 | 1-$CH_3$-3-$CF_3$-4-pyrazolyl | H | H | —O—$CH_2$—$CH_3$ | H | —$CH_2$—$CH_2$—N(O—$CH_2$—$CH_3$)—$CH_2$—$CH_2$— | 423 | 120 |
| 3.4 | 1-$CH_3$-3-$CF_3$-4-pyrazolyl | H | H | —O—$CH_2$—$CH_3$ | H | —$CH_2$—$CH_2$—CH($CF_3$)—$CH_2$—$CH_2$— | 446 | 140 |

Biological Activity

The compounds of the formula (I) and their agriculturally useful salts are suitable, both in the form of isomer mixtures and in the form of the pure isomers, as herbicides. The herbicidal compositions comprising compounds of the formula (I) control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula (I), or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus armeniaca, Prunus avium, Prunus cerasus, Prunus dulcis, Prunus domestica, Prunus persica, Pyrus communis, Ribes sylvestre, Ricinus communis, Saccharum officinarum, Secale cereale, Sinapis alba, Solanum tuberosum, Sorghum bicolor (s. vulgare), Theobroma cacao, Trifolium pratense, triticale, Triticum aestivum, Triticum durum, Vicia faba, Vitis vinifera* and *Zea mays.*

In addition, the compounds of the formula (I) may also be used in crops which tolerate the action of herbicides owing to breeding, including genetic engineering methods.

In addition, the compounds of the formula (I) can also be used in crops which tolerate attack by insects or fungi owing to breeding, including genetic engineering methods.

The compounds of the formula (I), or the herbicidal compositions comprising them, can be used for example in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

The herbicidal compositions comprise a herbicidally effective amount of at least one compound of the formula (I) or an agriculturally useful salt of (I), and auxiliaries which are customary for the formulation of crop protection agents.

Examples of auxiliaries customary for formulating crop protection agents are inert auxiliaries, solid carriers, surfactants (such as dispersants, protective colloids, emulsifiers, wetting agents and tackifiers), organic and inorganic thickeners, bactericides, antifreeze agents, antifoams, if appropriate colorants, and, for seed formulations, adhesives.

Examples of thickeners (i.e. compounds which bestow modified flow properties to the formulation, i.e. high viscosity in the state of rest and low viscosity in the agitated state) are polysaccharides and also organic and inorganic sheet minerals, such as xanthan gum (Kelzan® from Kelco), Rhodopol® 23 (Rhone Poulenc) or Veegum® (from R.T. Vanderbilt) or Attaclay® (from Engelhardt).

Examples of antifoams are silicone emulsions (such as, for example Silikon® SRE, from Wacker or Rhodorsil® from Rhodia), long-chain alcohols, fatty acids, salts of fatty acids, organofluorine compounds and mixtures thereof.

Bactericides may be added for stabilizing the aqueous herbicide formulation. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivatives, such as alkyl isothiazolinones and benzisothiazolinones (Acticide MBS from Thor Chemie)

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable as inert auxiliaries are essentially the following:

mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Solid carriers are mineral earths, such as silicic acids, silica gels, silicates, talc, kaolin, limestone, lime, chalk, boll, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and vegetable products, such as cereal meal, tree bark meal, wood meal and nutshell meal, cellulose powder or other solid carriers.

Suitable surfactants (adjuvants, wetting agents, tackifiers, dispersants or emulsifiers) are the alkali metal salts, alkaline earth metal salts and ammonium salts of aromatic sulfonic acids, e.g. ligno- (Borresperse types Borregaard), phenol-, naphthalene- (Morwet types, Akzo Nobel) and dibutylnaphthalenesulfonic acid (Nekal types BASF), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl, octyl- or nonylphenol, alkylphenyl or tributylphenyl polyglycol ether, alkylaryl polyether alcohols, isotridecyl alcohol, alkoxylates, for example fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose, and also proteins, denatured proteins, polysaccharides (for example methylcellulose), hydrophobically modified starches, polyvinyl alcohol (Mowiol types Clariant), polycarboxylates (BASF Sokalan types), polyalkoxylates, polyvinylamine (BASF Lupamin types), polyethyleneimine (BASF Lupasol types), polyvinylpyrrolidone and copolymers thereof.

Powders, materials for broadcasting and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

The concentrations of the compounds of the formula (I) in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The following are examples of formulations:

1. Products for Dilution with Water

A Water-Soluble Concentrates 10 parts by weight of the active compounds are dissolved in 90 parts by weight of water or in a water-soluble solvent. As an alternative, wetting agents or other auxiliaries are added. The active compound dissolves upon dilution with water. In this way, a formulation having a content of 10% by weight of active compound is obtained.

B Dispersible Concentrates 20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of the active compounds are dissolved in 75 parts by weight of an organic solvent with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of the active compounds are dissolved in 35 parts by weight of an organic solvent with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion. The formulation has an active compound content of 25% by weight.

E Suspensions

In an agitated ball mill, 20 parts by weight of the active compounds are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of the active compounds are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of the active compounds are ground in a rotor-stator mill with addition of 25 parts by weight of dispersants, wetting agents and silica gel. Dilution with water gives a stable dispersion or solution of the active compound. The active compound content of the formulation is 75% by weight.

H Gel Formulations

In a ball mill, 20 parts by weight of the active compounds, 10 parts by weight of dispersant, 1 part by weight of gelling agent and 70 parts by weight of water or an organic solvent are ground to give a fine suspension. On dilution with water, a stable suspension having an active compound content of 20% by weight is obtained.

2. Products to be Applied Undiluted

I Dustable Powders 5 parts by weight of the active compounds are ground finely and mixed intimately with 95 parts by weight of finely divided kaolin. This gives a dustable product having an active compound content of 5% by weight.

J Granules (GR, FG, GG, MG)

0.5 part by weight of the active compounds is ground finely and associated with 99.5 parts by weight of carriers. Current methods are extrusion, spray-drying or the fluidized bed. This gives granules to be applied undiluted having an active compound content of 0.5% by weight.

K ULV Solutions (UL)

10 parts by weight of the active compounds are dissolved in 90 parts by weight of an organic solvent, for example xylene. This gives a product to be applied undiluted having an active compound content of 10% by weight.

The compounds of the formula (I) or the herbicidal compositions can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the compounds of the formula (I) or the herbicidal compositions can be applied by treating seed.

The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula (I) according to the invention or the compositions prepared therefrom. Here, the herbicidal compositions can be applied diluted or undiluted.

The term seed comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the compound of the formula (I) are from 0.001 to 3.0, preferably 0.01 to 1.0, kg/ha of active substance (a.s.), depending on the control target, the season, the target plants and the growth stage.

For seed treatment, amounts of from 0.001 to 10 kg per 100 kg of seed are usually employed.

To widen the spectrum of action and to achieve synergistic effects, the 3-(heterocyclyl)-substituted benzoylpyrazole compounds of the formula (I) may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acids and their derivatives, benzoic acid and its derivatives, benzothiadiazinones, 2-(het)aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils and phenylpyrazolines, isoxazolines and their derivatives.

It may furthermore be beneficial to apply the compounds of the formula (I) alone or in combination with other herbicides, or in the form of a mixture with other crop protection agents, together, for example, with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

Use Examples

The herbicidal activity of the heteroaroyl-substituted serineamides of the formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The rate of application for the post-emergence treatment was 1.0 kg/ha of a.s. (active substance).

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
| --- | --- |
| Amaranthus retroflexus | pig weed |
| Chenopodium album | lambsquarters |
| Setaria viridis | green foxtail |

At application rates of 1 kg/ha, the compounds 2.2, 2.7, 2.9, 2.12, 2.14, 2.15, 2.19, 2.21, 2.22, 2.24, 2.27, 2.28, 2.31, 2.34, 2.35, 2.36, 2.38, 2.41, 2.43, 2.44, 2.46, 2.48, 2.50, 2.51, 2.53, 2.55, 2.56, 2.57, 2.60, 2.61, 2.71, 2.72, 2.74, 2.80, 2.82, 2.83, 2.85, 2.86, 2.87, 2.88, 2.100, 2.101, 2.102, 2.104, 2.105, 2.106, 2.107, 2.109, 2.111, 2.112, 2.116, 2.117, 2.118, 2.119, 2.121, 2.124, 2.125, 2.128, 2.131, 2.132, 2.133, 2.135, 2.136, 2.137, 2.138, 2.140, 2.141, 2.143, 2.145, 2.147, 2.148, 2.149, 2.150, 2.152, 2.153, 2.154, 2.157, 2.158, 2.164, 2.168, 2.169, 2.170, 2.171, 2.177, 2.179, 2.180, 2.181, 2.182, 2.183, 2.184, 2.185, 2.186, 2.187, 2.188, 2.189 and 2.190 showed very good (>80%) post-emergence action against the unwanted plants *Amaranthus retroflectus, Chenopodium album* and *Setaria viridis*.

We claim:

1. A heteroaroyl-substituted serineamide of the formula (I)

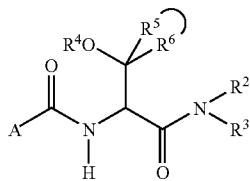

in which the variables are as defined below:

A is 5- or 6-membered heteroaryl having one to four nitrogen atoms, or one to three nitrogen atoms and one oxygen or sulfur atom, or one oxygen, or sulfur atom, which heteroaryl may be partially or fully halogenated and/or may carry 1 to 3 radicals selected from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;

$R^1$, $R^2$ are hydrogen, hydroxyl or $C_1$-$C_6$-alkoxy;

$R^3$ is $C_1$-$C_6$-alkyl, $C_1$-$C_4$-cyanoalkyl or $C_1$-$C_6$-haloalkyl;

$R^4$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, di-($C_1$-$C_6$-alkyl)-aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl) -aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, ($C_1$-$C_6$)alkylaminothiocarbonyl, di-($C_1$-$C_6$-alkyl)aminothiocarbonyl, ($C_1$-$C_6$-alkyl)cyanoimino, (amino)cyanoimino, [($C_1$-$C_6$-alkyl)amino]cyanoimino, [di($C_1$-$C_6$-alkyl) -amino]cyanoimino, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl, N-(di-$C_1$-$C_6$-alkylamino)imino -$C_1$-$C_6$-alkyl or tri-$C_1$-$C_4$-alkylsilyl, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, di-($C_1$-$C_4$-alkyl)amino, $C_1$-$C_4$-alkyl-$C_1$-$C_4$-alkoxycarbonylamino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, or phenyl-$C_1$-$C_6$-alkylcarbonyl, where the phenyl radical may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or $SO_2R^7$;

$R^5$ and $R^6$ together with the carbon atom to which they are attached form a first 3- to 12-membered saturated or partially unsaturated ring which is carbocyclic or contains 1 to 3 nitrogen atoms, 0 to 3 nitrogen atoms and 1 oxygen or sulfur atom, 0 to 2 nitrogen atoms and 2 oxygen or sulfur atoms, 0 or 1 nitrogen atom and 1 oxygen and 1 sulfur atom, 3 oxygen or sulfur atoms, 2 oxygen atoms and 1 sulfur atom, or 1 oxygen atom and 2 sulfur atoms, where the first ring is unsubstituted or substituted by 1 to 3 substituents, in the case of halogen also up to the maximum possible number, selected from the group consisting of halogen, cyano, nitro, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, hydroxyl, $C_1$-$C_6$-alkoxy, $C_3$-$C_6$-alkenyloxy, $C_3$-$C_6$-alkynyloxy, trialkylsilyloxy, formyl, $C_1$-$C_6$-alkyl -carbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, aminocarbonyl, $C_1$-$C_6$-alkylaminocarbonyl, $C_3$-$C_6$-alkenylamino-carbonyl, $C_3$-$C_6$-alkynylaminocarbonyl, di-($C_1$-$C_6$-alkyl) -aminocarbonyl, N—($C_3$-$C_6$-alkenyl)-N—($C_1$-$C_6$-alkyl)-aminocarbonyl, N—($C_3$-$C_6$-alkynyl)-N—($C_1$-$C_6$-alkyl)-aminocarbonyl, N—($C_1$-$C_6$-alkoxy)-N—($C_1$-$C_6$-alkyl) -amino-carbonyl, N—($C_3$-$C_6$-alkenyl)-N—($C_1$-$C_6$-alkoxy)-aminocarbonyl, N—($C_3$-$C_6$-alkynyl)-N—($C_1$-$C_6$-alkoxy)-aminocarbonyl, di-($C_1$-$C_6$-alkyl)-aminothiocarbonyl, $C_1$-$C_6$-alkoxyimino-$C_1$-$C_6$-alkyl, N—($C_1$-$C_6$-alkylamino)-imino-$C_1$-$C_6$-alkyl or N-(di-$C_1$-$C_6$-alkylamino)-imino-$C_1$-$C_6$-alkyl, amino, formylamino, $C_1$-$C_6$-alkylcarbonylamino, $C_1$-$C_6$-alkoxycarbonylamino, $C_1$-$C_6$-alkylamino, formyl -$C_1$-$C_6$-alkylamino, $C_1$-$C_6$-alkylcarbonyl-$C_1$-$C_6$-alkylamino, $C_1$-$C_6$-alkoxycarbonyl-$C_1$-$C_6$-alkylamino, di-($C_1$-$C_6$-alkyl)amino, amino-carbonylamino, $C_1$-$C_6$-alkylamino-carbonylamino, di($C_1$-$C_6$-)alkylamino-carbonylamino, $C_1$-$C_6$-alkylthio, $C_1$-$C_6$alkylsulfonyl, alkylsulfonyloxy, alkylsulfonylamino, $C_1$-$C_6$-alkylsulfinyl, $C_1$-$C_6$-alkylsulfimino, $C_1$-$C_6$-alkyl-$C_1$-$C_6$-alkylsulfimino, carbonyl, thiocarbonyl, imino, alkylimino, hydroxyimino, alkoxyimino, aminoimino, alkylaminoimino, di-(alkyl)aminoimino, alkylcarbonylaminoimino, alkylsulfonylaminoimino, $C_1$-$C_6$-vinylidenyl, $C_1$-$C_6$-alkoxyvinylidene, di-$C_1$-$C_6$-alkylaminovinylidene, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di-($C_1$-$C_4$-alkyl)-amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)-aminocarbonyl or $C_1$-$C_4$-alkylcarbonyloxy, phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)-aminocarbonyl, phenyl-$C_1$-$C_6$-alkylcarbonyl, heterocyclyl, heterocyclyl-$C_1$-$C_6$-alkyl, heterocyclylcarbonyl, heterocyclylsulfonylaminocarbonyl, heterocyclylcarbonyl-$C_1$-$C_6$-alkyl, heterocyclyloxy-carbonyl, heterocyclylaminocarbonyl, N—($C_1$-$C_6$-alkyl)-N-(heterocyclyl)-aminocarbonyl and heterocyclyl-$C_1$-$C_6$-alkylcarbonyl, wherein the phenyl and the heterocyclyl radical of the 17 last-mentioned substituents may be partially or fully halogenated and/or may carry one to three substituents selected from the group consisting of nitro, cyano, $C_1$-$C_4$alkyl, $C_1$-$C_4$-haloalkyl, $C_1$-$C_4$-alkoxy and $C_1$-$C_4$-haloalkoxy;

and where the first ring is monocyclic or fused to a second 3- to 7-membered saturated, partially unsaturated or fully unsaturated ring which is carbocyclic or contains 1 to 3 nitrogen atoms, 0 to 2 nitrogen atoms and 1 oxygen atom or sulfur atom, 0 to 1 nitrogen atom and 2 oxygen atoms or sulfur atoms, 0 to 1 nitrogen atom and 1 oxygen atom and 1 sulfur atom, 2 oxygen atoms and 1 sulfur atom, or 1 oxygen atom and 2 sulfur atoms, where the fused ring is unsubstituted or substituted by 1 to 3 substituents, in the case of halogen also up to the maximum possible number, selected from the group consisting of halogen, cyano, nitro, $C_1$-$C_6$-alkyl, $C_3$-$C_6$-alkenyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl, and where the first ring is not bridged or bridged by a 1- to 4-membered saturated or unsaturated chain which contains no heteroatoms or contains 1 to 2 nitrogen atoms, 0 or 1 nitrogen atom and 1 oxygen atom or 1 sulfur atom, 0 or 1 nitrogen atom and 2 oxygen atoms or 2 sulfur atoms, or 0 or 1 nitrogen atom and 1 oxygen atom and 1 sulfur atom, where the bridge is unsubstituted or substituted by 1 to 3 substituents, in the case of halogen also up to the maximum possible number, selected from the group consisting of halogen, cyano, nitro, $C_1$-$C_6$-alkyl, $C_3$-$C_6$-alkenyl, $C_1$-$C_6$-haloalkyl, $C_3$-$C_6$-haloalkenyl, $C_3$-$C_6$-haloalkynyl, hydroxyl, $C_1$-$C_6$-alkoxy, $C_1$-$C_6$-haloalkoxy and $C_1$-$C_6$-alkylsulfonyl;

$R^7$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_6$-alkoxy or an agriculturally useful salt thereof.

2. The heteroaroyl-substituted serineamide of the formula (I) according to claim 1 where A is 5- or 6-membered heteroaryl selected from the group consisting of pyrrolyl, thienyl, furyl, pyrazolyl, imidazolyl, thiazolyl, oxazolyl, tetrazolyl, pyridyl and pyrimidinyl; where the heteroaryl radicals mentioned may be partially or fully halogenated and/or may carry 1 to 3 radicals selected from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

3. The heteroaroyl-substituted serineamide of the formula (I) according to claim 1, where $R^1$ $R^2$ are hydrogen.

4. The heteroaroyl-substituted serineamide of the formula (I) according to claim 1, where $R^5$ and $R^6$ together with the carbon atom to which they are attached form a first 3- to 7-membered saturated or partially unsaturated ring which is carbocyclic or contains 1 or 2 nitrogen atoms, 0 or 1 nitrogen atom and 1 oxygen atom or sulfur atom, 0 or 1 nitrogen atom and 1 oxygen and 1 sulfur atom or 2 oxygen or sulfur atoms, where the first ring is unsubstituted or substituted as indicated in formula (I), and where the first ring is monocyclic or fused to a second 3- to 6-membered saturated or partially unsaturated ring, which is carbocyclic or contains 1 or 2 nitrogen atoms, 0 to 1 nitrogen atom or 1 oxygen atom or sulfur atom, 2 oxygen atoms or sulfur atoms, 0 to 1 nitrogen atom and 1 oxygen atom and 1 sulfur atom, where the fused ring is unsubstituted or substituted by 1 to 3, in the case of halogen also up to the maximum possible number, substituents selected from the group consisting of halogen, $C_1$-$C_6$-alkyl, $C_1$-$C_6$-haloalkyl and $C_1$-$C_6$-alkoxy, and where the first ring is not bridged or bridged by a 1- to 3-membered saturated or unsaturated chain which contains no heteroatoms or contains 1 nitrogen atom, 0 or 1 nitrogen atom and 1 oxygen atom or 1 sulfur atom, where the bridge is unsubstituted or substituted by 1 to 3 substituents, in the case of halogen also up to the maximum possible number, selected from the group consisting of halogen, $C_1$-$C_6$-alkyl, hydroxy and $C_1$-$C_6$-alkoxy.

5. A process for preparing a heteroaroyl-substituted serineamide of the formula (I) according to claim 1, comprising reacting a serine derivative of the formula (V)

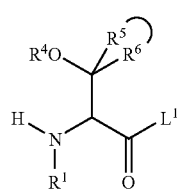

(V)

wherein $L^1$ is hydroxyl or $C_1$-$C_6$-alkoxy, with a heteroaryl acid derivative of the formula (IV)

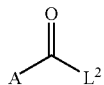
(IV)

wherein $L^2$ is hydroxyl, halogen, $C_1$-$C_6$-alkylcarbonyl, $C_1$-$C_6$-alkoxycarbonyl, $C_1$-$C_4$-alkylsulfonyl, phosphonyl or isoureyl, to give the corresponding heteroaroyl derivative of the formula (III)

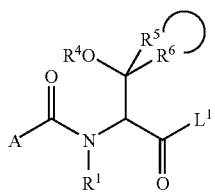
(III)

and reacting the resulting heteroaroyl derivative of the formula (III) with an amine of the formula (II)

$$HNR^2R^3 \quad (II)$$

to obtain the compound of formula (I).

6. A composition, comprising a herbicidally effective amount of the at least one heteroaroyl-substituted serineamide of the formula (I) or an agriculturally useful salt of formula (I) according to claim 1 and auxiliaries customary for formulating crop protection agents.

7. A process for preparing compositions according to claim 6, wherein a herbicidally effective amount of the at least one heteroaroyl-substituted serineamide of the formula (I) or an agriculturally useful salt thereof and auxiliaries customary for formulating crop protection agents are mixed.

8. A method for controlling unwanted vegetation, wherein a herbicidally effective amount of the at least one heteroaroyl-substituted serineamide of the formula (I) or an agriculturally useful salt of formula (I) according to claim 1 is allowed to act on plants, their habitat and/or on seed.

* * * * *

UNITED STATES PATENT AND TRADEMARK OFFICE
CERTIFICATE OF CORRECTION

PATENT NO. : 8,133,851 B2
APPLICATION NO. : 12/522644
DATED : March 13, 2012
INVENTOR(S) : Matthias Witschell et al.

Page 1 of 1

It is certified that error appears in the above-identified patent and that said Letters Patent is hereby corrected as shown below:

In claim 3, col. 80, line 20, after "$R^1$" insert --and--.

Signed and Sealed this
Tenth Day of July, 2012

David J. Kappos
*Director of the United States Patent and Trademark Office*